(12) United States Patent
Pan

(10) Patent No.: US 11,969,207 B2
(45) Date of Patent: Apr. 30, 2024

(54) HAIR REMOVING DEVICE

(71) Applicant: SHENZHEN ULIKE SMART ELECTRONICS CO., LTD., Guangdong (CN)

(72) Inventor: Yuping Pan, Guangdong (CN)

(73) Assignee: SHENZHEN ULIKE SMART ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 17/970,629

(22) Filed: Oct. 21, 2022

(65) Prior Publication Data

US 2023/0149079 A1 May 18, 2023

Related U.S. Application Data

(63) Continuation of application No. PCT/CN2022/113783, filed on Aug. 19, 2022.

(30) Foreign Application Priority Data

Nov. 15, 2021 (CN) .......................... 202122792654.0
Nov. 15, 2021 (CN) .......................... 202122797614.5
Nov. 15, 2021 (CN) .......................... 202122813851.6

(51) Int. Cl.
*A61B 18/18* (2006.01)
*A45D 26/00* (2006.01)
(Continued)

(52) U.S. Cl.
CPC .......... *A61B 18/18* (2013.01); *A45D 26/0009* (2013.01); *G02B 7/1815* (2013.01);
(Continued)

(58) Field of Classification Search
None
See application file for complete search history.

(56) References Cited

U.S. PATENT DOCUMENTS 10,463,429 B2 * 11/2019 Deem ................ A61B 18/1815
11,419,678 B2 *  8/2022 Deem .................... A61B 18/18
(Continued)

FOREIGN PATENT DOCUMENTS

CN     109027958 A    12/2018
CN     208610984 U     3/2019
(Continued)

OTHER PUBLICATIONS

International Search Report of PCT Patent Application No. PCT/CN2022/113783, dated Nov. 2, 2022.

*Primary Examiner* — Shirley X Jian

(57) ABSTRACT

The present disclosure provides a hair removing device, including: a reflector, a light source, a first light-transmitting body, a heat dissipation base and a refrigerating member. The light source is arranged inside the reflector and can emit light. The reflector can reflect light, such that the hair removing device can emit light to remove the hair from the skin. The first light-transmitting body and the reflector cooperatively define a cavity to receive the light source. A body of the light source is suspended in the cavity. Two sides of the heat dissipation base are thermally coupled to the reflector and the refrigerating member respectively.

20 Claims, 22 Drawing Sheets

(51) Int. Cl.
    *G02B 7/18*        (2021.01)
    *G02B 7/182*     (2021.01)
    *A61B 18/00*     (2006.01)

(52) U.S. Cl.
    CPC ........ *G02B 7/182* (2013.01); *A45D 2026/008* (2013.01); *A61B 2018/00005* (2013.01); *A61B 2018/00476* (2013.01); *A61B 2018/1807* (2013.01)

(56) References Cited

U.S. PATENT DOCUMENTS

| | | | | |
|---|---|---|---|---|
| 2006/0206103 A1* | 9/2006 | Altshuler | ............ | A61B 18/203 606/9 |
| 2006/0271028 A1* | 11/2006 | Altshuler | ............ | A61B 18/203 606/9 |
| 2011/0166559 A1* | 7/2011 | Eckhouse | ............ | A45D 26/00 606/9 |

FOREIGN PATENT DOCUMENTS

| | | |
|---|---|---|
| CN | 211534779 U | 9/2020 |
| CN | 213489243 U | 6/2021 |
| CN | 113144436 A | 7/2021 |
| CN | 213883463 U | 8/2021 |
| CN | 215384556 U | 1/2022 |
| CN | 215534977 U | 1/2022 |
| CN | 216571230 U | 5/2022 |
| CN | 217310568 U | 8/2022 |
| CN | 217488844 U | 9/2022 |
| EP | 0586353 A1 | 3/1994 |
| JP | 2006058686 A | 3/2006 |

* cited by examiner

HAIR REMOVING DEVICE

CROSS REFERENCE TO RELATED APPLICATIONS

The present application is a continuation-application of International (PCT) Patent Application No. PCT/CN2022/113783, filed on Aug. 19, 2022, which claims priority of the Chinese patent application No. 202122792654.0, filed on Nov. 15, 2021, the Chinese patent application No. 202122797614.5, filed on Nov. 15, 2021, and the Chinese patent application No. 202122813851.6, filed on Nov. 15, 2021, the entire contents of which are hereby incorporated by reference in their entireties.

TECHNICAL FIELD

The present disclosure relates to the field of hair removing devices, and in particular to a hair removing device.

BACKGROUND

A hair removing device may generate a large amount of heat while operating. The heat may be generated by a lamp while the lam is operating. The lamp, as a main component of the hair removing device, may generate large amount of heat while operating. If the heat is not dissipated in time, a service life of the lamp may be reduced. At the same time, the heat generated by the lamp may radiate other parts of the hair removing device, such as a component that is configured to contact human skin. If a temperature of the component is high, the user may feel burning when using the device. In addition, the hair removing device in the art may output light unevenly while operating.

Further, while using the hair removing device, it may be difficult to allow a trigger wire to tightly contact the lamp. When the contact between the trigger wire and the lamp is loose, it may be difficult for the trigger wire to trigger the lamp to emit light, and a cost of the trigger wire triggering the lamp to emit light may be increased.

SUMMARY OF THE DISCLOSURE

According to an aspect of the present disclosure, a hair removing device is provided and includes: a reflector, being capable of reflecting light; a light source, arranged inside the reflector and capable of emitting light; a light-transmitting body, having a light incidence surface and a light exiting surface, wherein the light incidence surface is configured to allow the light to enter the light-transmitting body, and the light exiting surface is configured to allow the light to propagate out of the light-transmitting body. The heat dissipation base is disposed on a side of the reflector.

According to an aspect of the present disclosure, a hair removing device is provided and includes: a reflector, being capable of reflecting light; a light source, arranged inside the reflector and capable of emitting light; a first light-transmitting body, arranged on a light exiting side of the reflector, wherein the first light-transmitting body and the reflector cooperatively define a cavity to receive the light source; a heat dissipation base, wherein a side of the heat dissipation base side is thermally coupled to the reflector; a refrigerating member, wherein a refrigerating side of the refrigerating member is thermally coupled to the other side of the heat dissipation base and/or thermally coupled to a side of the reflector; and a bracket, wherein the first light-transmitting body is fixed to the bracket. A body of the light source is suspended in the cavity, and the refrigerating member is configured to cool the cavity.

According to an aspect of the present disclosure, a hair removing device is provided and includes: a reflector, being a conductor and being capable of reflecting light; a light source, being a strip-shaped gas excitation light source, arranged opposite to the reflector, and being configured to be excited by the reflector to emit light after the reflector being conducted; a bracket, wherein the reflector is fixed to the bracket. A distance between a body of the light source and the reflector is greater than zero and less than or equal to 0.3 mm.

BRIEF DESCRIPTION OF THE DRAWINGS

In order to illustrate more clearly the technical solutions in the embodiments of the present disclosure, the accompanying drawings to be used for the description of the embodiments will be briefly described in the following. Apparently, following description shows only some of the embodiments of the present disclosure. Any ordinary skilled person in the art may obtain other drawings without creative work based on the following drawings.

DETAILED DESCRIPTION

In order to allow the above-mentioned objects, features and advantages of the present disclosure to be more obvious and comprehensible, technical solutions of the embodiments of the present disclosure will be clearly and completely described below by referring to the accompanying drawings in the embodiments of the present disclosure. It shall be understood that the specific embodiments described herein are intended to explain the present disclosure only and are not intended to limit the present disclosure. To be noted that, for the purpose of description, the accompanying drawings show only part, but not all, of the structures relevant to the present disclosure. Any ordinary skilled person in the art shall obtain all other embodiments based on the embodiments in the present disclosure without creative work, and the obtained embodiments shall be within the scope of the present disclosure.

Terms "first", "second" and the like in the present disclosure are used for distinguishing objects, instead of defining a certain sequence. In addition, terms "includes", "has", and any variations thereof, are intended to cover non-exclusive inclusion. For example, a process, a method, a system, a product or an apparatus including a series of operations or units is not limited to the listed operations or units, but may further include operations or units that are not listed, or other operations or units that are inherent to the process, the method, the product, or the apparatus.

An "embodiment" of the present disclosure means that a particular feature, a structure, or a property described one embodiment may be included in at least one other embodiments of the present disclosure. The presence of the term at various sections in the specification does not necessarily mean a same embodiment or a separate or an alternative embodiment that is mutually exclusive with other embodiments. Names and labels of various elements and structures are used to indicate features, structures or properties of each embodiment by referring to the accompanying drawings and do not influence substantive meanings of the elements. Names and labels of different embodiments shall be interpreted independently. Any ordinary skilled person in the art shall explicitly and implicitly understand that the embodiments described herein may be combined with other embodiments. Names the various elements, structures, and so on, in the embodiments are exemplary and does not limit substantive meanings of the elements. Other names may be used or the names may be equivalently transformed, as long as the functional and substantive meanings of the elements remain unchanged. Therefore, regardless of the names of the elements, features of the implementation shall be equivalently fallen within the scope of the present disclosure.

Figure 1:
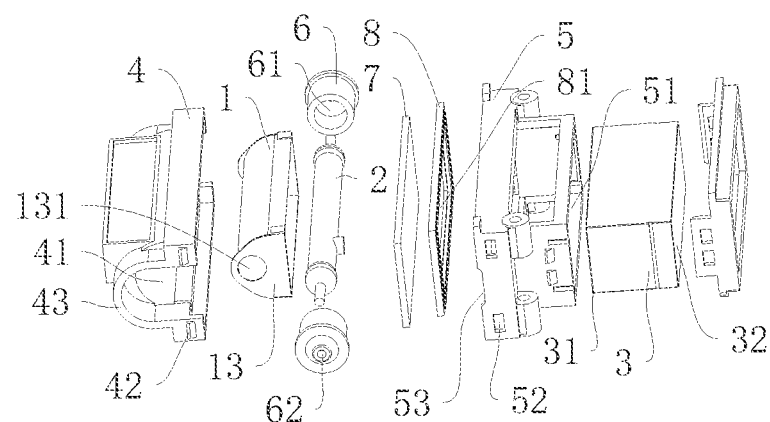
FIG. 1 is an exploded view showing the entire structure of the device according to an embodiment of the present disclosure.
Figure 2:
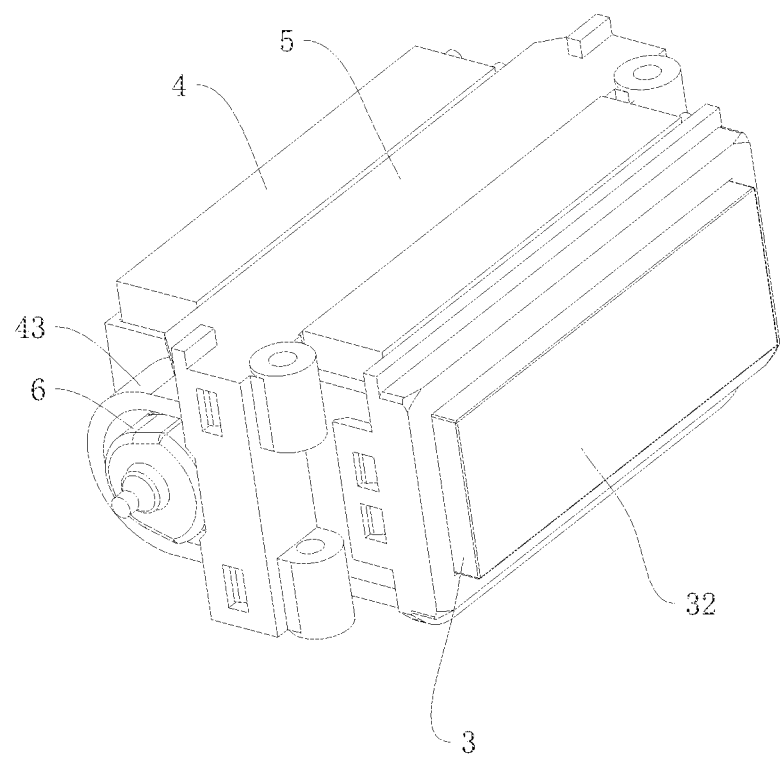
FIG. 2 is an assembled view showing the entire structure of the device according to an embodiment of the present disclosure.

As shown in FIG. 1 and FIG. 2, a hair removing device is provided and includes a reflector 1, a light source 2 and a light-transmitting body 3. The light source 2 is received in the reflector 1 and may emit light. The reflector 1 may reflect the light emitted by the light source 2. The light-transmitting body 3 has a light incidence surface 31, which allows the light to enter an inside of the light-transmitting body 3, and a light exiting surface 32, which allows the light inside the light-transmitting body 3 to propagate out of the light-transmitting body 3. The light emitted from the light source 2 may be reflected by the reflector 1 and emitted evenly from the light exiting surface 32 of the light-transmitting body 3. Therefore, uniformity of the light exiting surface outputting the light may be improved, and a hair removing effect may be improved.

In some embodiments, structures and relative positions of the light source 2, the reflector 1 and the light-transmitting body 3 may satisfy the following. The uniformity of the light exiting surface outputting the light may be greater than or equal to 90%, or light spots on the light exiting surface 32 occupies at least 95% of the area of the light exiting surface 32. When the uniformity of the light exiting surface 32 outputting the light is greater than or equal to 90%, the hair removing effect of the hair removing device may be improved, enabling the hair on the skin to be uniformly removed. Similarly, when the light spots on the light exiting surface 32 occupies at least 95% of the area of the light exiting surface 32, the hair on the skin may be uniformly removed, and utilization of the light may be improved.

When the light exiting surface 32 of the hair removing device outputs the light less uniformly, or when the light spots occupy a relatively small area of the light exiting surface 32, the hair removing device, while in use, may irradiate one position several times to uniformly remove the hair, otherwise the hair may not be removed evenly and the skin may not have a satisfied appearance. For the structures and the relative positions of the light source 2, the reflector 1 and the light-transmitting body 3 in the present disclosure, the uniformity of the light exiting surface 32 outputting the light is greater than or equal to 90%, or the light spots occupy at least 95% of the area of the light exiting surface 32. In this way, the hair removing device does not need to irradiate one position several times. When quality of the light source 2 and a power of the hair removing device is properly configured, and when health of the user is ensured, the hair removing device may irradiate one position once to remove the hair on the one position efficiently and uniformly. At the very least, the number of times that one position of the skin is irradiated repeatedly may be reduced.

In some embodiments, a center of the reflector 1, a center of the light source 2 and a center of the light-transmitting body 3 may locate on a straight line. By adjusting a distance between the centers on the straight line, the uniformity of the light exiting surface 32 outputting the light may be greater than or equal to 90%, or the light spots may occupy at least 95% of the area of the light exiting surface 32. In some embodiments, structures of the reflector 1, the light source 2, the light-transmitting body 3 may be adjusted to allow the hair removing device to meet the above features.

In some embodiments, each of a structure of the reflector 1, a structure of the light source 2 and a structure of the light-transmitting body 3 may be specifically configured to allow the hair removing device to meet the above features. In some embodiments, the structures of the reflector 1, the light source 2 and the light-transmitting body 3, and the relative positions of the reflector 1, the light source 2 and the light-transmitting body 3 may be specifically configured to allow the hair removing device to meet the above features.

In addition, the hair removing device may further include a heat dissipation base 4 and a bracket 5. The heat dissipation base 4 is configured to work cooperatively with the bracket 5 to assemble the reflector 1 with the light-transmitting body 3.

Figure 3:
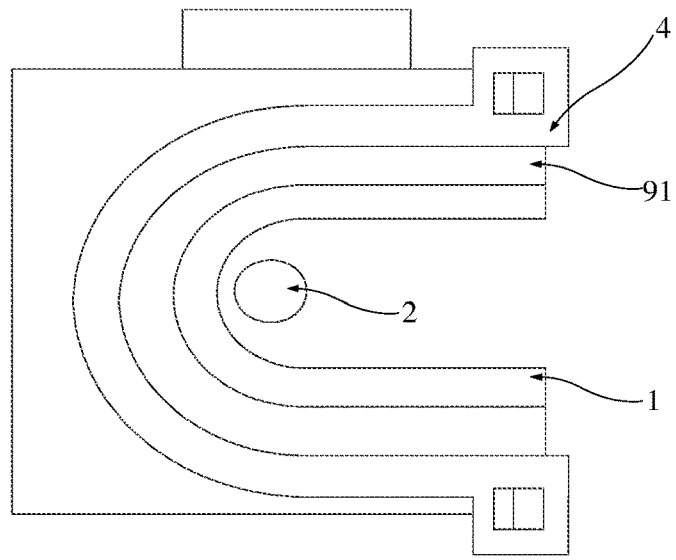
FIG. 3 is a structural schematic view of a carbon-containing layer according to an embodiment of the present disclosure.

In some embodiments, as shown in FIG. 3, the hair removing device may further include a carbon-containing layer 91, arranged in the reflector 1. For example, the carbon-containing layer 91 may be arranged on a side of the reflector 1 away from the light source 2. The light source 2 may generate heat while in use, and the heat may be accumulated in the reflector 1. The carbon-containing layer 91 has excellent thermal conductivity, and therefore, a thermal conducting rate of the reflector 1, which is arranged with the carbon-containing layer 91, may be accelerated, and heat dissipation performance of the reflector 1 may be enhanced. The hair removing device may be prevented from being damaged due to the high temperature, and the skin of the user may be prevented from being irritated or damaged.

In some embodiments, the carbon-containing layer 91 is arranged on the heat dissipation base 4. For example, the carbon-containing layer 91 may be disposed between the heat dissipation base 4 and the reflector 1 to accelerate a thermal conductivity rate between the heat dissipation base 4 and the reflector 1.

In some embodiments, the carbon-containing layer 91 may be arranged on an exposed surface of the heat dissipation base 4 to enhance heat dissipation performance of the heat dissipation base 4.

In some embodiments, the carbon-containing layer 91 may be made of graphene, graphite powders, a graphite sheet, a graphite film, and the like, and may be arranged at any available position as described in the present disclosure by plating, spraying, attaching, and so on.

In some embodiments, the heat dissipation base 4 may be a ceramic base, which may reduce the temperature inside the reflector 1, such that the temperature of the reflector 1 may be controlled, improving the performance of the reflector 1 and allowing the reflector 1 to reflect the light better. When the temperature inside the reflector 1 is not reduced, on one hand, the high temperature may cause damage to the light source 2 and a service life of the light source 2 may be reduced; and on the other hand, the heat may radiate to other components of the hair removing device, especially components that may contact the skin. The high temperature may cause burn the skin of the user, and the hair removing device may not be used conveniently. In the present disclosure, the ceramic base may reduce the temperature inside the reflector 1, and the heat inside the reflector 1 may be dissipated by any one or a combination of heat transferring, heat convection and heat radiation. In this way, the temperature inside the reflector 1 may be reduced, such that the heat of the light source 2 may be dissipated evenly, and the heat dissipation efficiency of the hair removing device may be improved.

In some embodiments, a groove body 41 is arranged on a side of the heat dissipation base 4. The groove body 41 may be strip shaped. The reflector 1 may be embedded in the groove body 41. The bracket 5 defines a window 51. The window 51 may be squared or in any other shape, as long as the shape of the window 51 matches a shape of the light-transmitting body 3. The light-transmitting body 3 may be embedded in the window 51. The light-transmitting body 3 may be disposed on a side of the reflector 1 that defines an opening. The heat dissipation base 4 and the bracket 5 may be detachably connected, such that the hair removing device may be assembled and disassembled easily.

In some embodiments, each of two sides of the heat dissipation base 4 is arranged with a first fastening portion 42, and the first fastening portion 42 and the heat dissipation base 4 may be configured as an integral one-piece structure. Each of two sides of the bracket 5 is arranged with a second fastening portion 52, and the second fastening portion 52 and the bracket 5 may be configured as an integral one-piece structure. The first fastening portion 42 may correspond to the second fastening portion 52. In the process of connecting the heat dissipation base 4 with the bracket 5, the first fastening portion 42 may be tightly fastened with the second fastening portion 52. In this way, the heat dissipation base 4 and the bracket 5 may be connected together stably, enhancing stability of the hair removing device.

In some embodiments, the first fastening portion 42 may be a buckle block or a cantilever hook, and the second fastening portion 52 may be a mounting hole. While connecting the heat dissipation base 4 with the bracket 5, the cantilever hook may be received into the mounting hole. Further, after the cantilever hook is received in the mounting hole, a wall of the mounting hole may restrict the cantilever hook, preventing the cantilever hook from easily leaving out of the mounting hole. In this way, the first fastening portion 42 and the second fastening portion 52 may be stably connected, i.e., the heat dissipation base 4 and the bracket 5 may be fixed with each other, effectively preventing the heat dissipation base 4 from being loosed from or falling off from the bracket 5.

In some embodiments, the light-transmitting body 3 may be a crystal.

Figure 4:
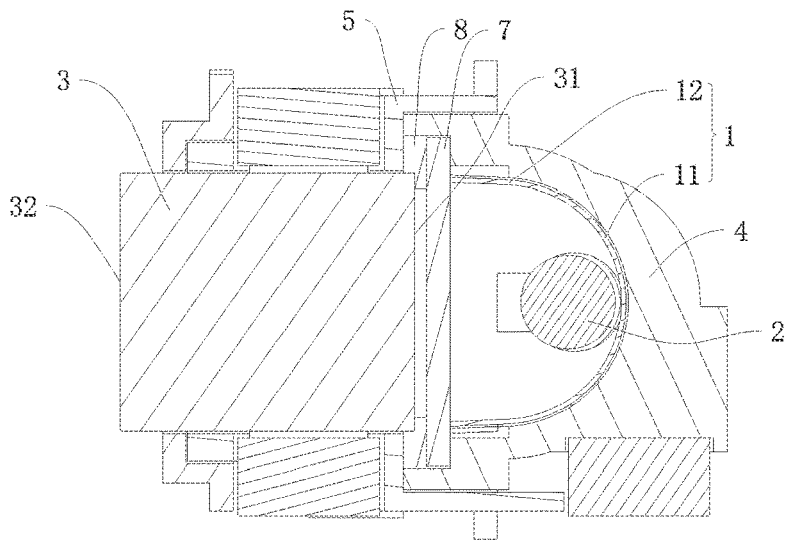
FIG. 4 is a cross sectional view showing the entire structure of the device according to an embodiment of the present disclosure.

As shown in FIG. 1, FIG. 2 and FIG. 4, the reflector 1 has a first reflective region 11 and a second reflective region 12. The first reflective region 11 is a curved region including a bottom of the reflector 1, and the second reflective region 12 is two flat regions extending outwards from two ends of the curved region. The flat region may be tangential to the curved region. After the light source 2 emits light, the reflector 1 reflects the light to the light-transmitting body 3.

In some embodiments, the reflector 1 may be a semi-arc reflector 1. The light source 2 may be a strip-shaped lamp. The strip-shaped lamp emits light, and the curved region of the reflector 1 may reflect the light to the light-transmitting body 3. In addition, the flat regions of the reflector 1 may also reflect the light to the light-transmitting body 3. The light may be reflected adequately by the curved region and the flat regions, such that a light emission rate may be improved, and utilization of the light may be improved.

In some embodiments, the reflector 1 may be strip shaped.

Figure 5:
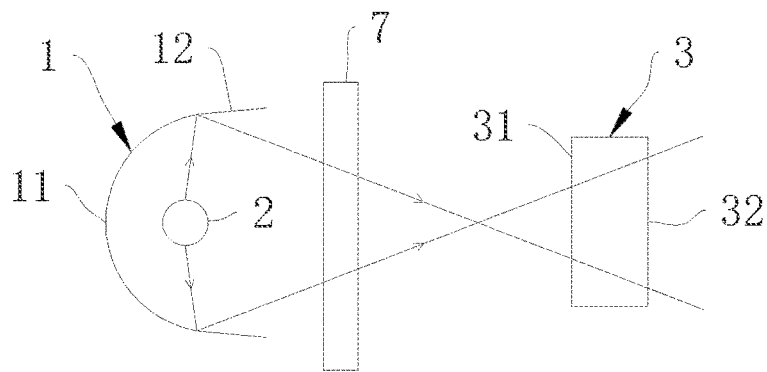
FIG. 5 shows a light propagating path according to an embodiment of the present disclosure.

As shown in FIG. 5, in some embodiments, a center of the light source 2 is located between a focal point of the reflector 1 and the bottom of the reflector 1. The light incidence surface 31 of the light-transmitting body 3 is disposed between the light exiting surface 32 and the focal point of the reflector 1. Further, the light reflected from the reflector 1 may be focused at a position between the light exiting surface 32 of the light-transmitting body 3 and the focal point of the reflector 1. By configuring positions of the light source 2, the reflector 1 and the light-transmitting body 3, the uniformity of the light exiting surface outputting the light may be greater than or equal to 90%, or light spots on the light exiting surface 32 occupies at least 95% of the area of the light exiting surface 32. In this way, the light emitted by the light source 2 may be fully reflected by the reflector 1 to reach the light-transmitting body 3, improving the uniformity that the light-transmitting body 3 outputs the light.

For example, when the hair removing device is operating, the light source 2 emits light, the first reflective region 11 and the second reflective regions 12 of the reflector 1 may fully reflect the light onto the light-transmitting body 3. The light enters the light-transmitting body 3 from the light incident surface, and afterwards, the light exits the light-transmitting body 3 from the light exiting surface, such that the uniformity of the light exiting surface outputting the light may be greater than or equal to 90%, or light spots on the light exiting surface 32 occupies at least 95% of the area of the light exiting surface 32. In this way, the uniformity that the hair removing device outputs the light may be improved, and the hair removing effect of the hair removing device may be improved.

In some embodiments, an angle between the flat region and a reference line may be between 5 and 20 degrees. The reference line may be a line between the center of the light source 2 and the center of the light-transmitting body 3. By configuring the angle between the flat region and the reference line, the light may be fully reflected onto the light-transmitting body 3. On one hand, the waste of the light may be reduced, a usage cost may be reduced. On the other hand, the uniformity that the light-transmitting body 3 outputs the light may be improved.

For the hair removing device in another embodiment of the present disclosure, the light source 2 is disposed near the bottom of the reflector 1, and the reflector 1 does not have the flat region, which is having an angle of between 5 and 20 degrees relative to the reference line. In this case, it is highly likely that the light may be reflected for a plurality of times. Due to an angle of light incidence, a possibility that the light may be reflected for a plurality of times may be increased, and a light exiting angle may be disorganized and may not be controlled easily.

By defining the angle between the flat region and the reference line, when the light is emitted from the reflector 1, a better light exiting angle may be obtained, and the light may be distributed more convergently. In this way, a light emission rate may be improved, effectively avoiding light loss and improving a light distribution effect.

Further, the angle between the flat region and the reference line may be between 8 and 15 degrees. The angle between the flat region and the reference line may be 8 degrees. Alternatively, the angle between the flat region and the reference line may be 15 degrees. For example, in the above range, the focal point may be closer. When conditions about the light uniformity and the light utilization are satisfied, the light-transmitting body 3 may be closer to the light source 2, such that the hair removing device may have a more compact structure, and material for making the hair removing device may be saved.

The angle between the flat region and the reference line may be between 8 and 15 degrees to allow the focal point to be closer, the light-transmitting body 3 may be disposed closer to the light source 2, and the uniformity that the hair removing device outputs the light may be higher. The uniformity that the hair removing device outputs the light may be improved by configuring the structure of the device, without increasing a light intensity or the like. In this configuration, the light-transmitting body 3 is closer to the light source 2. The entire hair removing device may be configured to be smaller and have a more compact structure, and may be easily carried and used.

As shown in FIG. 1, each of two ends of the reflector 1 along a length direction of the reflector 1 is arranged with a side reflecting member 13. The side reflecting member 13 and the reflector 1 are configured as an integral one-piece structure. The side reflecting member 13 is a sheet and may reflect light, which escapes from the two ends of the reflector 1, onto the light-transmitting body 3. The side reflecting member 13 defines a through hole 131, and two side reflecting members 13 at the two ends may define two through holes 131. The two through holes 131 have a same center line. An end of the light source 2 passes through the through hole 131.

In some embodiments, a fixing member 6 is connected each of two ends of the light source 2 to movably fix the light source 2 to the reflector 1. For example, the fixing member 6 may be a silicone soft cover. The fixing member 6 may alternatively be a rubber cover. The fixing member 6 may be cylindrical. The fixing member 6 may define a mounting slot 61. Each of two ends of the light source is embedded in the mounting slot 61. The fixing member 6 defines a fixing hole 62 along an axis of the fixing member 62. The fixing hole 62 is communicated with the mounting slot 61. Each of the two ends of the light source is arranged with a mounting post extending from the light source. The mounting post may extend through the fixing hole 62. The fixing member 6 may be arranged at an outside of the reflector 1.

In some embodiments, a support block 43 is arranged at each of two ends of the heat dissipation base 4, and the support block 43 and the heat dissipation base 4 may be configured as an integral one-piece structure. The support block 43 defines a gap. Each of the two ends of the light source 2 and a corresponding fixing member 6 may be received in the gap. When the heat dissipation base 4 and the bracket 5 are fastened, the bracket 5 and the support block 43 may fix the fixing member 6, such that the light source 2 may be fixed on the reflector 1. The fixing member 6 itself may be elastic. While the bracket 5 and the support block 43 are fixing the fixing member 6, when the fixing member 6 is compressed, a shape of the fixing member 6 may be changed correspondingly to adapt to a shape of the gap. In addition, a compression force applied to the light source may be optimally reduced, reducing damage to the light source.

In some embodiments, a side wall of the bracket 5 near the fixing member 6 is arranged with a limiting portion 53, configured to limit a position of the fixing member 6. The limiting portion 53 may be projections, which are spaced apart from each other, or a notch. A wall of the notch may be curved. By configuring the limiting portion 53, the support block 43 and the bracket 5 stably fix the fixing member 6, optimally preventing the fixing member 6 from being loosed, and improving the stability of the hair removing device.

As shown in FIG. 1, a filter 7 is disposed between the light-transmitting body 3 and the reflector 1 and is configured to filter the light. The filter 7 is fixed with the bracket 5 and covers the window 51. In addition, when the filter 7 covers an opening of the reflector 1 facing the bracket 5, the filter 7 is fixed relative to the heat dissipation base 4. When the heat dissipation base 4 is fastened to the bracket 5, a side wall of the bracket 5 near the reflector 1 abuts against a side of the filter 7, and another side of the filter 7 abuts against the reflector 1. The filter 7 may filter harmful light out of UV rays, reducing damages to the human body, such that safety of the hair removing device may be improved, and the hair removing effect may be improved.

In some embodiments, a pad 8 is disposed between the bracket 5 and the filter 7. A shape of the pad 8 may be similar to a shape of the filter 7. The pad 8 may be sheet-shaped and may define a clearance opening 81 that allows the light to pass through. A size of the clearance opening 81 is smaller than a size of a side wall of the light-transmitting body 3 facing the pad 8. When the heat dissipation base 4 is fastened with the bracket 5, the light-transmitting body 3 abuts against a side of the pad 8, and the other side of the pad 8 abuts against the filter 7. The pad 8 may reduce a pressure that the light-transmitting body 3 applies on the filter 7 and reduce collision between the light-transmitting body 3 and the filter 7. In this way, production costs may be reduced optimally, and a service life of the filter 7 may be increased.

Figure 11:
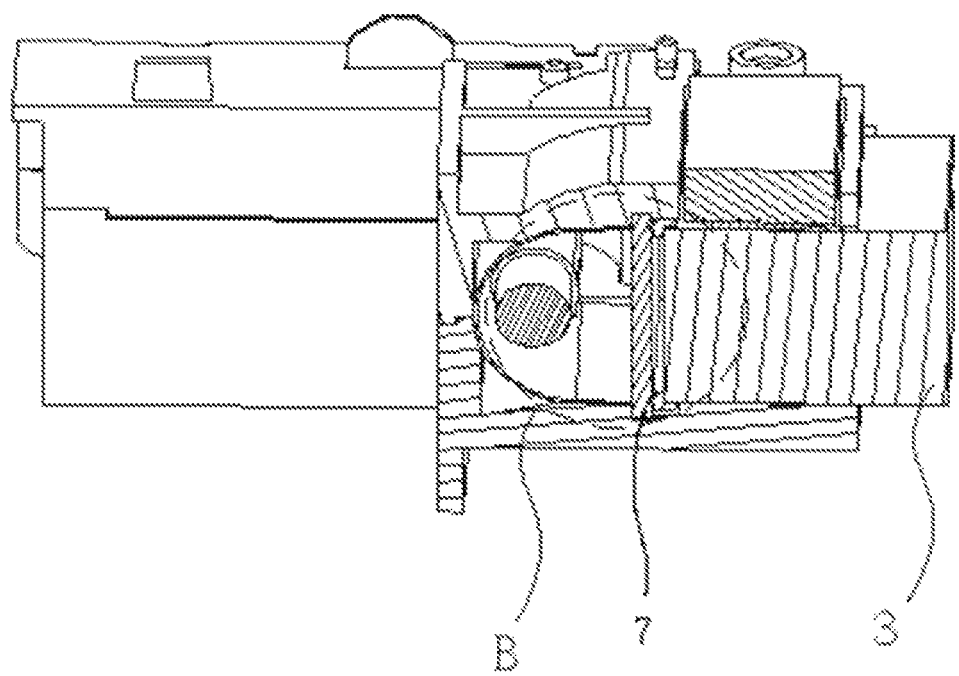
FIG. 11 is a cross sectional view showing the entire structure of the device according to another embodiment of the present disclosure.
Figure 12:
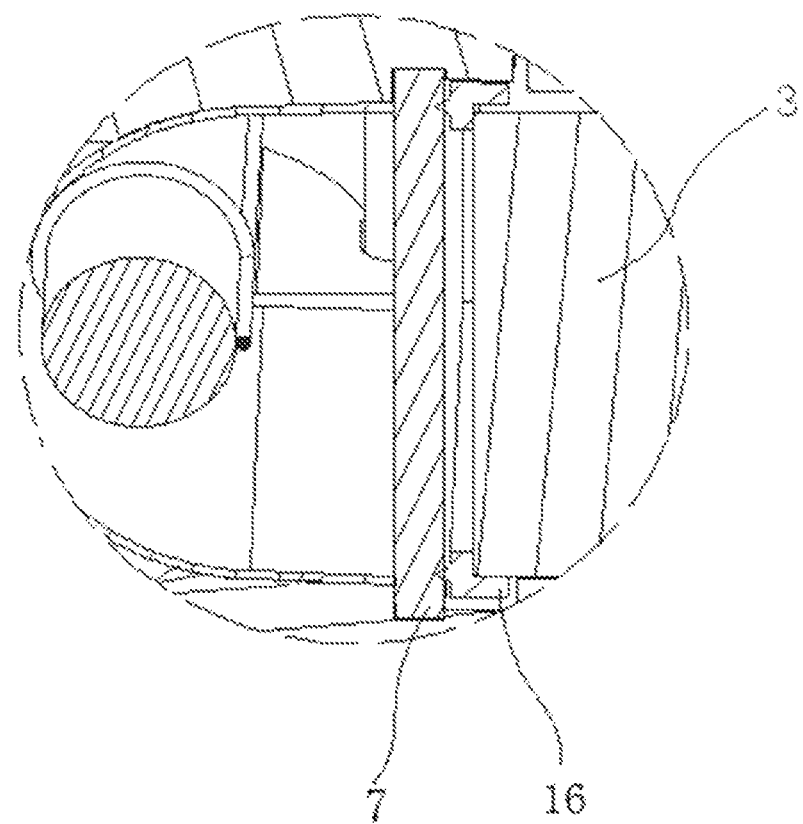
FIG. 12 is an enlarged view of a portion B shown in FIG. 11.

As shown in FIG. 11 and FIG. 12, for the hair removing device in another embodiment, an elastic seal ring 16 is disposed between the filter 7 and the light-transmitting body 3. The elastic seal ring 16 may be ring-shaped. The filter 7 and the light-transmitting body 3 may be sealed with the elastic seal ring 16. In this way, water condensation may not be generated between the light-transmitting body 3 and the filter 7. Dirt may not penetrate into the connection between the light-transmitting body 3 and the filter 7. The elastic seal ring 16 may be preferably ring-shaped.

Of course, when the hair removing device falls to the ground, the light-transmitting body 3 may rigidly collide with the ground. A conventional light-transmitting body 3 may transfer a colliding impact to the filter 7, such that the filter 7, the reflector 1 and the light source 2 may be vibrated and damaged. For the hair removing device in the present embodiment, when the light-transmitting body 3 is collided, the impact force may be eliminated by the elastic seal ring 16. Due to the elasticity of the elastic seal ring 16, the elastic seal ring 16 may be elastically deformed when being compressed by external forces, reducing or eliminating the impact between the filter 7 and the light-transmitting body 3, and reducing a possibility that the filter 7, the reflector 1 and the light source 2 are broken by the impact force. Therefore, anti-collision performance of the hair removing device may be enhanced.

Figure 13:
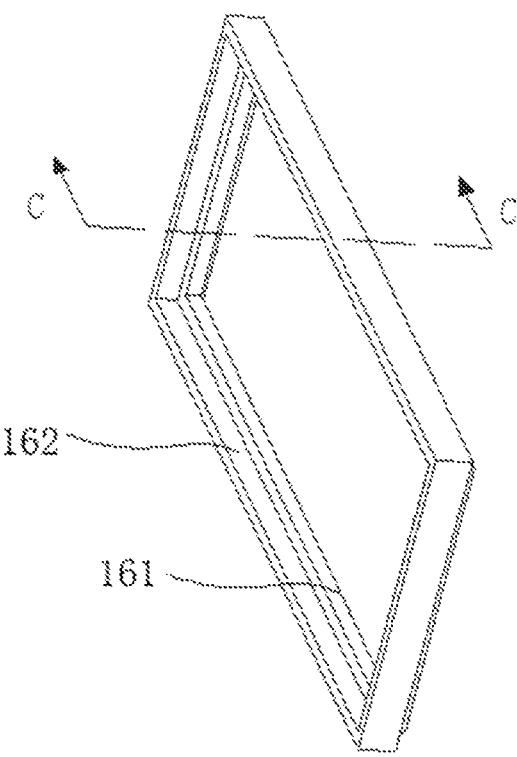
FIG. 13 is a structural schematic view of an elastic seal ring according to an embodiment of the present disclosure.
Figure 14:
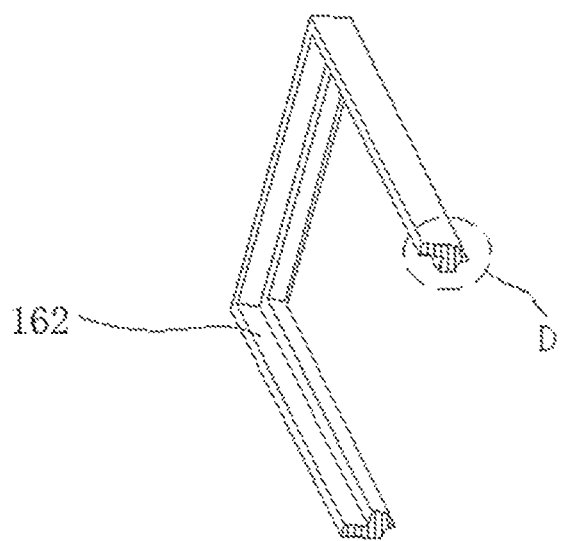
FIG. 14 is a cross sectional view of the embodiments shown in FIG. 13 by taking along the line C-C.
Figure 15:
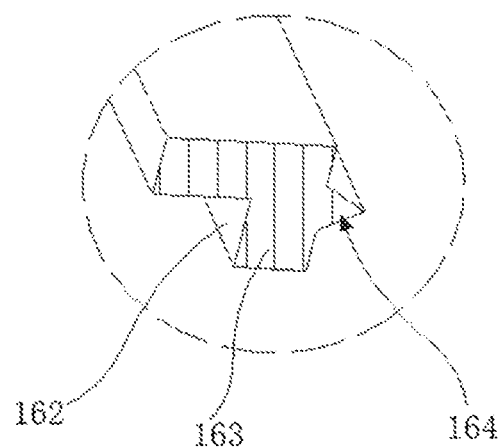
FIG. 15 is an enlarged view of a portion D shown in FIG. 14.

As shown in FIGS. 13 to 15, the elastic seal ring 16 has an inner ring 161 that allows the light to pass through. The light, after being filtered by the filter 7, may be guided to the light-transmitting body 3 through the inner ring 161 and further irradiate the skin of the user.

In the present embodiment, the filter 7 and the light-transmitting body 3 may be fixed directly to the bracket 5. The filter 7 and the light-transmitting body 3 cannot be moved relative to the bracket 5. Therefore, while the hair removing device is being used, the light-transmitting body 3 may be prevented from shifting back relative to bracket 5 caused by a human bone or a sharp object abutting against the light-transmitting body 3, and the filter 7 or a hair removing assembly 100 may be prevented from being irrecoverably deformed due to compression. The elastic seal ring 16 may be irrecoverably deformed when being compressed for a plurality of times. In this way, a light guiding effect of the hair removing device may not be affected, and the waste of the light energy may be avoided.

The elastic seal ring 16 further defines a mounting groove 162 communicated with an opening of the inner ring 161. The mounting groove 162 is defined in a side of the elastic seal ring 16 away from the hair removing assembly 100. The inner ring 161 extends from a bottom wall of the mounting groove 162 towards the filter 7. The light-transmitting body 3 is partially received in the mounting groove 162 to improve a sealing effect between the light-transmitting body 3 and the elastic seal ring 16, and further to fix the elastic seal ring 16 to the light-transmitting body 3 to achieve fixed connection between the elastic seal ring 16 and the light-transmitting body 3.

In some embodiments, the elastic seal ring 16 may include an outer ring 163 and a projection 164 arranged on a side of the outer ring 163. The projection 164 may abut against the filter 7. A side of the outer ring 163 away from the projection 164 defines the mounting groove 162. The inner ring 161 extends from the bottom wall of the mounting groove 162 towards the projection 164. Each of the outer ring 163 and the projection 164 may be a complete closed-loop structure. The light inside the inner ring 161 may only be emitted outwardly from the light-transmitting body 3.

In some embodiments, a cross section of the projection 164 may be a triangle that is arranged transversely. A contact area between the projection 164 and the filter 7 may be less than a contact area between the projection 164 and the outer ring 163. Therefore, when the elastic seal ring 16 is arranged, an end of the projection 164 away from the outer ring 163 may be partially curled after being compressed. Since the elastic seal ring 16 is elastic, a curled part of the elastic seal ring 16 may tightly abut against the filter 7. That is, when a distance between the light-transmitting body 3 and the filter 7 changes slightly, the elastic seal ring 16 may be adjusted by taking the curled part to be adaptive to the change in the distance. In this way, tight or even interference fit between the elastic seal ring 16 and the light-transmitting body 3 and between the elastic seal ring 16 and the filter may be maintained at all times, and a better sealing effect may be achieved. In other embodiments, the cross section of the projection 164 may be trapezoidal.

In the present embodiment, the elastic seal ring 16 may be a ring, made of laser resistant, high temperature resistant and low temperature resistant material, such that when the elastic seal ring 16 is being used, the elastic seal ring 16 may be prevented from being deformed due to high or low temperatures or laser exposure, increasing a service life of the elastic seal ring 16.

According to the present disclosure, a hair removing device is provided. The hair removing device may include the reflector 1, the light source 2 and the light-transmitting body 3. The light source 2 emits light, and the light emitted from the light source 2 may be reflected by the reflector 1, allowing the light to enter the light-transmitting body 3 from the light incidence surface 31 of the light-transmitting body 3 and to exit the light-transmitting body 3 from the light exiting surface 32 of the light-transmitting body 3. Further, structures and relative positions of the light source 2, the reflector 1 and the light-transmitting body 3 may satisfy the following. The uniformity of the light exiting surface outputting the light may be greater than or equal to 90%, or light spots on the light exiting surface 32 occupies at least 95% of the area of the light exiting surface 32. By configuring the structures and relative positions of the light source 2, the reflector 1 and the light-transmitting body 3, the light may be evenly emitted out of the light exiting surface 32 of the light-transmitting body 3, such that the uniformity that the hair removing device outputs the light may be improved, and the hair removing effect of the device may be improved.

As shown in FIG. 5, FIG. 5 is a schematic structural view of the hair removing device according to another embodiment of the present disclosure. The hair removing device may include a head portion 111 and a hand-held portion 112 connected to the head portion 111. The head portion 111 is arranged with a cold-compressing portion 1111, configured to attach to the skin. The cold-compressing portion 1111 may emit light to irradiate a hair follicle of the skin. The light may penetrate the skin to irradiate the hair follicle to remove the hair. In addition, the cold-compressing portion 1111 may quickly cool down the skin to reduce burning to the skin caused by the light. In this way, while using the hair removing device, the user may not be discomfortable. In some embodiments, the cold-compressing portion 1111 may emit light for skin care, such that the hair removing device may remove hair and perform skin care at the same time.

In some embodiments, the hand-held portion 112 may include a housing defining a space in a middle (not marked in the drawings). A surface of the housing may define an air vent 1211. The air vent 1211 may be communicated with an inside of the housing and an outside of the housing, such that the hair removing device may exchange air with the outside through the air vent 1211, and a temperature inside the device may be reduced. The housing may further include an interface 1212 configured to connect to an external power supply for charging the hair removing device. A position where the interface 1212 is arranged on the housing is not limited by the present disclosure.

Figure 6:
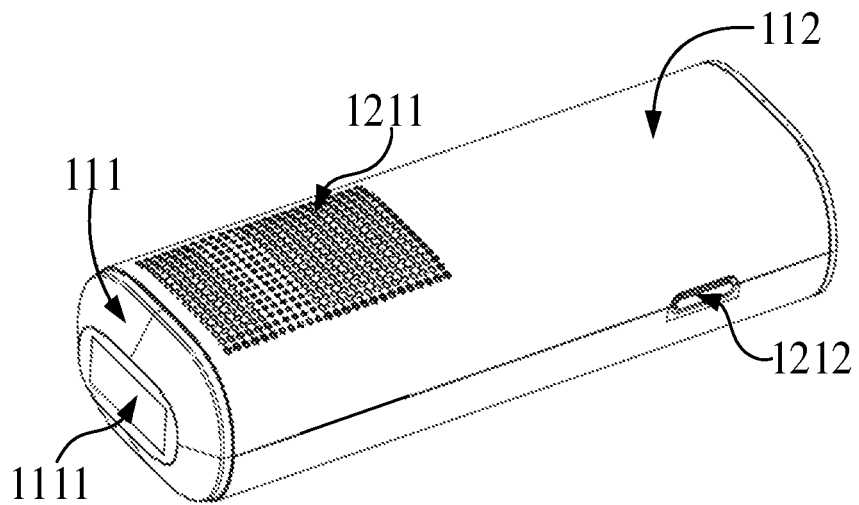
FIG. 6 is a structural schematic view of the device according to an embodiment of the present disclosure.
Figure 7:
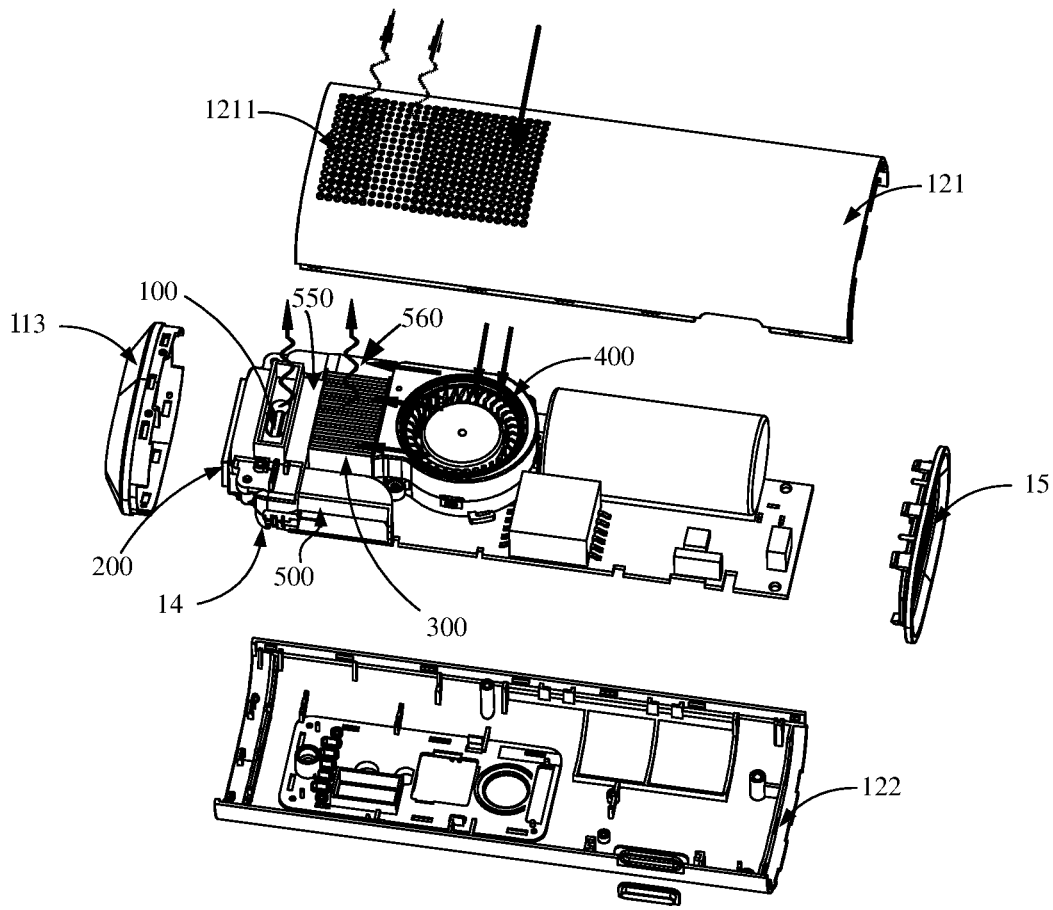
FIG. 7 is an exploded view of the device according to an embodiment of the present disclosure.

As shown in FIG. 6 and FIG. 7, FIG. 7 is an exploded view of the device according to an embodiment of the present disclosure. An arrow in FIG. 7 shows a direction of airflow inside the hair removing device driven by a cold drive assembly. A straight line represents a direction which cold air flows along, and a wavy line represents a direction which hot air flows along. In detail, the hair removing device may include the housing, a light cover 113 arranged over an opening of the housing, a hair removing mechanism 14 received inside the housing and a bottom cover 15.

In the present embodiment, the housing may include a first housing 121 and a second housing 122. The first housing 121 and the second housing 122 may be snapped with each other to define a cavity and two openings at two ends of the housing. The hair removing mechanism 14 is received in the cavity, the light cover 113 and the bottom cover 15 are arranged to cover the two openings respectively to encapsulate the openings defined by the first housing 121 and the second housing 122 after the first housing 121 and the second housing 122 are snapped with each other to define the cavity.

In some embodiments, the first housing 121, the second housing 122, the light cover 113 and the bottom cover 15 may be connected by snaps, screws, bonding, and so on.

The hair removing mechanism 14 may include the hair removing assembly 100, a cold compressing assembly 200, a heat dissipation base 300 and the cold drive assembly 400.

The cold compressing assembly 200 is arranged near the light cover 113. The light cover 113 may define a through hole (not marked in the drawings). A part of the cold compressing assembly 200 is exposed to the outside of the housing through the through hole in the light cover 113 to directly contact the skin. It shall be understood that the part of the cold compressing assembly 200 and the light cover 113 form the head portion 111 of the hair removing device.

The hair removing assembly 100 is arranged on a side of the cold compressing assembly 200 away from the light cover 113 and is configured to emit light to the cold compressing assembly 200. The light may be visible light, such as red light, green light or yellow light. After the light enters the cold compressing assembly 200, the light may pass through the cold compressing assembly 200 to further penetrate the skin to reach the hair follicle under the skin to remove hair.

The heat dissipation base 300 is arranged on a side of the cold compressing assembly 200 and is connected to the cold compressing assembly 200. The cold compressing assembly 200 is able to absorb heat from the skin when attaching to the skin to reduce the temperature of the skin and reduce the burning. A temperature of the cold compressing assembly 200 may be increased when being used for a long period of time, and a cooling effect may be reduced. The heat dissipation base 300 may absorb the heat of the cold compressing assembly 200, such that the cold compressing assembly 200 may keep operating at a low temperature, ensuring the cooling effect that the cold compressing assembly 200 cools the skin. Therefore, the hair removing device in the present embodiment is able to operate constantly at a low temperature when being used continuously, and the user may not hurt.

The cold drive assembly 400 is arranged on a side of at least a part of the heat dissipation base 300 facing away from the hair removing assembly 100 and is configured to dissipate heat from the hair removing assembly 100 and the heat dissipation base 300.

In the present embodiment, the cold drive assembly 400 may absorb an external cooling medium, which passes through the air vent 1211 to enter the inside of the hair removing device. The cooling medium may flow along the hair removing assembly 100 and the heat dissipation base 300 to remove the heat and further flow out of the device through the air vent 1211.

In some embodiments, the external cooling medium may be air. The cold drive assembly 400 may absorb the air and blows the air towards the hair removing assembly 100 and the heat dissipation base 300. Heat of the hair removing assembly 100 and the heat dissipation base 300 may be removed by the airflow.

In the present embodiment, the air vent 1211 may be defined in the first housing 121, and at least part of the cold drive assembly 400 is opposite to the air vent 1211, such that the cold drive assembly 400 may better absorb the external cooling medium, which enters the housing through the air vent 1211, and a heat dissipation efficiency may be improved. In other embodiments, the air vent 1211 may be defined in the second housing 122.

Figure 8:
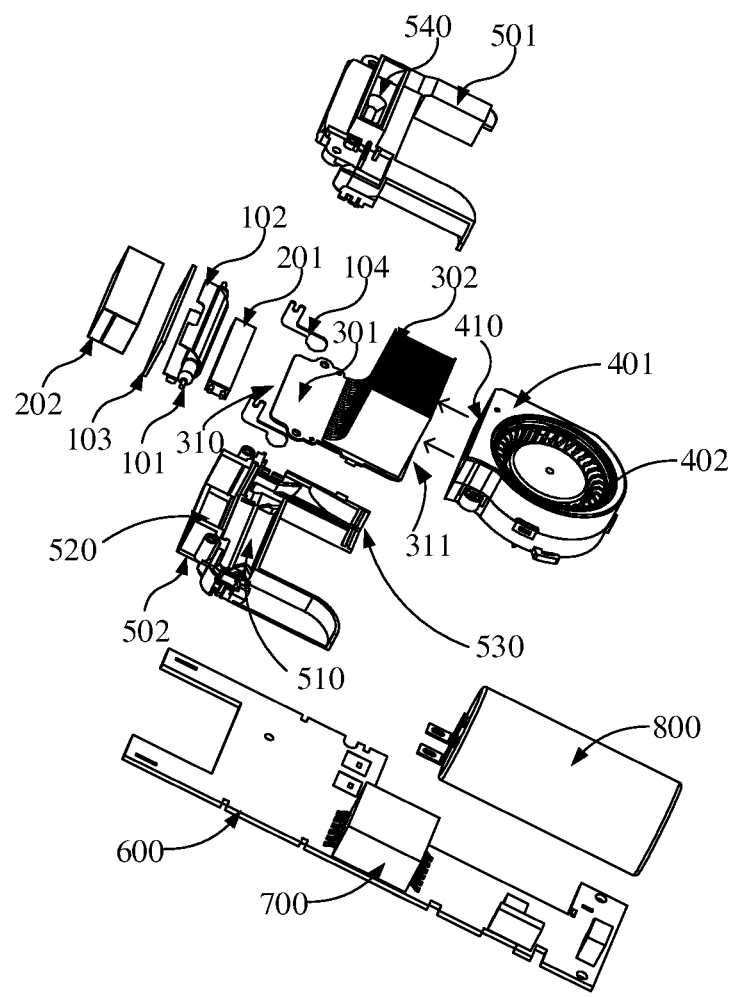
FIG. 8 is an exploded view of the embodiment shown in FIG. 7.
Figure 9:
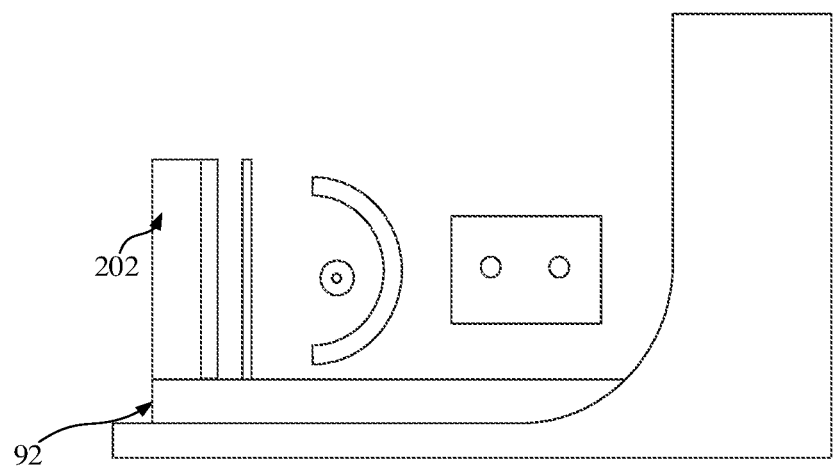
FIG. 9 is a structural schematic view of a carbon-containing layer according to another embodiment of the present disclosure.

As shown in FIG. 7 and FIG. 8, FIG. 8 is an exploded view of the structure shown in FIG. 7, arrows in FIG. 8 may indicate a direction that air is blown out of a fan.

In the present embodiment, the hair removing device may further include a bracket 500, a circuit board 600, a processor 700 and a capacitor 800. The hair removing assembly 100 and the cold compressing assembly 200 may be arranged inside the bracket 500, and the cold drive assembly 400 may be arranged adjacent to the bracket 500. The hair removing assembly 100, the cold compressing assembly 200 and the cold drive assembly 400 may be mounted on and electrically connected to the circuit board 600.

The processor 700 and capacitor 800 may be electrically connected to and arranged on the circuit board 600. When an external power supply is connected, the external power supply may charge the capacitor 800, such that the capacitor 800 may provide power for the hair removing device. Further, the capacitor 800 may store power when being connected to the external power supply, such that the hair removing device may be used when being not connected to the external power supply. The processor 700 may send control commands to the hair removing assembly 100, the cold compressing assembly 200 and the cold drive assembly 400 to control operation of the hair removing device. For example, the hair removing device may be controlled to be switched on and off, thermal protection of the hair removing device may be controlled, a power of the hair removing device may be adjusted, and so on.

In the present embodiment, the circuit board 600 may be fixed in the second housing 122, and the circuit board 600 may be a PCBA circuit board.

In the art, heat inside the hair removing device may be continuously increased while being used. Circuits and components inside the hair removing device may be exploded, burned, short-circuited, and so on, when being operating at a high temperature. In the present embodiment, the cold drive assembly 400 may dissipate heat from the hair removing assembly 100 and the heat dissipation base 300, and the heat dissipation base 300 may dissipate heat from the cold compressing assembly 200, such that the cold compressing assembly 200 may compress the skin to cool the skin, allowing the skin to feel comfortable, and preventing the components from being exploded, burned, short-circuited, and so on.

In detail, the hair removing assembly 100 may include a light source 101, a reflector 102, a filter 103 and two electrodes 104.

The light source 101, the reflector 102 and the filter 103 are arranged inside the bracket 500, i.e., the bracket 500 is configured with mounting positions for the light source 101, the reflector 102 and the filter 103. The light source 101, the reflector 102 and the filter 103 may be snap into the mounting positions in the bracket 500, correspondingly.

The light source 101 may be opposite to the cold compressing assembly 200. The light emitted from the light source 101 may be directly injected into the cold compressing assembly 200. The reflector 102 may be disposed on a side of the light source 101 away from the cold compressing assembly 200 and may reflect the light of the light source 101 into the cold compressing assembly 200 to prevent a loss of light energy. The filter 103 is disposed between the light source 101 and the cold compressing assembly 200. That is, the light source 101, the filter 103 and the cold compressing assembly 200 may be disposed sequentially in a direction of light propagation. The filter 103 is configured to filter some harmful light out of the light emitted from the light source 101, such that damages to the skin by the light may be reduced, and safety of hair removing may be increased. The two electrodes 104 may be connected on two sides of the light source 101 and may be electrically connected to the circuit board 600 for transmitting electrical signals.

In some embodiments, the light source 101 may be a lamp, a colour of the light emitted by the lamp may not be limited. The lamp may emit coloured light, composite light, and so on. A wavelength and a frequency of the light may be determined based on demands. A type of the lamp is not limited. The lamp may be a xenon semiconductor lamp, a quartz lamp, a laser lamp, and so on. A type of the light may be intense pulse light (IPL), delicate pulse light (DPL), an optimal pulse technology (OPT), an advanced optimal pulse technology (AOPT), broadband light (BBL), and so on. The type of the light may be determined based on desired effects.

In some embodiments, the reflector 102 may be a U-shaped reflector that surrounds the light source 101. Further, an opening of the U-shaped reflector may face the cold compressing assembly 200, and reflect light that does not enter the cold compressing assembly 200 to the cold compressing assembly 200. In addition, the reflector 102 may prevent the heat generated by the light source 101 from transferring to other components of the hair removing device. In the present embodiment, the bracket 500 may include a fixing frame 550 and a tube 560. The fixing frame 550 may define a first receiving space 510 and a second receiving space 520. The first receiving space 510 is configured for receiving the hair removing assembly 100. The second receiving space 520 is configured for receiving the cold compressing assembly 200. The first receiving space 510 may be adjacent to the second receiving space 520 to reduce a distance between the hair removing assembly 100 and the cold compressing assembly 200, reducing a loss of the light emitted from the hair removing assembly 100. The second receiving space 520 may be closer to the head portion 111 of the hair removing device shown in FIG. 6, compared to the first receiving space 510. When the hair removing device is operating, the light source 101 may generate a large amount of heat, the reflector 102 and the filter 103 may be irradiated by the light, such that a temperature of the reflector 102 and filter 103 may be increased. Therefore, heat of the light source 101, the reflector 102 and the filter 103 needs to be dissipated.

In the present embodiment, the bracket 500 may include the fixing frame 550 and a tube 560. An end of the tube 560 may be connected to a side of the fixing frame 550, and the other end of the tube 560 may extend towards the cold drive assembly 400. The fixing frame 550 defines an air outlet 540 communicated with the first receiving space 510, and the tube 560 defines an air inlet 530 communicated with the first receiving space 510. The air inlet 530, the first receiving space 510 and the air outlet 540 may be sequentially communicated with each other.

The air inlet 530 may be connected to the cold drive assembly 400. The air outlet 540 may be communicated with the air vent 1211. The cold drive assembly 400 may absorb the external air from the air vent 1211 and blow the air towards the air outlet 540. The air enters the first receiving space 510 through the air outlet 540 and carries away the heat from the light source 101, the reflector 102 and the filter 103 in the first receiving space 510. Further, the air may flow out the device through the air outlet 540 and the air vent 1211 to dissipate the heat.

In some embodiments, a part of the fixing frame 550 and a part of the tube 560 form a first bracket 501, and the remaining part of the fixing frame 550 and the remaining part of the tube 560 form a second bracket 502. In other embodiments, the fixing bracket 550 may be configured as an integral one-piece structure.

The first bracket 501 and the second bracket 502 may be connected to each other through a snap. The first bracket 501 may be disposed near the first housing 121, and the second bracket 502 may be disposed near the second housing 122. The air outlet 540 may be defined in the first bracket 501 and may be opposite to the air vent 1211 in the first housing 1211 to increase the heat dissipation efficiency at the air outlet 540. The first receiving space 510 may be defined in a part of the first bracket 501 and a part of the second bracket 502. The part of the first bracket 501 and the part of the second bracket 502 may correspond to the fixing frame 550 and may be snapped with each other. The air inlet 530 may be defined in another part of the first bracket 501 and another part of the second bracket 502. The another part of the first bracket 501 and the another part of the second bracket 502 may correspond to the tube 550 and may be snapped with each other. The air inlet 530 may be communicated with the first receiving space 510 and connected to the cold drive assembly 400. An inside of the bracket 5 may define a channel for guiding an airflow, facilitating the airflow of the cold drive assembly 400 to be guided into the first receiving space 510.

Therefore, in the present embodiment, the hair removing assembly 100 may dissipate heat through the cold drive assembly 400, ensuring the hair removing device to be used safely.

Further, in the present embodiment, the cold compressing assembly 200 may include a light-transmitting body 202 and a refrigerating member 201.

The light-transmitting body 202 may be configured to attach to the skin. The light-transmitting body 202 may face the light source 101. The light-transmitting body 3 may be an element allowing the light to pass through. The light emitted by the light source 101 enters the light-transmitting body 202, and passes through the light-transmitting body 202 to further reach the skin.

In some embodiments, the light-transmitting body 202 may be a light conductive crystal, such as sapphire, K9 glass or crystal glass. When the light-transmitting body 202 is the sapphire, the light-transmitting body 202 may have excellent thermal conductivity.

In some embodiments, the light-transmitting body 202 may be cylindrical or cuboid. A face of the light-transmitting body 202 away from the light source 101 may be configured to attach the skin.

The refrigerating member 201 may be connected to the light-transmitting body 202 to absorb heat from the light-transmitting body 202. Since the temperature of the light-transmitting body 202 is increased when the light-transmitting body 202 contacts the skin, the refrigerating member 201 may absorb the heat of the light-transmitting body 202 after the temperature of the light-transmitting body 202 is increased, such that the light-transmitting body 202 remains cold, and when the light-transmitting body 202 is contacting the skin for a long period of time, the light-transmitting body 202 may still cool the skin, and the burning sensation to the skin may be reduced.

Further, the refrigerating member 201 may be a semiconductor refrigerating member. An end of the refrigerating member 201 that absorbs heat may be connected to the light-transmitting body 202, and the other end of the refrigerating member 201 may dissipate the heat.

In order to dissipate heat from the heat dissipating end of the refrigerating member 201, in the present embodiment, the heat dissipation base 300 is connected to the heat absorbing end of the refrigerating member 201 and absorbs the heat from the refrigerating member 201.

In detail, the heat dissipation base 300 may include a heat dissipation plate 301 and a heat dissipation wing 302. A surface of the heat dissipation plate 301 includes a first region 310 and a second region 311 side by side. The hair removing assembly 100 is arranged in the first region 310, and the heat dissipation wing 302 is arranged in the second region 311. The second region 311 is arranged on a side of the fixing frame 550 connected to the tube 560. The heat dissipation wing 302 and the tube 560 are disposed side by side on a side of the fixing frame. The fixing frame 550 is arranged in the first region 310. The heat dissipation plate 301 is arranged on the circuit board 600 and is connected to the cold compressing assembly 200. In detail, the heat dissipation member 201 may be bonded to the heat dissipation plate 301 by a thermally-conductive silicone grease. The cold compressing assembly 200 may quickly transfer the heat to the heat dissipation plate 301 through the thermally-conductive silicone grease. The heat dissipation wing 302 may dissipate heat from the heat dissipation plate 301 and assist the heat dissipation plate 301 to dissipate the heat, such that the heat dissipation plate 301 may continuously absorb heat from the refrigerating member 201.

In some embodiments, the number of heat dissipation wings 302 may be more than one. The more than one heat dissipation wings 302 may be parallel to each other and may be mounted on the heat dissipation plate 301 by welding.

In some embodiments, a surface of the heat dissipation wing 302 may be sprayed with a heat-conductive paint. The heat-conductive paint may radiate to dissipate the heat away from the heat dissipation wing 302, and may prevent the heat dissipation wing 302 from being affected by water, being corroded and being worn.

In the present embodiment, the heat dissipation plate 301 may be a temperature homogeneous plate. When a liquid inside the temperature homogeneous plate encounters an environment at a high temperature, the liquid may absorb heat and may be vaporized into gas. When the gas encounters an environment at a low temperature, the gas may dissipate heat and may be liquified into the liquid. Therefore, a temperature of a surface of the temperature homogeneous plate may be kept homogeneous due to periodic evaporation and condensation. Therefore, a part of the surface of the heat dissipation plate 301 is connected to the refrigerating member 201, and the other part is connected to the heat dissipation wing 302, such that the heat generated by the refrigerating member 201 may be dissipated through the heat dissipation plate 301 and the heat dissipation wing 302.

In some embodiments, the carbon-containing layer may be disposed between the light-transmitting body 202 and the heat dissipation base 300, such as on a surface of the heat dissipation plate 301 thermally coupling with the light-transmitting body 202. The carbon-containing layer has excellent thermal conductivity, and may accelerate a thermal conducting rate of the heat dissipation plate 301 and improve heat dissipation performance of the heat dissipation base 300.

In some embodiments, the carbon-containing layer may be a graphene material, graphite powder, a graphite sheet or a graphite film.

In some embodiments, the carbon-containing layer may be arranged by plating, spraying or attaching.

In order to improve the heat dissipation performance of the heat dissipation base 300, in the present embodiment, the heat dissipation base 300 may further be connected to the cold drive assembly 400.

In detail, the heat dissipation wing 302 of the heat dissipation base 300 may be connected to the cold drive assembly 400. The cold drive assembly 400 may absorb the external air through the air vent 1211 and drive the air to flow towards the heat dissipation wing 302. The air may flow along the heat dissipation wing 302 to dissipate heat from the heat dissipation wing 302.

In an example, the heat dissipation wing 302 may be arranged parallel to an airflow direction driven by the cold drive assembly 400 to increase a contact area between the heat dissipation wing 302 and the airflow, increasing the efficiency of dissipating heat from the heat dissipation wing 302.

The heat dissipation wing 302 may face the air vent 1211 in the first housing 121. The airflow, after flowing along the heat dissipation wing 302, may quickly flows out of the device through the air vent 1211.

Therefore, the cold drive assembly 400 of the present embodiment may drive the cooling medium to dissipate heat from the hair removing assembly 100, and may further dissipate heat from the heat dissipation base 300. With improved safety, the irradiated skin may be compressed to be cooled, and burning of the irradiated skin may be reduced. Further, the cold compressing assembly 200 may be controlled by the heat dissipation base 300 and the cold drive assembly 400 to reach a low temperature of about zero degrees. In this way, the skin near a light outlet port may infinitely approach a freezing point, burning sensation of the skin may be reduced, and a short contact between the skin the device may not cause damage to the skin.

Figure 10:
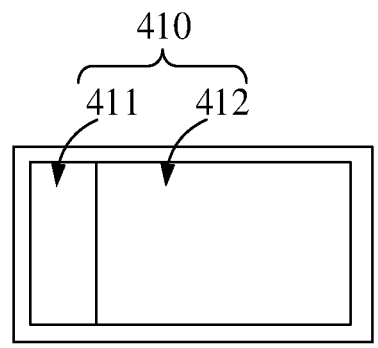
FIG. 10 is a structural schematic view of an air outlet of a fan housing of the embodiment shown in FIG. 8.

As shown in FIG. 7, FIG. 8 and FIG. 10, FIG. 10 is a structural schematic view of an air outlet of a fan housing of the embodiment shown in FIG. 8. In the present embodiment, the cold drive assembly 400 may include a fan housing 401 and a fan 402. The fan housing 401 is arranged on a side of the heat dissipation base 300 away from the cold compressing assembly 200, and the fan 402 is received inside the fan housing 401.

An air inlet end of the fan 402 faces the air vent 1211 in the first housing 121. The fan 402 drives the external air to flow into the fan 402 through the air vent 1211. The fan housing 401 defines an air outlet 410 for outputting air. An air outlet end of the fan 402 is connected to the air outlet 410. The fan 402 drives the external air to flow into the fan 402 through the air vent 1211 and further drives the air to flow out through the air outlet 410.

In some embodiments, the fan 402 may be a centrifugal fan, an axial flow fan, a mixed flow fan or a cross flow fan.

Further, the air outlet 410 may include a first air outlet 411 and a second air outlet 412. Air at the air outlet 410 of the fan 402 may be divided into two parts. One of the two parts of the air flows out of the device through the first air outlet 411, and the other one of the two parts of the air flows out of the device through the second air outlet 412.

In some embodiments, the air outlet 410 may further include a third air outlet or more air outlets. The present disclosure does not limit the number of the air outlets.

In the present embodiment, the first air outlet 411 is communicated with the air inlet 530 of the bracket 500. The fan 402 drives the external air to enter the fan 402 through the air vent 1211. The fan 402 drives the air to flow from the first air outlet 411 and the air inlet 530 into the first receiving space 510. The air in the first receiving space 510 may carry the heat away from the light source 101, the reflector 102 and the filter 103. Finally, the air flows out of the device from the air outlet 540 and the air vent 1211. In this way, heat is dissipated to the outside of the device, enabling the heat of the hair removing assembly 100 to be dissipated.

In the present embodiment, the second air outlet 412 is connected to the heat dissipation wing 302 of the heat dissipation base 300. The fan 402 drives the external air to enter the fan 402 from the air vent 1211. The fan 402 drives the air to flow between every two of the more than one heat dissipation wings 302 of the heat dissipation base 300 through the second air outlet 412. The air flows along the heat dissipation wings 302, carries the heat away from the heat dissipation wings 302, and further flows out of the device from the air vent 1211. After temperatures of the heat dissipation wings 302 are decreased, the heat of the heat dissipation plate 301 may be decreased accordingly. In this way, the heat dissipation plate 301 may absorb the heat of the cold compressing assembly 200, enabling the heat of the cold compressing assembly 200 to be dissipated.

In some embodiments, the amount of the air flowing in the first air outlet 411 and the second air outlet 412 will not be limited herein and may be determined based on demands. The amount of the air flowing in the first air outlet 411 and the second air outlet 412 may be controlled by configuring a size of the first air outlet 411 and a size pf the second air outlet 412. For example, in the present embodiment, an air outlet area of the second air outlet 412 is greater than an air outlet area of the first air outlet 411, such that a larger amount of air flows through the second air outlet 412 to enhance the efficiency of dissipating the heat from the heat dissipation plate 301.

According to the above embodiments, in the hair removing device of the present embodiment, heat of the hair removing assembly 100, the cold compressing assembly 200 and the heat dissipation base 300 may be dissipated by the cold drive assembly 400, such that heat of the hair removing assembly 100 and the cold compressing assembly 200 may be dissipated simultaneously. The heat dissipation performance of the hair removing device may be improved, and the safety of the hair removing device may be improved. In addition, the skin may be compressed to be cooled continuously, and the temperature of the skin may infinitely approach the freezing point, such that the burning sensation of the skin may be reduced, and the skin may be prevented from being damaged while the hair is being removed.

Figure 16:
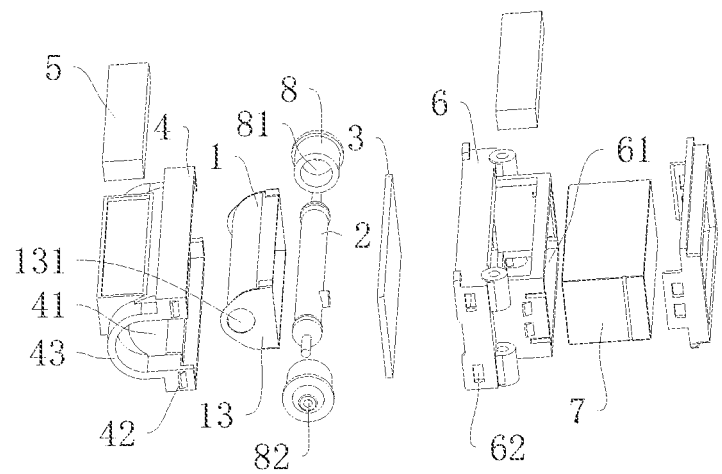
FIG. 16 is an exploded view of the device according to another embodiment of the present disclosure.
Figure 17:
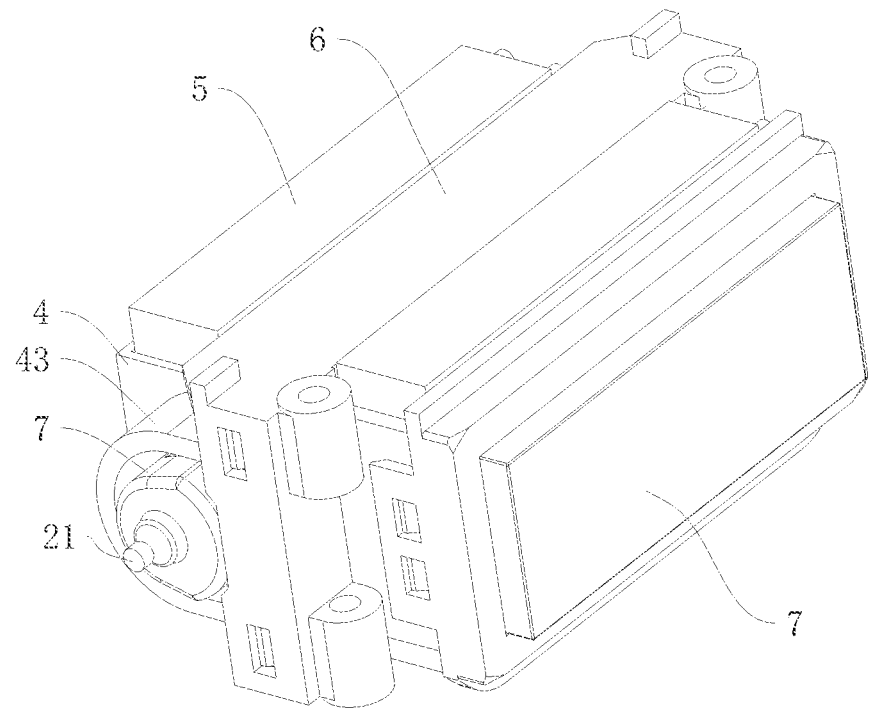
FIG. 17 is an assembled view showing the entire structure of the device according to another embodiment of the present disclosure.

As shown in FIG. 16 and FIG. 17, the present disclosure provides a hair removing device. The hair removing device may include the reflector 1, the light source 2, a first light-transmitting body 3, a heat dissipation base 4 and a refrigerating member 5. The light source 2 is arranged inside the reflector 1 and is configured to emit light. The reflector 1 may reflect the light. The first light-transmitting body 3 is arranged on and covers a light exiting side of the reflector 1. Further, the first light-transmitting body 3 and the reflector 1 cooperatively define a cavity to receive the light source 2.

The reflector 1 is embedded in a heat dissipation base 4. A side of the heat dissipation base 4 contacting the reflector 1 is thermally coupled to the reflector 1. The refrigerating member 5 is arranged on the heat sink dissipation base 4. A refrigerating side of the refrigerating member 5 is thermally coupled to the side of the heat dissipation base 4 contacting the refrigerating member 5. A body of the light source 2 may be suspended in the cavity, and the refrigerating member 5 is configured to cool the cavity.

While the hair removing device is operating, the light source 2 in the reflector 1 emits a large amount of light, and heat generated by the light may be collected in the cavity. In addition, the temperature of the reflector 1 may be increased as the heat is collected in the cavity. A side of the heat dissipation base 4 is thermally coupled to the reflector 1, and the other side of the heat dissipation base 4 is thermally coupled to the refrigerating member 5. The thermal coupling may be achieved by any one or combination of heat transfer, thermal convection and thermal radiation. That is, the heat of the reflector 1 may be dissipated through the heat dissipation base 4, and the heat in the cavity may be dissipated, such that the reflector 1 and the cavity may be cooled down, and the efficiency of dissipating the heat from the light source 2 may be improved. By configuring the body of the light source 2 to be suspended in the cavity, the heat of the light source 2 may be dissipated more uniformly, and the service life of the light source 2 may be improved. In detail, the heat generated while the light source 2 is operating may be dissipated by radiating towards all directions. In addition, the air is evenly distributed around the light source 2, the air may fully contact the light source 2 and may evenly dissipate the heat generated by the light source 2. The heat may be generated by the light source 2, transferred through the cavity to the reflector 1 and the first light-transmitting body 3, and then dissipated out of the device.

Further, the refrigerating member 5 may further dissipates the heat from the heat dissipation base 4 to achieve rapid heat dissipation, improving the heat dissipation effect of the hair removing device. Further, radiation of heat from the cavity to other components of the hair removing device may be reduced. In this way, while the hair removing device is being used, the burning sensation at the skin that has hair to be removed may be reduced, improving the performance of the hair removing device.

Figure 18:
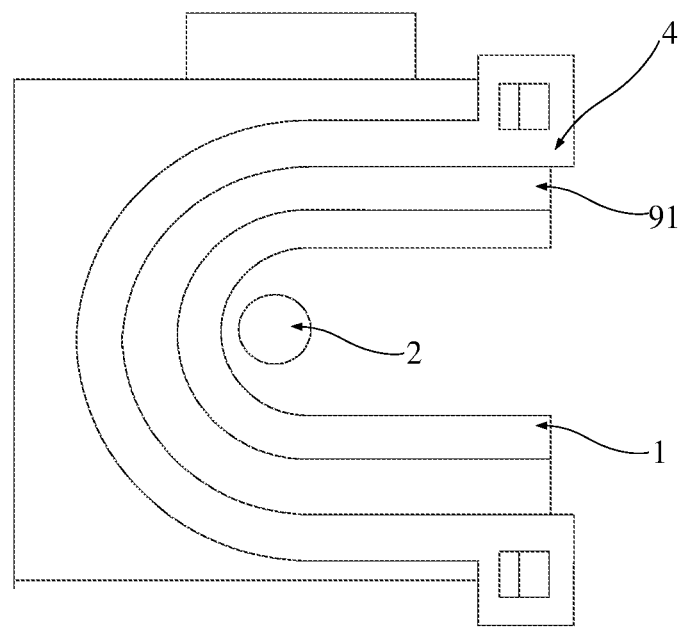
FIG. 18 is a structural schematic view of a carbon-containing layer according to an embodiment of the present disclosure.

In some embodiments, the hair removing device may further include the carbon-containing layer, arranged in the reflector 1. For example, as shown in FIG. 18, the carbon-containing layer 91 may be arranged on a side of the reflector 1 facing away from the reflector 2. The light source 2 may generate heat while being used, and the heat may be collected in the reflector 1. The carbon-containing layer 91 has excellent thermal conductivity, which may increase the thermal conducting rate of the reflector 1 and improve the heat dissipation performance of the reflector 1, preventing the hair removing device from being damaged due to the high temperature and preventing irritation or damage to the skin of the user.

In some embodiments, the carbon-containing layer is arranged on the heat dissipation base 4. As shown in FIG. 18, for example, the carbon-containing layer may be disposed between the heat dissipation base 4 and the reflector 1, increasing the thermal conductivity rate between the heat dissipation base 4 and the reflector 1.

In some embodiments, the carbon-containing layer may be disposed on the side of the refrigerating member 5 facing the heat dissipation base 4 or on an exposed surface of the refrigerating member 5 to enhance the cooling effect of the refrigerating member 5. In this way, the heat of the heat dissipation base 4 may be dissipated timely and rapidly, such that the heat of the reflector 1 may be dissipated quickly.

In some embodiments, the carbon-containing layer may be the graphene material, the graphite powders, the graphite sheet or the graphite film and may be arranged at any available position as described in the present disclosure by plating, spraying or attaching.

In some embodiments, the heat dissipation base 4 may be a ceramic base or a base made of aluminum. The heat dissipation base 4 may be configured to quickly dissipate heat from the reflector 1 to improve the heat dissipation effect of the reflector 1. For example, the ceramic has stable physical properties, such as being corrosion resistant, having low thermal expansion. Further, the ceramic absorbs heat quickly. Therefore, the ceramic base may quickly absorb the heat, and the reflector 1 and the cavity may be cooled by the ceramic base, improving the heat dissipation effect of the hair removing device.

In addition, the ceramic is an insulator. A short circuit may not occur when the ceramic contacts the reflector 1. The ceramic base covers an outer surface of the reflector 1, reducing a risk of electrical leakage at the reflector 1 of the device and improving the safety of the hair removing device. The body of the light source 2 is suspended in the cavity and is spaced apart from the reflector, which may be a conductor. When power is supplied to the device, a strong electric field is formed between the light source 2 and the reflector 1 and excites the light source 2 to emit light.

A side of the ceramic base is arranged with a groove body 41. The groove body 41 may be strip shaped. In some embodiments, the reflector 1 may be a semi-arc reflector. The reflector 1 may be embedded in the groove body 41. The first light-transmitting body 3 may be a filter or a transparent glass carrier. The first light-transmitting body 3 may be fixed relative to the ceramic base. The heat generated by the light source 2 may be constrained in the cavity by the first light-transmitting body 3 and the reflector 1, reducing the possibility that the heat radiates to other components of the hair removing device. In the present embodiment, the ceramic base is arranged with the groove body 41, and the reflector 1 is embedded in the groove body 41, such that the contact area between the ceramic base and the reflector 1 may be increased, increasing the capacity that the ceramic base absorbs heat from the reflector 1, and improving the heat dissipation effect of the reflector 1 and the cavity.

In some embodiments, the reflector 1 may be a strip shaped reflector.

As shown in FIG. 16, in some embodiments, the refrigerating member 5 may be a TEC refrigerating sheet or a refrigerating block. The refrigerating member 5 is configured to cool the heat dissipation base 4 to remove the heat from the heat dissipation base 4 timely and rapidly, such that heat of the reflector 1 may be dissipated quickly. In the present embodiment, the refrigerating member 5 is the TEC refrigerating sheet, which is for the illustrative purposes only. The present disclosure does not limit detailed structure of the refrigerating member 5.

In some embodiments, the heat dissipation base 4 may be strip shaped. The TEC refrigerating sheet may be strip shaped. The heat dissipation base 4 defines a mounting slot. The mounting slot is defined in a side of the heat dissipation base 4 away from the opening of the reflector 1. The TEC refrigerating sheet is received in the mounting slot. The TEC refrigerating sheet adequately contacts the heat dissipation base 4. The TEC refrigerating sheet quickly transfers the heat, which is transferred from the cavity and the reflector 1 to the heat dissipation base 4, away from the heat dissipation base 4, such that the heat dissipation base 4 may be cooled. In this way, on one hand, while the hair removing device is operating, the light source 2 may be protected better, and damages to the light source 2 caused by the high temperature may be reduced effectively, increasing the service life of the light source 2. On the other hand, a temperature of an outer surface of the hair removing device may be reduced, and the user may hold the hair removing device comfortably by hand, enhancing the performance of the hair removing device.

Figure 19:
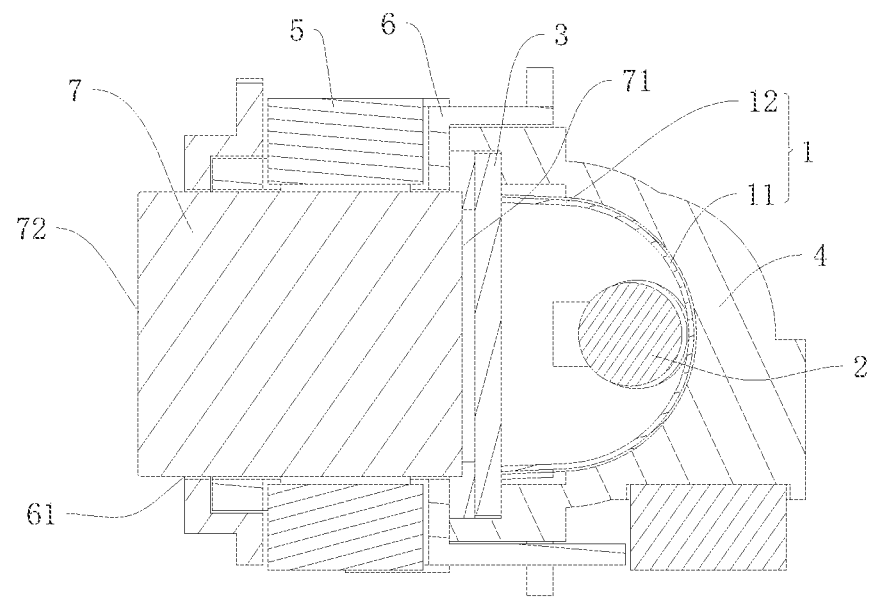
FIG. 19 is a cross sectional view showing the entire structure of the device according to another embodiment of the present disclosure.

As shown in FIG. 16, FIG. 17 and FIG. 19, the hair removing device includes a bracket 6. The bracket 6 is configured to work cooperatively with the heat dissipation base 4 to assemble the reflector 1 together with the first light-transmitting body 3. The bracket 6 defines a window 61. The window 61 may be square or rectangular. The first light-transmitting body 3 is fixed to the bracket 6 and covers the window 61. The heat dissipation base 4 and the bracket 6 may be detachably connected with each other, such that the hair removing device may be assembled and disassembled easily. The reflector 1 and the first light-transmitting body 3 can be fixed with each other by the heat dissipation base 4 and the bracket 6. In this way, components inside the hair removing device may be arranged more compactly, an inner space of the device may be saved, design of the device may be reasonable, and the device may be used easily.

In some embodiments, each of two sides of the heat dissipation base 4 is arranged with a first fastening portion 42, and the first fastening portion 42 and the heat dissipation base 4 may be configured as an integral one-piece structure. Each of two sides of the bracket 6 is arranged with a second fastening portion 62, and the second fastening portion 62 and the bracket 6 may be configured as an integral one-piece structure. The first fastening portion 42 may correspond to the second fastening portion 62. In the process of connecting the heat dissipation base 4 with the bracket 6, the first fastening portion 42 may be tightly fastened with the second fastening portion 62. In this way, the heat dissipation base 4 and the bracket 6 may be connected together stably, enhancing stability of the hair removing device.

In some embodiments, the first fastening portion 42 may be a buckle block or a cantilever hook, and the second fastening portion 62 may be a fixing hole. While connecting the heat dissipation base 4 with the bracket 6, the cantilever hook may be received into the fixing hole. Further, after the cantilever hook is received in the fixing hole, a wall of the fixing hole may restrict the cantilever hook, preventing the cantilever hook from easily leaving out of the fixing hole. In this way, the first fastening portion 42 and the second fastening portion 62 may be stably connected, i.e., the heat dissipation base 4 and the bracket 6 may be fixed with each other, effectively preventing the heat dissipation base 4 from being loosed from or falling off from the bracket 6, and improving the stability of the entire hair removing device.

As shown in FIG. 16, FIG. 17 and FIG. 19, the bracket 6 fixes the second light-transmitting body 7. The second light-transmitting body 7 may be square or rectangular and may be embedded in the window 61. The second light-transmitting body 7 is disposed on a side of the filter facing away from the light source 2. The second light-transmitting body 7 has a light incidence surface 71 facing the light source 2 and a light exiting surface 72 facing away from the light source 2. In some embodiments, the second light-transmitting body 7 may be a crystal. The second light-transmitting body 7 may alternatively be a diamond. In the present embodiments, the second light-transmitting body 7 being the crystal may be taken as an example.

While the hair removing device is operating, the light source 2 emits light, and the light is reflected by the reflector 1. Further, the light passes through the filter and is reflected to reach the crystal. The light enters the crystal from the light incidence surface 71. The light may be reflected by the crystal itself and exits the crystal from the light exiting surface 72. The light emitted from the light exiting surface 72 may irradiate a skin area that has the hair to be removed to remove the hair.

In some embodiments, the number of TEC refrigerating sheets may be two or three. For example, two TEC refrigerating sheets may be arranged, and the two TEC refrigerating sheets are spaced apart from each other. One of the two TEC refrigerating sheets is fixed to the heat dissipation base 4, and the other one of the two TEC refrigerating sheets is arranged on the bracket 6. The bracket 6 defines a mounting opening, communicating with the window 61. When the second light-transmitting body 7 is embedded in the window 61, the TEC refrigerating sheet is embedded in the mounting opening and abuts against the second light-transmitting body 7. The TEC refrigerating sheet cools the second light-transmitting body 7 to allow the heat of the second light-transmitting body 7 to be quickly dissipated. The temperature of the second light-transmitting body 7 may be reduced effectively, optimally preventing the light-emitting surface 72 from being heated, such that the hair removing device may safely contact the skin area that has the hair to be removed, and the user may use the hair removing device more comfortably.

In some embodiments, for example, three TEC refrigerating sheets may be arranged. One of the three TEC refrigerating sheets is fixed to the heat dissipation base 4, and the other two TEC refrigerating sheets are embedded in the bracket. The other two TEC refrigerating sheets are disposed on two sides of the second light-transmitting body 7, respectively. The two sides may be an upper side and a lower side of the second light-transmitting body 7 facing a direction that the light exits the second light-transmitting body 7, or a left side and a left side of the second light-transmitting body 7. The two TEC refrigerating sheets disposed on the two sides of the second light-transmitting body 7 improve an efficiency of cooling the second light-transmitting body 7, such that heat of the second light-transmitting body 7 may be dissipated quickly, achieving the cooling effect, and improving the heat dissipation effect of the hair removing device.

Figure 20:
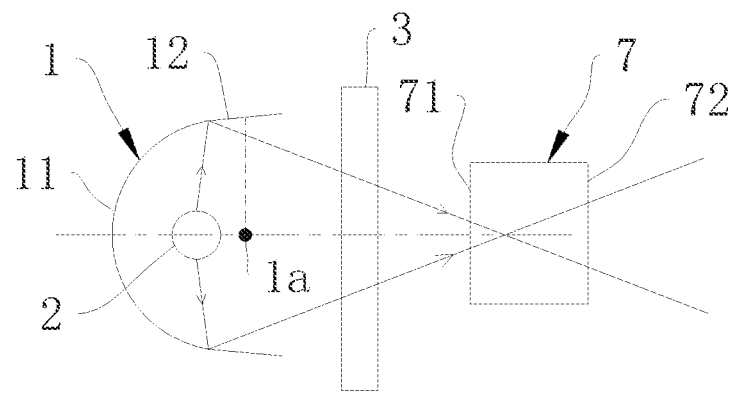
FIG. 20 shows a light propagating path according to an embodiment of the present disclosure.

As shown in FIG. 20, in some embodiments, structures and relative positions of the light source 2, the reflector 1 and the second light-transmitting body 7 may satisfy the following. The uniformity of the light exiting surface 72 outputting the light may be greater than or equal to 90%, or light spots on the light exiting surface 72 occupies at least 95% of the area of the light exiting surface 72. When the uniformity of the light exiting surface 72 outputting the light is greater than or equal to 90%, the hair removing effect of the hair removing device may be improved, enabling the hair on the skin to be uniformly removed. Similarly, when the light spots on the light exiting surface 72 occupies at least 95% of the area of the light exiting surface 72, the hair on the skin may be uniformly removed, and utilization of the light may be improved.

When the light exiting surface 72 of the hair removing device outputs the light less uniformly, or when the light spots occupy a relatively small area of the light exiting surface 72, the hair removing device, while in use, may irradiate one position several times to uniformly remove the hair, otherwise the hair may not be removed evenly and the skin may not have a satisfied appearance. For the structures and the relative positions of the light source 2, the reflector 1 and the second light-transmitting body 7 in the present embodiment, the uniformity of the light exiting surface 72 outputting the light is greater than or equal to 90%, or the light spots occupy at least 95% of the area of the light exiting surface 72. In this way, the hair removing device does not need to irradiate one position several times. When quality of the light source 2 and the power of the hair removing device is properly configured, and when health of the user is ensured, the hair removing device may irradiate one position once to remove the hair on the one position efficiently and uniformly.

In some embodiments, a center of the reflector 1, a center of the light source 2 and a center of the second light-transmitting body 7 may locate on a straight line. By adjusting a distance between the centers on the straight line, the uniformity of the light exiting surface 72 outputting the light may be greater than or equal to 90%, or the light spots may occupy at least 95% of the area of the light exiting surface 72. In some embodiments, structures of the reflector 1, the light source 2, the second light-transmitting body 7 may be adjusted to allow the hair removing device to meet the above features.

In some embodiments, the center of the light source 2 is located between a focal point of the reflector 1 (shown as 1a in the drawing) and a bottom of the reflector 1. The light incidence surface 71 of the second light-transmitting body 7 is disposed between the light exiting surface 72 and the focal point of the reflector 1. Further, the light reflected from the reflector 1 may be focused at a position between the light exiting surface 72 of the second light-transmitting body 7 and the focal point of the reflector 1. By configuring positions of the light source 2, the reflector 1 and the second light-transmitting body 7, the uniformity of the light exiting surface 72 outputting the light may be greater than or equal to 90%, or light spots on the light exiting surface 72 occupies at least 95% of the area of the light exiting surface 72. In this way, the light emitted by the light source 2 may be fully reflected by the reflector 1 to reach the second light-transmitting body 7, improving the uniformity that the second light-transmitting body 7 outputs the light.

As shown in FIG. 19, the reflector 1 has a first reflective region 11 and a second reflective region 12. The first reflective region 11 is a curved region including the bottom of the reflector 1, and the second reflective region 12 is two flat regions extending outwards from two ends of the curved region. The flat region may be tangential to the curved region. In some embodiments, the light source 2 may be a strip-shaped lamp. The strip-shaped lamp emits light, and the curved region of the reflector 1 may reflect the light to the second light-transmitting body 7. In addition, the flat regions of the reflector 1 may also reflect the light to the second light-transmitting body 7. The light may be reflected adequately by the curved region and the flat regions, such that a light emission rate may be improved, and utilization of the light may be improved.

For example, when the hair removing device is operating, the light source 2 emits light, the first reflective region 11 and the second reflective regions 12 of the reflector 1 may fully reflect the light onto the second light-transmitting body 7. The light enters the second light-transmitting body 7 from the light incident surface, and afterwards, the light exits the second light-transmitting body 7 from the light exiting surface 72, such that the uniformity of the light exiting surface 72 outputting the light may be greater than or equal to 90%, or light spots on the light exiting surface 72 occupies at least 95% of the area of the light exiting surface 72. In this way, the uniformity that the hair removing device outputs the light may be improved, and the hair removing effect of the hair removing device may be improved.

In some embodiments, an angle between the flat region and a reference line may be between 5 and 20 degrees. The reference line may be a line between the center of the light source 2 and the center of the second light-transmitting body 7. For example, the angle between the flat region and the reference line may be 5 degrees or 8 degrees, or the angle between the flat region and the reference line may be 15 degrees. By configuring the angle between the flat region and the reference line, the light may be fully reflected onto the second light-transmitting body 7. On one hand, the waste of the light may be reduced, a usage cost may be reduced. On the other hand, the uniformity that the second light-transmitting body 7 outputs the light may be improved.

For example, in the above range, the focal point may be closer. When conditions about the light uniformity and the light utilization are satisfied, the second light-transmitting body 3 may be closer to the light source 2, such that the hair removing device may have a more compact structure, and material for making the hair removing device may be saved.

As shown in FIG. 16, FIG. 17, and FIG. 19, the hair removing device may further include a side reflecting member 13, arranged on each of two ends of the reflector 1 along a length direction of the reflector 1. The side reflecting member 13 may reflect light, which escapes from the two ends of the reflector 1, onto the light exiting side of the reflector 1. The side reflecting member 13 fully reflects the light emitted by the light source 2 in order to improve the light utilization rate and enable the hair removal device to remove hair efficiently. In addition, the light source 2 may be easily assembled by the side reflecting member 13, improving an efficiency of assembling.

In some embodiments, the side reflecting member 13 and the reflector 1 may be configured as an integral one-piece structure. In this way, difficulty producing the side reflecting member 13 and the reflector 1 may be reduced. In addition, when the side reflecting member 13 and the reflector 1 is the integral one-piece structure, the one-piece structure may be stable and firm, stability of connection between the side reflecting member 13 and the reflector 1 may be improved, and the service life of the reflector 1 may be increased.

In some embodiments, the light source 2 may be a strip shaped lamp. Each of two side reflecting members 13, which are arranged at each of two sides of the reflector 1, defines a through hole 131, and two side reflecting members 13 at the two ends may define two through holes 131. Two ends of the lamp pass through the two through holes 131, respectively. A fixing member 8 is connected to each of two ends of the lamp to movably fix the light source 2 to the reflector 1. For example, the fixing member 8 may be a silicone soft cover. The fixing member 8 may alternatively be a rubber cover. The fixing member 8 may be cylindrical. The fixing member 8 may define a mounting slot 81. Each of two ends of the lamp is embedded in the mounting slot 81. The fixing member 8 defines a fixing hole 82 along an axis of the fixing member 8. The fixing hole 82 is communicated with the mounting slot 81. Each of the two ends of the lamp is arranged with a mounting post 21 extending from the lamp. The mounting post 21 may extend through the fixing hole 82. The fixing member 8 may be arranged at an outside of the reflector 1.

In some embodiments, a support block 43 is arranged at each of two ends of the heat dissipation base 4, and the support block 43 and the heat dissipation base 4 may be configured as an integral one-piece structure. The support block 43 defines a notch. Each of the two ends of the light source 2 and a corresponding fixing member 8 may be received in the notch. When the heat dissipation base 4 and the bracket 6 are fastened, the bracket 6 and the support block 43 may fix the fixing member 8, such that the lamp may be fixed on the reflector 1. The fixing member 8 itself may be elastic. While the bracket 6 and the support block 43 are fixing the fixing member 8, when the fixing member 8 is compressed, a shape of the fixing member 8 may be changed correspondingly to adapt to a shape of the notch. In addition, a compression force applied to the lamp may be optimally reduced, reducing damage to the lamp.

The present disclosure provides a hair removing device which has an enhanced heat dissipation effect. The light source 2 is arranged inside the reflector 1 and is configured to emit light. The reflector 1 may reflect the light, enabling the hair removing device to emit the light to remove hair from the skin. The first light-transmitting body 3 and the reflector 1 may cooperatively define a cavity to receive the light source 2, and the light source 2 is suspended in the cavity. Two sides of the heat dissipation base 4 may be thermally coupled to the reflector 1 and the refrigerating member 5 respectively, such that the heat in the cavity may be quickly transferred out of the cavity. That is, the heat in the cavity may be transferred to the heat dissipation base 4 and the refrigerating member 5. In this way, the cavity may be cooled, the heat dissipation effect of the hair removing device may be improved. In addition, the heat of the light source 2 may be dissipated uniformly, extending the service life of the light source 2. Further, the enhanced heat dissipation effect enables the user to use the hair removing device comfortably.

Figure 26:
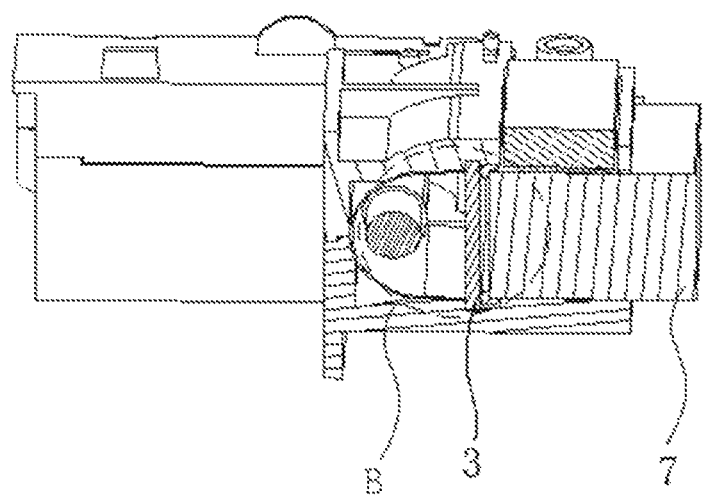
FIG. 26 is a cross sectional view showing the entire structure of the device according to another embodiment of the present disclosure.
Figure 27:
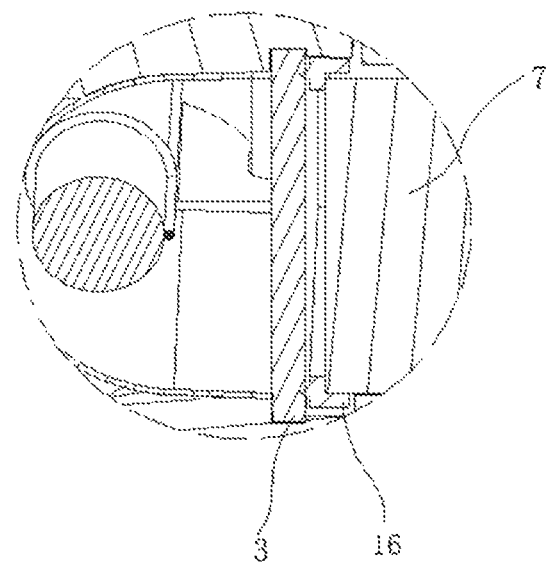
FIG. 27 is an enlarged view of a portion B shown in FIG. 26.

As shown in FIG. 26 and FIG. 27, in another embodiment, an elastic seal ring 16 is disposed between the second light-transmitting body 7 and the first light-transmitting body 3. The elastic seal ring 16 may be ring-shaped. The second light-transmitting body 7 and the first light-transmitting body 3 may be sealed with the elastic seal ring 16. In this way, water condensation may not be generated between the first light-transmitting body 3 and the second light-transmitting body 7. Dirt may not penetrate into the connection between the first light-transmitting body 3 and the second light-transmitting body 7. The elastic seal ring 16 may be preferably ring-shaped.

Of course, when the hair removing device falls to the ground, the second light-transmitting body 7 may rigidly collide with the ground. A colliding impact of a conventional second light-transmitting body 7 may be transferred to the first light-transmitting body 3, such that the first light-transmitting body 3, the reflector 1 and the light source 2 may be vibrated and damaged. For the hair removing device in the present embodiment, when the second light-transmitting body 7 is collided, the impact force may be eliminated by the elastic seal ring 16. Due to the elasticity of the elastic seal ring 16, the elastic seal ring 16 may be elastically deformed when being compressed by external forces, reducing or eliminating the impact between the second light-transmitting body 7 and the first light-transmitting body 3, and reducing a possibility that the first light-transmitting body 3, the reflector 1 and the light source 2 are broken by the impact force. Therefore, anti-collision performance of the hair removing device may be enhanced.

Figure 28:
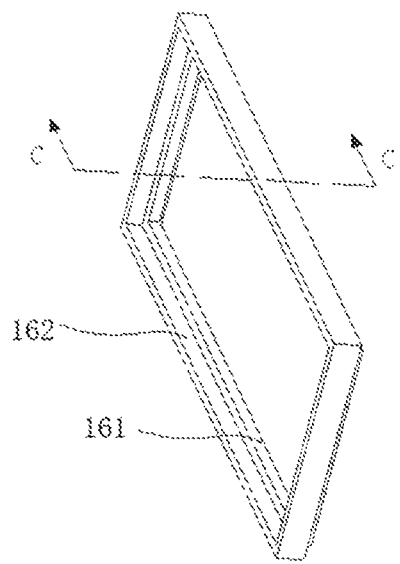
FIG. 28 is a structural schematic view of an elastic seal ring according to an embodiment of the present disclosure.
Figure 29:
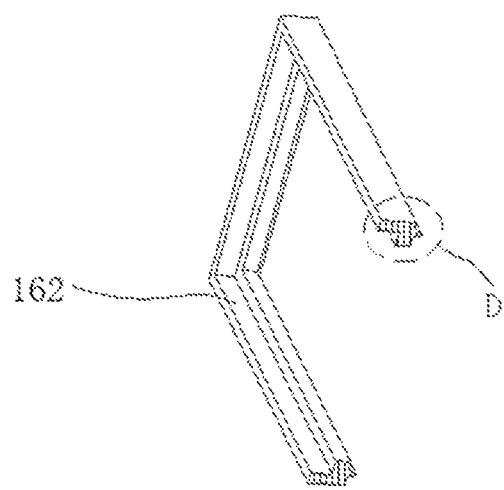
FIG. 29 is a cross sectional view of the embodiment shown in FIG. 28 by taking along the line C-C.
Figure 30:
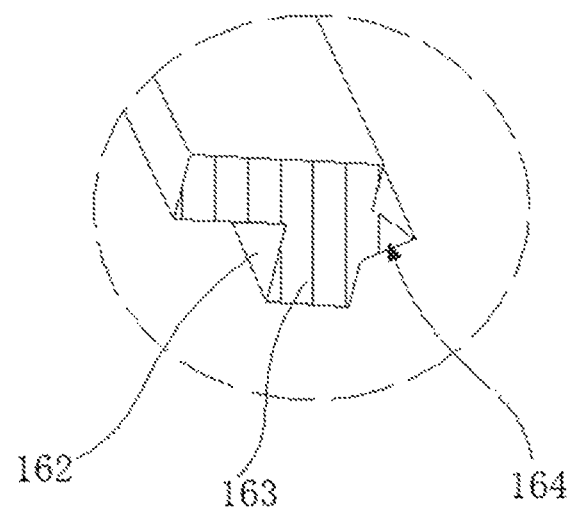
FIG. 30 is an enlarged view of a portion D shown in FIG. 29.

As shown in FIGS. 28 to 30, the elastic seal ring 16 has an inner ring 161 that allows the light to pass through. The light, after being filtered by the first light-transmitting body 3, may be guided to the second light-transmitting body 7 through the inner ring 161 and further irradiate the skin of the user.

In the present embodiment, the first light-transmitting body 3 and the second light-transmitting body 7 may be fixed directly to the bracket 7. The first light-transmitting body 3 and the second light-transmitting body 7 cannot be moved relative to the bracket 6. Therefore, while the hair removing device is being used, the second light-transmitting body 7 may be prevented from shifting back relative to bracket 6 caused by a human bone or a sharp object abutting against the second light-transmitting body 7. The first light-transmitting body 3 or the hair removing assembly 100 may be prevented from being irrecoverably deformed due to compression. The elastic seal ring 16 may be irrecoverably deformed when being compressed for a plurality of times. In this way, a light guiding effect of the hair removing device may not be affected, and the waste of the light energy may be avoided.

The elastic seal ring 16 further defines a mounting groove 162 communicated with an opening of the inner ring 161. The mounting groove 162 is defined in a side of the elastic seal ring 16 away from the hair removing assembly 100. The inner ring 161 extends from a bottom wall of the mounting groove 162 towards the first light-transmitting body 3. The second light-transmitting body 7 is partially received in the mounting groove 162 to improve a sealing effect between the second light-transmitting body 7 and the elastic seal ring 16, and further to fix the elastic seal ring 16 to the second light-transmitting body 7 to achieve fixed connection between the elastic seal ring 16 and the second light-transmitting body 7.

In some embodiments, the elastic seal ring 16 may include an outer ring 163 and a projection 164 arranged on a side of the outer ring 163. The projection 164 may abut against the first light-transmitting body 3. A side of the outer ring 163 away from the projection 164 defines the mounting groove 162. The inner ring 161 extends from the bottom wall of the mounting groove 162 towards the projection 164. Each of the outer ring 163 and the projection 164 may be a complete closed-loop structure. The light inside the inner ring 161 may only be emitted outwardly from the second light-transmitting body 7.

In some embodiments, a cross section of the projection 164 may be a triangle that is arranged transversely. A contact area between the projection 164 and the first light-transmitting body 3 may be less than a contact area between the projection 164 and the outer ring 163. Therefore, when the elastic seal ring 16 is arranged, an end of the projection 164 away from the outer ring 163 may be partially curled after being compressed. Since the elastic seal ring 16 is elastic, a curled part of the elastic seal ring 16 may tightly abut against the first light-transmitting body 3. That is, when a distance between the first light-transmitting body 3 and the second light-transmitting body 7 changes slightly, the elastic seal ring 16 may be adjusted by taking the curled part to be adaptive to the change in the distance. In this way, tight or even interference fit between the elastic seal ring 16 and the first light-transmitting body 3 and between the elastic seal ring 16 and the second light-transmitting body 7 may be maintained at all times, and a better sealing effect may be achieved. In other embodiments, the cross section of the projection 164 may be trapezoidal.

In the present embodiment, the elastic seal ring 16 may be a ring, made of laser resistant, high temperature resistant and low temperature resistant material, such that when the elastic seal ring 16 is being used, the elastic seal ring 16 may be prevented from being deformed due to high or low temperatures or laser exposure, increasing a service life of the elastic seal ring 16.

Figure 21:
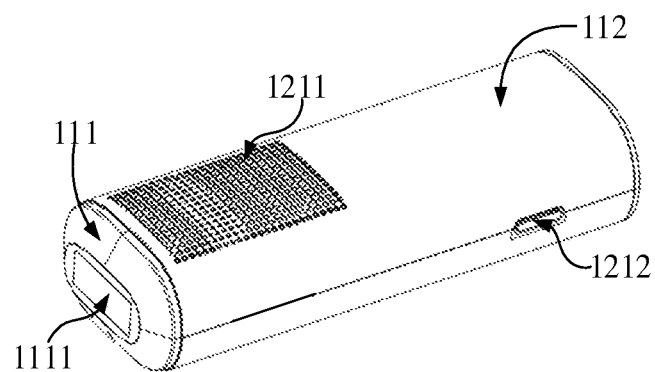
FIG. 21 is a structural schematic view of the device according to another embodiment of the present disclosure.

As shown in FIG. 21, FIG. 21 is a schematic structural view of the hair removing device according to another embodiment of the present disclosure. The hair removing device may include a head portion 111 and a hand-held portion 112 connected to the head portion 111. The head portion 111 is arranged with a cold-compressing portion 1111, configured to attach to the skin. The cold-compressing portion 1111 may emit light to irradiate the hair follicle of the skin. The light may penetrate the skin to irradiate the hair follicle to remove the hair. In addition, the cold-compressing portion 1111 may quickly cool the skin to reduce burning to the skin caused by the light. In this way, while using the hair removing device, the user may be comfortable. In some embodiments, the cold-compressing portion 1111 may emit light for skin care, such that the hair removing device may remove hair and perform skin care at the same time.

In some embodiments, the hand-held portion 112 may include a housing defining a space in a middle (not marked in the drawings). A surface of the housing may define an air vent 1211. The air vent 1211 may be communicated with an inside of the housing and an outside of the housing, such that the hair removing device may exchange air with the outside through the air vent 1211, and a temperature inside the device may be reduced. The housing may further include an interface 1212 configured to connect to an external power supply for charging the hair removing device. A position where the interface 1212 is arranged on the housing is not limited by the present disclosure.

Figure 22:
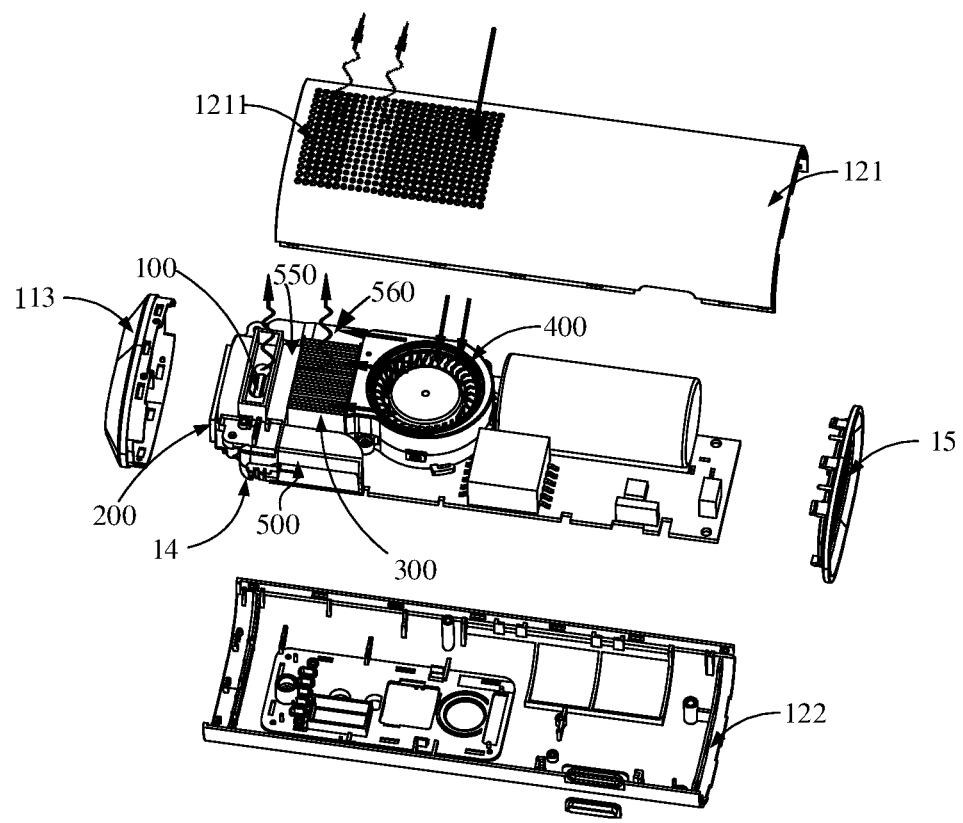
FIG. 22 is an exploded view of the device according to another embodiment of the present disclosure.

As shown in FIG. 21 and FIG. 22, FIG. 22 is an exploded view of the device according to another embodiment of the present disclosure. An arrow in FIG. 22 shows a direction of airflow inside the hair removing device driven by the cold drive assembly. A straight line represents a direction which cold air flows along, and a wavy line represents a direction which hot air flows along. In detail, the hair removing device may include the housing, a light cover 113 arranged over an opening of the housing, a hair removing mechanism 14 received inside the housing and a bottom cover 15.

In the present embodiment, the housing may include a first housing 121 and a second housing 122. The first housing 121 and the second housing 122 may be snapped with each other to define a cavity and two openings at two ends of the housing. The hair removing mechanism 14 is received in the cavity, the light cover 113 and the bottom cover 15 are arranged to cover the two openings respectively to encapsulate the openings defined by the first housing 121 and the second housing 122 after the first housing 121 and the second housing 122 are snapped with each other to define the cavity.

In some embodiments, the first housing 121, the second housing 122, the light cover 113 and the bottom cover 15 may be connected by snaps, screws, bonding, and so on.

The hair removing mechanism 14 may include the hair removing assembly 100, the cold compressing assembly 200, the heat dissipation base 300 and the cold drive assembly 400.

The cold compressing assembly 200 is arranged near the light cover 113. The light cover 113 may define a through hole (not marked in the drawings). A part of the cold compressing assembly 200 is exposed to the outside of the housing through the through hole in the light cover 113 to directly contact the skin. It shall be understood that the part of the cold compressing assembly 200 and the light cover 113 form the head portion 111 of the hair removing device.

The hair removing assembly 100 is arranged on a side of the cold compressing assembly 200 away from the light cover 113 and is configured to emit light to the cold compressing assembly 200. The light may be visible light, such as red light, green light or yellow light. After the light enters the cold compressing assembly 200, the light may pass through the cold compressing assembly 200 to further penetrate the skin to reach the hair follicle under the skin to remove hair.

The heat dissipation base 300 is arranged on a side of the cold compressing assembly 200 and is connected to the cold compressing assembly 200. The cold compressing assembly 200 is able to absorb heat from the skin when attaching to the skin to reduce the temperature of the skin and reduce the burning. A temperature of the cold compressing assembly 200 may be increased when being used for a long period of time, and a cooling effect may be reduced. The heat dissipation base 300 may absorb the heat of the cold compressing assembly 200, such that the cold compressing assembly 200 may keep operating at a low temperature, ensuring the cooling effect that the cold compressing assembly 200 cools the skin. Therefore, the hair removing device in the present embodiment is able to operate constantly at a low temperature when being used continuously, and the user may not hurt.

The cold drive assembly 400 is arranged on a side of at least a part of the heat dissipation base 300 facing away from the hair removing assembly 100 and is configured to dissipate heat from the hair removing assembly 100 and the heat dissipation base 300.

In the present embodiment, the cold drive assembly 400 may absorb an external cooling medium, which passes through the air vent 1211 to enter the inside of the hair removing device. The cooling medium may flow along the hair removing assembly 100 and the heat dissipation base 300 to remove the heat and further flow out of the device through the air vent 1211.

In some embodiments, the external cooling medium may be air. The cold drive assembly 400 may absorb the air and blows the air towards the hair removing assembly 100 and the heat dissipation base 300. Heat of the hair removing assembly 100 and the heat dissipation base 300 may be removed by the airflow.

In the present embodiment, the air vent 1211 may be defined in the first housing 121, and at least part of the cold drive assembly 400 faces the air vent 1211, such that the cold drive assembly 400 may better absorb the external cooling medium, which enters the housing through the air vent 1211, and a heat dissipation efficiency may be improved. In other embodiments, the air vent 1211 may be defined in the second housing 122.

Figure 23:
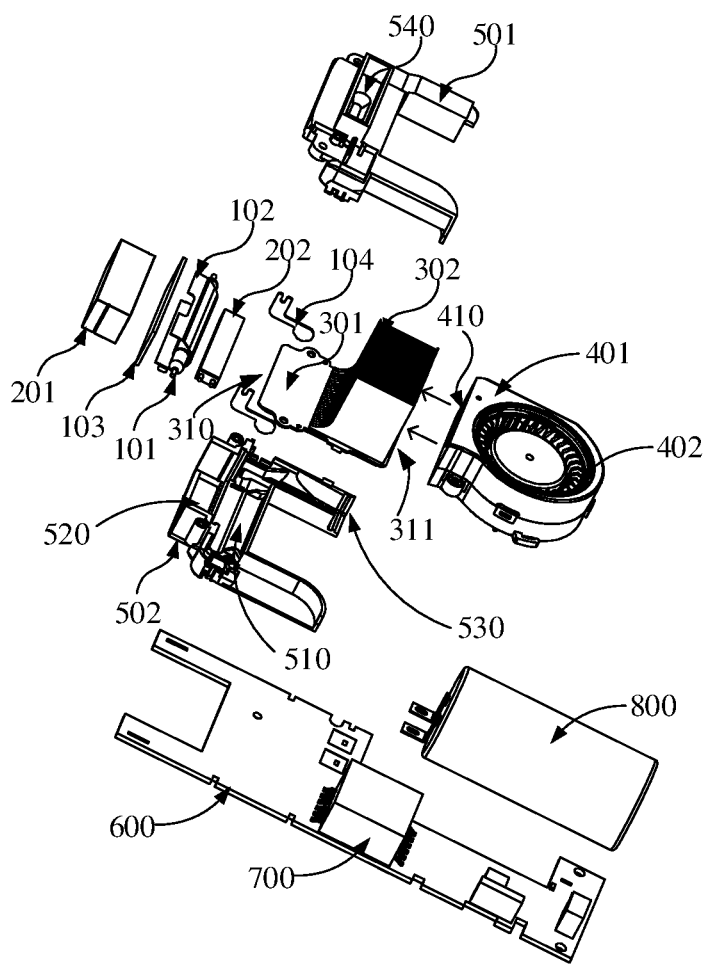
FIG. 23 is an exploded view of the embodiment shown in FIG. 22.

As shown in FIG. 22 and FIG. 23, FIG. 23 is an exploded view of the structure shown in FIG. 22, arrows in FIG. 23 may indicate a direction that air is blown out of a fan.

In the present embodiment, the hair removing device may further include a bracket 500, a circuit board 600, a processor 700 and a capacitor 800. The hair removing assembly 100 and the cold compressing assembly 200 may be arranged inside the bracket 500, and the cold drive assembly 400 may be arranged adjacent to the bracket 500. The hair removing assembly 100, the cold compressing assembly 200 and the cold drive assembly 400 may be mounted on and electrically connected to the circuit board 600.

The processor 700 and capacitor 800 may be electrically connected to and arranged on the circuit board 600. When an external power supply is connected, the external power supply may charge the capacitor 800, such that the capacitor 800 may provide power for the hair removing device. Further, the capacitor 800 may store power when being connected to the external power supply, such that the hair removing device may be used when being not connected to the external power supply. The processor 700 may send control commands to the hair removing assembly 100, the cold compressing assembly 200 and the cold drive assembly 400 to control operation of the hair removing device. For example, the hair removing device may be controlled to be switched on and off, thermal protection of the hair removing device may be controlled, a power of the hair removing device may be adjusted, and so on.

In the present embodiment, the circuit board 600 may be fixed in the second housing 122, and the circuit board 600 may be a PCBA circuit board.

In the art, heat inside the hair removing device may be continuously increased while being used. Circuits and components inside the hair removing device may be exploded, burned, short-circuited, and so on, when being operating at a high temperature. In the present embodiment, the cold drive assembly 400 may dissipate heat from the hair removing assembly 100 and the heat dissipation base 300, and the heat dissipation base 300 may dissipate heat from the cold compressing assembly 200, such that the cold compressing assembly 200 may compress the skin to cool the skin, allowing the skin to feel comfortable, and preventing the components from being exploded, burned, short-circuited, and so on.

In detail, the hair removing assembly 100 may include a light source 101, a reflector 102, a filter 103 and two electrodes 104.

The light source 101, the reflector 102 and the filter 103 are arranged inside the bracket 500, i.e., the bracket 500 is configured with mounting positions for the light source 101, the reflector 102 and the filter 103. The light source 101, the reflector 102 and the filter 103 may be snap into the mounting positions in the bracket 500, correspondingly.

The light source 101 may be opposite to the cold compressing assembly 200. The light emitted from the light source 101 may be directly injected into the cold compressing assembly 200. The reflector 102 may be disposed on a side of the light source 101 away from the cold compressing assembly 200 and may reflect the light of the light source 101 into the cold compressing assembly 200 to prevent a loss of light energy. The filter 103 is disposed between the light source 101 and the cold compressing assembly 200. That is, the light source 101, the filter 103 and the cold compressing assembly 200 may be disposed sequentially in a direction of light propagation. The filter 103 is configured to filter some harmful light out of the light emitted from the light source 101, such that damages to the skin by the light may be reduced, and safety of hair removing may be increased. The two electrodes 104 may be connected on two sides of the light source 101 and may be electrically connected to the circuit board 600 for transmitting electrical signals.

In some embodiments, the light source 101 may be a lamp, a colour of the light emitted by the lamp may not be limited. The lamp may emit coloured light, composite light, and so on. A wavelength and a frequency of the light may be determined based on demands. A type of the lamp is not limited. The lamp may be a xenon semiconductor lamp, a quartz lamp, a laser lamp, and so on. A type of the light may be intense pulse light (IPL), delicate pulse light (DPL), an optimal pulse technology (OPT), an advanced optimal pulse technology (AOPT), broadband light (BBL), and so on. The type of the light may be determined based on desired effects.

In some embodiments, the reflector 102 may be a U-shaped reflector that surrounds the light source 101. Further, an opening of the U-shaped reflector may face the cold compressing assembly 200, and reflect light that does not enter the cold compressing assembly 200 to the cold compressing assembly 200. In addition, the reflector 102 may prevent the heat generated by the light source 101 from transferring to other components of the hair removing device. In the present embodiment, the bracket 500 may include a fixing frame 550 and a tube 560. The fixing frame 550 may define a first receiving space 510 and a second receiving space 520. The first receiving space 510 is configured for receiving the hair removing assembly 100. The second receiving space 520 is configured for receiving the cold compressing assembly 200. The first receiving space 510 may be adjacent to the second receiving space 520 to reduce a distance between the hair removing assembly 100 and the cold compressing assembly 200, reducing a loss of the light emitted from the hair removing assembly 100. The second receiving space 520 may be closer to the head portion 111 of the hair removing device shown in FIG. 21, compared to the first receiving space 510.

When the hair removing device is operating, the light source 101 may generate a large amount of heat, the reflector 102 and the filter 103 may be irradiated by the light, such that a temperature of the reflector 102 and filter 103 may be increased. Therefore, heat of the light source 101, the reflector 102 and the filter 103 needs to be dissipated.

In the present embodiment, the bracket 500 may include the fixing frame 550 and the tube 560. An end of the tube 560 may be connected to a side of the fixing frame 550, and the other end of the tube 560 may extend towards the cold drive assembly 400. The fixing frame 550 defines an air outlet 540 communicated with the first receiving space 510, and the tube 560 defines an air inlet 530 communicated with the first receiving space 510. The air inlet 530, the first receiving space 510 and the air outlet 540 may be sequentially communicated with each other.

The air inlet 530 may be connected to the cold drive assembly 400. The air outlet 540 may be communicated with the air vent 1211. The cold drive assembly 400 may absorb the external air from the air vent 1211 and blow the air towards the air outlet 540. The air enters the first receiving space 510 through the air outlet 540 and carries the heat away from the light source 101, the reflector 102 and the filter 103 in the first receiving space 510. Further, the air may flow out the device through the air outlet 540 and the air vent 1211 to dissipate the heat.

In some embodiments, a part of the fixing frame 550 and a part of the tube 560 form a first bracket 501, and the remaining part of the fixing frame 550 and the remaining part of the tube 560 form a second bracket 502. In other embodiments, the fixing bracket 550 may be configured as an integral one-piece structure.

The first bracket 501 and the second bracket 502 may be connected to each other through a snap. The first bracket 501 may be disposed near the first housing 121, and the second bracket 502 may be disposed near the second housing 122. The air outlet 540 may be defined in the first bracket 501 and may be opposite to the air vent 1211 in the first housing 1211 to increase the heat dissipation efficiency at the air outlet 540. The first receiving space 510 may be defined in a part of the first bracket 501 and a part of the second bracket 502.

The part of the first bracket 501 and the part of the second bracket 502 may correspond to the fixing frame 550 and may be snapped with each other. The air inlet 530 may be defined in another part of the first bracket 501 and another part of the second bracket 502. The another part of the first bracket 501 and the another part of the second bracket 502 may correspond to the tube 550 and may be snapped with each other. The air inlet 530 may be communicated with the first receiving space 510 and connected to the cold drive assembly 400. An inside of the bracket 6 may define a channel for guiding an airflow, facilitating the airflow of the cold drive assembly 400 to be guided into the first receiving space 510.

Therefore, in the present embodiment, the hair removing assembly 100 may dissipate heat through the cold drive assembly 400, ensuring the hair removing device to be used safely.

Further, in the present embodiment, the cold compressing assembly 200 may include a second light-transmitting body 201 and a refrigerating member 202.

The second light-transmitting body 201 may be configured to attach to the skin. The second light-transmitting body 201 may face the light source 101. The second light-transmitting body 201 may be an element allowing the light to pass through. The light emitted by the light source 101 enters the second light-transmitting body 201 and passes through the second light-transmitting body 201 to further reach the skin.

In some embodiments, the second light-transmitting body 201 may be a light conductive crystal, such as sapphire, K9 glass or crystal glass. When the second light-transmitting body 201 is the sapphire, the second light-transmitting body 201 may have excellent thermal conductivity.

In some embodiments, the second light-transmitting body 201 may be cylindrical or cuboid. A face of the second light-transmitting body 201 away from the light source 101 may be configured to attach the skin.

The refrigerating member 202 may be connected to the second light-transmitting body 201 to absorb heat from the second light-transmitting body 201. Since the temperature of the second light-transmitting body 201 is increased when the second light-transmitting body 201 contacts the skin, the refrigerating member 202 may absorb the heat of the second light-transmitting body 201 after the temperature of the second light-transmitting body 201 is increased, such that the second light-transmitting body 201 remains cold, and when the second light-transmitting body 201 is contacting the skin for a long period of time, the second light-transmitting body 201 may still cool the skin, and the burning sensation to the skin may be reduced.

Further, the refrigerating member 202 may be a semiconductor refrigerating member. An end of the refrigerating member 202 that absorbs heat may be connected to the second light-transmitting body 201, and the other end of the refrigerating member 202 may dissipate the heat.

In order to dissipate heat from the heat dissipating end of the refrigerating member 202, in the present embodiment, the heat dissipation base 300 is connected to the heat absorbing end of the refrigerating member 202 and absorbs the heat from the refrigerating member 202.

In detail, the heat dissipation base 300 may include a heat dissipation plate 301 and a heat dissipation wing 302. A surface of the heat dissipation plate 301 includes a first region 310 and a second region 311 side by side. The hair removing assembly 100 is arranged in the first region 310, and the heat dissipation wing 302 is arranged in the second region 311. The second region 311 is arranged on a side of the fixing frame 550 connected to the tube 560. The heat dissipation wing 302 and the tube 560 are disposed side by side on a side of the fixing frame. The fixing frame 550 is arranged in the first region 310. The heat dissipation plate 301 is arranged on the circuit board 600 and is connected to the cold compressing assembly 200. In detail, the refrigerating member 5 may be bonded to the heat dissipation plate 301 by a thermally-conductive silicone grease. The cold compressing assembly 200 may quickly transfer the heat to the heat dissipation plate 301 through the thermally-conductive silicone grease. The heat dissipation wing 302 may dissipate heat from the heat dissipation plate 301 and assist the heat dissipation plate 301 to dissipate the heat, such that the heat dissipation plate 301 may continuously absorb heat from the refrigerating member 202.

In some embodiments, the number of heat dissipation wings 302 may be more than one. The more than one heat dissipation wings 302 may be parallel to each other and may be mounted on the heat dissipation plate 301 by welding.

In some embodiments, a surface of the heat dissipation wing 302 may be sprayed with a heat-conductive paint. The heat-conductive paint may radiate to dissipate the heat away from the heat dissipation wing 302, and may prevent the heat dissipation wing 302 from being affected by water, being corroded and being worn.

In the present embodiment, the heat dissipation plate 301 may be a temperature homogeneous plate. When a liquid inside the temperature homogeneous plate encounters an environment at a high temperature, the liquid may absorb heat and may be vaporized into gas. When the gas encounters an environment at a low temperature, the gas may dissipate heat and may be liquified into the liquid. Therefore, a temperature of a surface of the temperature homogeneous plate may be kept homogeneous due to periodic evaporation and condensation. Therefore, a part of the surface of the heat dissipation plate 301 is connected to the refrigerating member 5, and the other part is connected to the heat dissipation wing 302, such that the heat generated by the refrigerating member 202 may be dissipated through the heat dissipation plate 301 and the heat dissipation wing 302.

Figure 24:
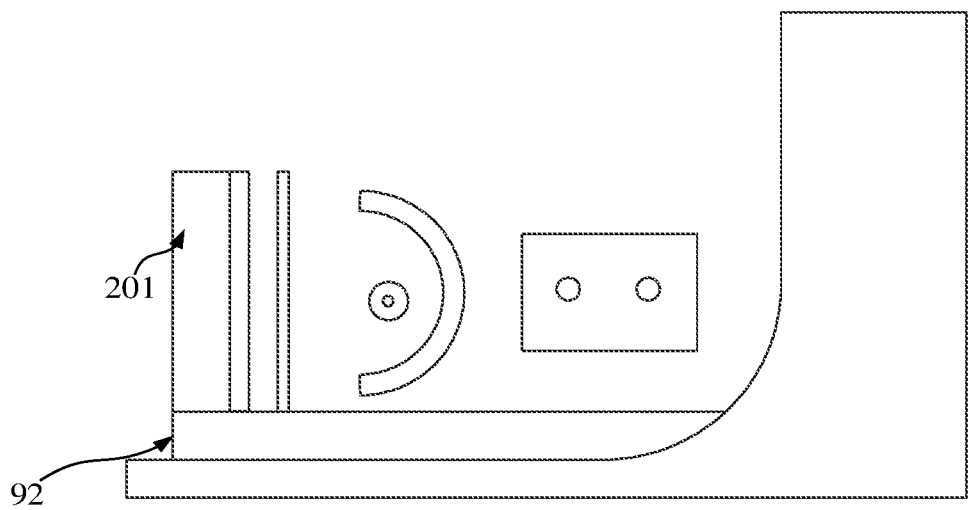
FIG. 24 is a structural schematic view of a carbon-containing layer according to another embodiment of the present disclosure.

In some embodiments, as shown in FIG. 24, the carbon-containing layer 92 may be disposed between the second light-transmitting body 201 and the heat dissipation base 300, such as on a surface of the heat dissipation plate 301 thermally coupling with the second light-transmitting body 201. The carbon-containing layer 92 has excellent thermal conductivity, and may accelerate a thermal conducting rate of the heat dissipation plate 301 and improve heat dissipation performance of the heat dissipation base 300.

In some embodiments, the carbon-containing layer may be a graphene material, graphite powder, a graphite sheet or a graphite film.

In some embodiments, the carbon-containing layer may be arranged by plating, spraying or attaching.

In order to improve the heat dissipation performance of the heat dissipation base 300, in the present embodiment, the heat dissipation base 300 may further be connected to the cold drive assembly 400.

In detail, the heat dissipation wing 302 of the heat dissipation base 300 may be connected to the cold drive assembly 400. The cold drive assembly 400 may absorb the external air through the air vent 1211 and drive the air to flow towards the heat dissipation wing 302. The air may flow along the heat dissipation wing 302 to dissipate heat from the heat dissipation wing 302.

In an example, the heat dissipation wing 302 may be arranged parallel to an airflow direction driven by the cold drive assembly 400 to increase a contact area between the heat dissipation wing 302 and the airflow, increasing the efficiency of dissipating heat from the heat dissipation wing 302.

The heat dissipation wing 302 may face the air vent 1211 in the first housing 121. The airflow, after flowing along the heat dissipation wing 302, may quickly flows out of the device through the air vent 1211.

Therefore, the cold drive assembly 400 of the present embodiment may drive the cooling medium to dissipate heat from the hair removing assembly 100, and may further dissipate heat from the heat dissipation base 300. With improved safety, the irradiated skin may be compressed to be cooled, and burning of the irradiated skin may be reduced. Further, the cold compressing assembly 200 may be controlled by the heat dissipation base 300 and the cold drive assembly 400 to reach a low temperature of about zero degrees. In this way, the skin near a light outlet port may infinitely approach a freezing point, burning sensation of the skin may be reduced, and a short contact between the skin the device may not cause damage to the skin.

Figure 25:
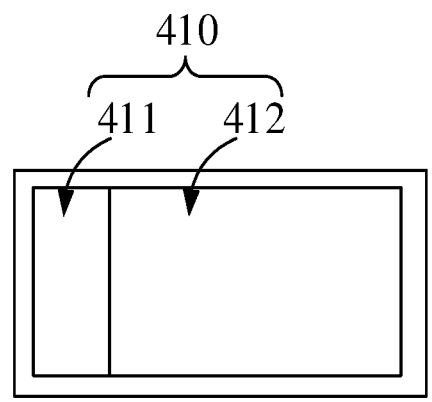
FIG. 25 is a structural schematic view of an air outlet of a fan housing of the embodiment shown in FIG. 23.

As shown in FIG. 22, FIG. 23 and FIG. 25, FIG. 25 is a structural schematic view of an air outlet of a fan housing of the embodiment shown in FIG. 23. In the present embodiment, the cold drive assembly 400 may include a fan housing 401 and a fan 402. The fan housing 401 is arranged on a side of the heat dissipation base 300 away from the cold compressing assembly 200, and the fan 402 is received inside the fan housing 401.

An air inlet end of the fan 402 faces the air vent 1211 in the first housing 121. The fan 402 drives the external air to flow into the fan 402 through the air vent 1211. The fan housing 401 defines an air outlet 410 for outputting air. An air outlet end of the fan 402 is connected to the air outlet 410. The fan 402 drives the external air to flow into the fan 402 through the air vent 1211 and further drives the air to flow out through the air outlet 410.

In some embodiments, the fan 402 may be a centrifugal fan, an axial flow fan, a mixed flow fan or a cross flow fan.

Further, the air outlet 410 may include a first air outlet 411 and a second air outlet 412. Air at the air outlet 410 of the fan 402 may be divided into two parts. One of the two parts of the air flows out of the device through the first air outlet 411, and the other one of the two parts of the air flows out of the device through the second air outlet 412.

In some embodiments, the air outlet 410 may further include a third air outlet or more air outlets. The present disclosure does not limit the number of the air outlets.

In the present embodiment, the first air outlet 411 is communicated with the air inlet 530 of the bracket 500. The fan 402 drives the external air to enter the fan 402 through the air vent 1211. The fan 402 drives the air to flow from the first air outlet 411 and the air inlet 530 into the first receiving space 510. The air in the first receiving space 510 may carry the heat away from the light source 101, the reflector 102 and the filter 103. Finally, the air flows out of the device from the air outlet 540 and the air vent 1211. In this way, heat is dissipated to the outside of the device, enabling the heat of the hair removing assembly 100 to be dissipated.

In the present embodiment, the second air outlet 412 is connected to the heat dissipation wing 302 of the heat dissipation base 300. The fan 402 drives the external air to enter the fan 402 from the air vent 1211. The fan 402 drives the air to flow between every two of the more than one heat dissipation wings 302 of the heat dissipation base 300 through the second air outlet 412. The air flows along the heat dissipation wings 302, carries the heat away from the heat dissipation wings 302, and further flows out of the device from the air vent 1211. After temperatures of the heat dissipation wings 302 are decreased, the heat of the heat dissipation plate 301 may be decreased accordingly. In this way, the heat dissipation plate 301 may absorb the heat of the cold compressing assembly 200, enabling the heat of the cold compressing assembly 200 to be dissipated.

In some embodiments, the amount of the air flowing in the first air outlet 411 and the second air outlet 412 will not be limited herein and may be determined based on demands. The amount of the air flowing in the first air outlet 411 and the second air outlet 412 may be controlled by configuring a size of the first air outlet 411 and a size pf the second air outlet 412. For example, in the present embodiment, an air outlet area of the second air outlet 412 is greater than an air outlet area of the first air outlet 411, such that a larger amount of air flows through the second air outlet 412 to enhance the efficiency of dissipating the heat from the heat dissipation plate 301.

According to the above embodiments, in the hair removing device of the present embodiment, heat of the hair removing assembly 100, the cold compressing assembly 200 and the heat dissipation base 300 may be dissipated by the cold drive assembly 400, such that heat of the hair removing assembly 100 and the cold compressing assembly 200 may be dissipated simultaneously. The heat dissipation performance of the hair removing device may be improved, and the safety of the hair removing device may be improved. In addition, the skin may be compressed to be cooled continuously, and the temperature of the skin may infinitely approach the freezing point, such that the burning sensation of the skin may be reduced, and the skin may be prevented from being damaged while the hair is being removed.

Figure 31:
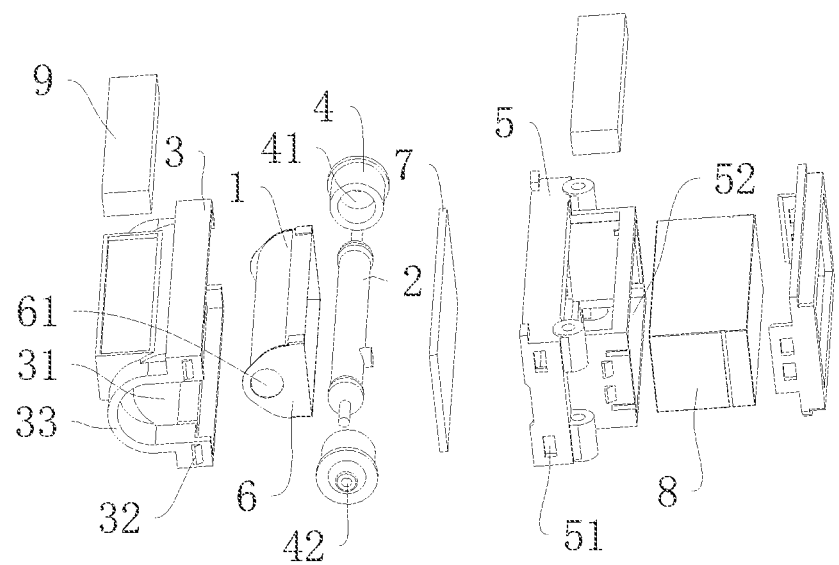
FIG. 31 is an exploded view of a hair removing device according to an embodiment of the present disclosure.

As shown in FIG. 31, the hair removing device includes the reflector 1 and the light source 2. The reflector 1 may be a conductor. When power is supplied to the device, a strong electric field may be generated. The light source 2 is arranged inside the reflector 1 and is opposite to the reflector 1. The light source 2 may be a strip-shaped gas excitation light source and may be excited by the reflector 1 to emit light after the reflector 1 is conducted. The reflector 1 has a light exiting side. The reflector 1 may reflect the light, and the light may be emitted from the light exiting side of the reflector 1. A distance between a body of the light source 2 and the reflector 1 is greater than zero and less than or equal to 0.3 mm. For example, in an embodiment of arranging the light source 2, the distance between the body of the light source 2 and the reflector 1 may be 0.3 mm; or the distance between the body of the light source 2 and the reflector 1 may be 0.15 mm. Similarly, the distance between the light source 2 and the reflector 1 may be determined based on a structure of the reflector 1 and a structure of the light source 2, allowing the distance between the body of the light source 2 and the reflector 1 to be less than 0.3 mm.

When the hair removing device is operating, and when the reflector 1 is conducted, a high electric field may be generated in the reflector 1. A high voltage generated by the reflector 1 may ionize gas in the light source 2 to generate an arc light for discharging. That is, the light source 2 may emit light. By defining the distance between the light source 2 and the reflector 1, the voltage in the reflector 1 may excite the light source 2 to emit light. By contrast to taking a triggering line to trigger the lamp to emit light, in the present embodiment, the reflector 1 triggers the lamp to emit light without the triggering line. In this way, the way of triggering the lamp to emit light may be improved, material for production may be reduced, and production costs may be reduced.

In some embodiments, the reflector 1 is a semi-arc reflector 1. The light source 2 may be a strip-shaped lamp. The lamp is suspended inside the reflector 1. In this way, the body of the lamp and an inner wall of the reflector 1 cooperatively define an excitation space. The voltage in the reflector 1 may excite the lamp without the triggering line. The gas inside the lamp may be ionized, such that the lamp may emit light. The reflector 1 may trigger the lamp to emit light by the high voltage, and in addition, the reflector 1 may serve as a mounting carrier for the light source 2. In this way, the triggering line or other components to excite the lamp to emit light may be omitted, production material may be saved, and production costs may be reduced. In addition, the number of components arranged inside the reflector 1 may be reduced, and an occupation space may be saved, enabling the reflector 1 to reflect the light emitted from the light source 2 to the outside, improving a light emission rate.

In some embodiments, the reflector 1 may be strip shaped.

Figure 32:
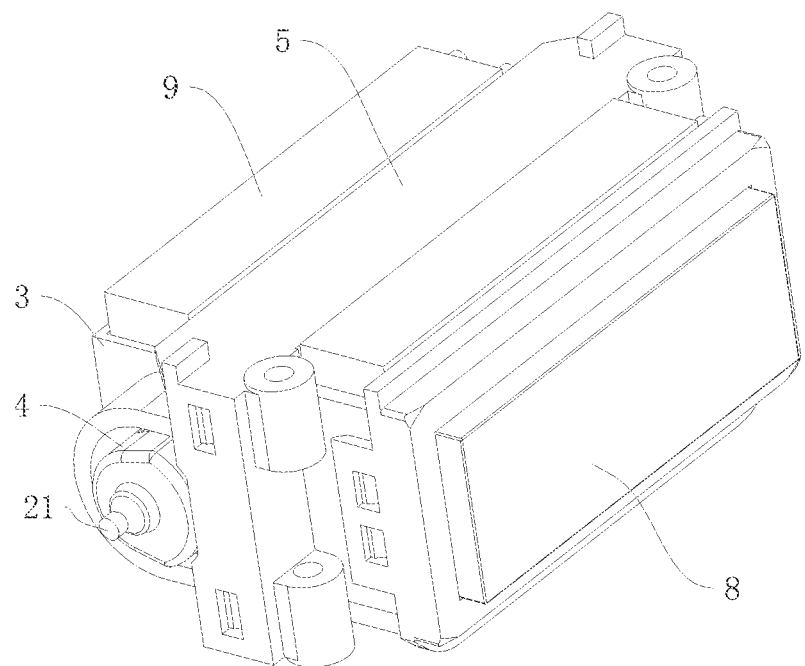
FIG. 32 is an assembled view of a hair removing device according to an embodiment of the present disclosure.

As shown in FIG. 31 and FIG. 32, in some embodiments, the hair removing device includes the heat sink 3, an elastic member 4 and the bracket 5. The heat dissipation base 3 may be strip shaped. The reflector 1 is arranged on the heat dissipation base 3. The light exiting side of the reflector 1 is away from the heat dissipation base 3. A side of the heat dissipation base 3 contacting the reflector 1 is thermally coupled to the reflector 1. The elastic member 4 is fixed to an end of the light source 2 and is configured to movably fix the light source 2 on the reflector 1. The elastic member 4 is arranged on each of two sides of the reflector 1 along a length of the reflector 1. The bracket 5 is fixedly connected to the heat dissipation base 3 by snaps. The elastic member 4 is disposed between the heat dissipation base 3 and the bracket 5. The bracket 5 abuts against the elastic member 4 in a direction perpendicular to the length of the light source 2, such that the light source 2 is fixed relative to the reflector 1 or the heat dissipation base 3. The heat dissipation base 3 and bracket 5 cooperatively fix the reflector 1 fixed, such that the light source 2 may be stably arranged on the reflector 1. The heat dissipation base 3 and the bracket 5 may be arranged to ensure the stability of the hair removing device. The elastic member 4 has good elasticity. When the bracket 5 abuts against the elastic member 4, the elastic member 4 may be deformed easily. In this way, on one hand, the light source 2 and the reflector 1 may not be easily shaking relative to each other, a light emission effect may be improved. On the other hand, the elastic member 4 may cushion a pressure that the bracket 5 applies to the end of the light source 2. The elastic member 4 may contact the end of the light source 2 flexibly, such that damages to the light source 2 may be reduced effectively, and the service life of the light source 2 may be extended.

Figure 33:
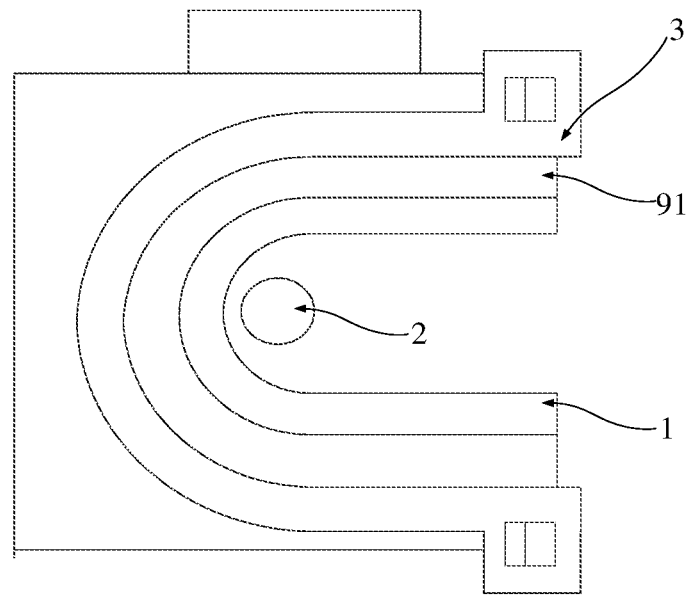
FIG. 33 is a structural schematic view of a carbon-containing layer according to an embodiment of the present disclosure.

In some embodiments, as shown in FIG. 33, the hair removing device may further include a carbon-containing layer 91, arranged in the reflector 1. For example, the carbon-containing layer 91 may be arranged on a side of the reflector 1 away from the light source 2. The light source 2 may generate heat while in use, and the heat may be accumulated in the reflector 1. The carbon-containing layer 91 has excellent thermal conductivity, and therefore, a thermal conducting rate of the reflector 1, which is arranged with the carbon-containing layer 91, may be increased, and heat dissipation performance of the reflector 1 may be enhanced. The hair removing device may be prevented from being damaged due to the high temperature, and the skin of the user may be prevented from being irritated or damaged.

In some embodiments, the carbon-containing layer 91 is arranged on the heat dissipation base 3. For example, the carbon-containing layer 91 may be disposed between the heat dissipation base 3 and the reflector 1 to accelerate a thermal conductivity rate between the heat dissipation base 3 and the reflector 1.

In some embodiments, the carbon-containing layer 91 may be arranged on an exposed surface of the heat dissipation base 3 to enhance heat dissipation performance of the heat dissipation base 3.

In some embodiments, the carbon-containing layer 91 may be made of graphene, graphite powders, a graphite sheet, a graphite film, and the like, and may be arranged at any available position as described in the present disclosure by plating, spraying, attaching, and so on.

In some embodiments, the heat dissipation base 3 may be a ceramic base. The ceramic base is configured with a first groove body 31. The reflector 1 is embedded in the first groove body 31. The first groove body 31 is strip shaped, and a bottom of the groove body 31 may has be a curved section. The reflector 1 is embedded in the first groove body 31. On one hand, a contact area between the reflector 1 and the heat dissipation base 3 is increased, the heat dissipation base 3 takes the thermal conductivity to dissipate heat from the reflector 1, reducing heat radiation of the entire hair removing device. On the other hand, the first groove body 31 is arranged on the heat dissipation base 3. Space utilization of the heat dissipation base 3 may be improved, components inside the hair removing device may be arranged more compactly. In addition, the ceramic is an insulator, a short circuit may not occur when the ceramic base contacts the reflector 1. The reflector 1 is the conductor and is spaced apart from the light source 2, such that a strong electric field is generated when power is supplied and excites the light source 2 to emit light. Therefore, the body of the light source 2 is suspended in the cavity of the reflector 1.

In some embodiments, each of two sides of the heat dissipation base 3 is arranged with a first fastening portion 32, and the first fastening portion 32 and the heat dissipation base 3 may be configured as an integral one-piece structure. Each of two sides of the bracket 5 is arranged with a second fastening portion 51, and the second fastening portion 51 and the bracket 5 may be configured as an integral one-piece structure. The first fastening portion 32 may correspond to the second fastening portion 51. In the process of connecting the heat dissipation base 3 with the bracket 5, the first fastening portion 32 may be tightly fastened with the second fastening portion 51. In this way, the heat dissipation base 3 and the bracket 5 may be connected together stably, enhancing stability of the hair removing device. In some embodiments, the first fastening portion 32 may be a buckle block or a cantilever hook, and the second fastening portion 51 may be a fixing hole. While connecting the heat dissipation base 3 with the bracket 5, the cantilever hook may be received into the fixing hole. Further, after the cantilever hook is received in the fixing hole, a wall of the fixing hole may restrict the cantilever hook, preventing the cantilever hook from easily leaving out of the fixing hole. In this way, the first fastening portion 32 and the second fastening portion 51 may be stably connected, i.e., the heat dissipation base 3 and the bracket 5 may be fixed with each other, effectively preventing the heat dissipation base 3 from being loosed from or falling off from the bracket 5, and improving the stability of the hair removing device.

In some embodiments, the bracket 5 defines a window 52. A size of a part of the window 52 corresponding to the second fastening portion 51 is greater than a size of a part of the ceramic base arranged with the first fastening portion 32, such that the part of the ceramic base arranged with the first fastening portion 32 is embedded in the window 52 of the bracket 5. In the process of assembling the ceramic base with the bracket 5, a side of the ceramic base near the bracket 5 may be embedded in the window 52, such that connection between the ceramic base and the bracket 5 may be more stable. In addition, a gap between the ceramic base and the bracket 5 may be reduced, heat, which is in the reflector 1 and may be radiated to an edge of the reflector 1, may be reduced, such that the performance of the hair removing device may be improved.

Figure 34:
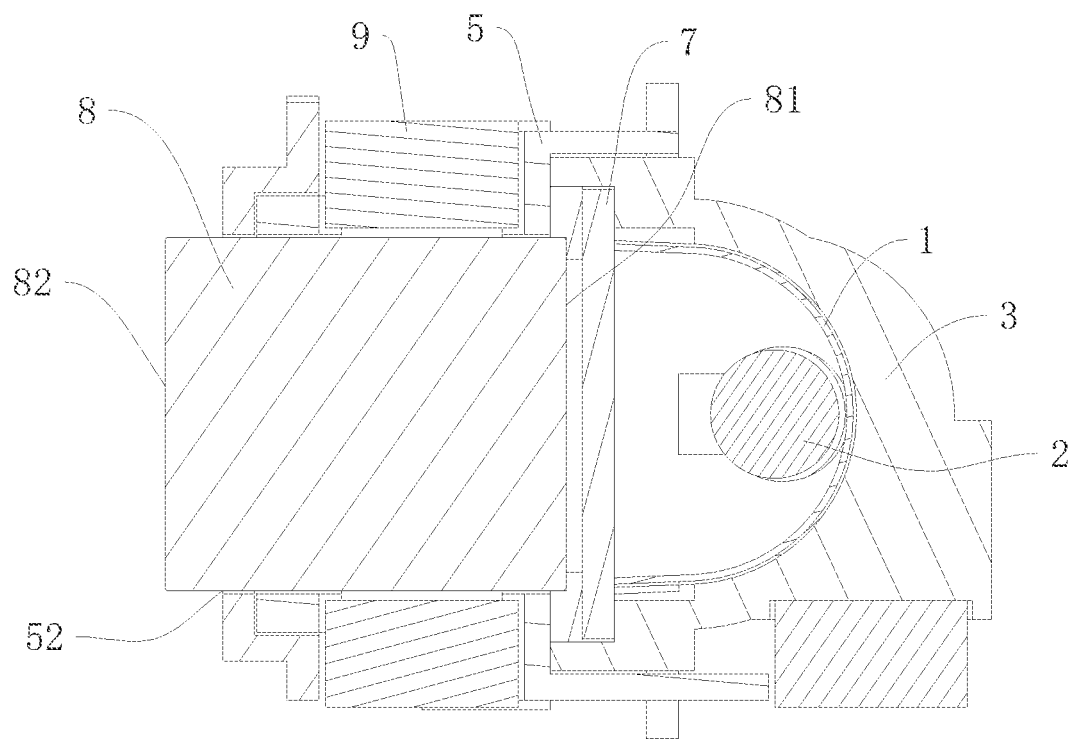
FIG. 34 is a cross sectional view showing a hair removing device according to an embodiment of the present disclosure.

As shown in FIG. 31, FIG. 32 and FIG. 34, the hair removing device may further include a side reflecting member 6, arranged on each of two ends of the reflector 1 along a length direction of the reflector 1. The side reflecting member 6 may reflect light, which escapes from the two ends of the reflector 1, onto the light exiting side of the reflector 1. The side reflecting member 6 fully reflects the light emitted by the light source 2 in order to improve the light utilization rate.

In some embodiments, the side reflecting member 6 defines a through hole 61. A diameter of the through hole 61 is greater than a diameter of the end of the lamp. The end of the lamp may pass through the through hole 61. While arranging the lamp, the lamp may pass through any one of two through holes 61 of two side reflecting members 6. Alternatively, the lamp may pass through the through hole 61 from the inside of the reflector 1, such that the lamp may be arranged easily. In some embodiments, the elastic member 4 may be a silicone cover or a soft rubber cover. In the present embodiment, the silicone cover may be taken as an example for illustration, but the present disclosure does not limit detailed material of the elastic member 4. The light source 2 may be a lamp, and the lamp may be strip shaped and cylindrical. Each of the two ends of the lamp is arranged with a mounting post 21 extending from the lamp. A radius of the mounting post 21 is less than a radius of the lamp. In detail, the silicone cover may be cylindrical and defines a mounting slot 41. The two ends of the lamp may be embedded into the mounting slot 41. The silicone cover defines a fixing hole 42 along an axis of the cover. The fixing hole 42 is communicated with the mounting slot 41. The mounting post 21 may pass through the fixing hole 42.

By defining the through hole 61, the lamp may be precisely arranged on the reflector 1, reducing time spent on arranging the lamp, such that an arrangement efficiency may be improved. When the reflector 1 and the lamp are assembled, an opening of the mounting slot 41 faces the reflector 1, and the two ends of the lamp are inserted into the mounting slot 41 by passing through the two through holes 61 respectively. The silicone cover elastically abuts the lamp to a wall of the through hole 61 near the bottom of the reflector 1, reducing a rigid contact between the lamp and the side reflecting member 6, and minimizing collision between the side reflecting member 6 and the lamp. Even if the side reflecting member 6 collides the lamp, the silicone cover may cushion the colliding force, effectively extending the service life of the lamp and reducing the usage costs.

As shown in FIG. 31, FIG. 32 and FIG. 34, two ends of the ceramic base arranged with the first groove body 31 are further arranged with two second groove bodies 33 respectively. The second groove bodies 33 are configured to receive two ends of the light source 2 and the corresponding elastic members 4. On one hand, spaces are saved, and space utilization of the ceramic base may be improved. On the other hand, the second groove body 33 reduces collision applied to the end of the light source 2 and the elastic member 4 by any foreign object. Inner spaces of the second groove bodies 33 and an inner space of the first groove body 31 are communicated. A depth of the second groove body 33 is greater than a depth of the first groove body 31. The second groove body 33 defines the space for receiving an elastic deformation amount of the elastic member 4, such that the elastomer 4 may not compress with a wall of the second groove body 33, enabling the elastic member 4 to be easily deformed. The elastic member 4 may be deformed based on the actual situation. While the elastic member 4 is being deformed, the elastic member 4 may cushion the external force, such that the mounting post 21 may not be easily damaged or shattered, reducing the number of times of replacing the light source 2, reducing the usage cost, and improving the practicality of the hair removing device.

As shown in FIG. 31, FIG. 32 and FIG. 34, in some embodiments, the hair removing device may include a first light-transmitting body 7, arranged on the light exiting side of the reflector 1 and fixed to the bracket 5. The first light-transmitting body 7 and the reflector 1 cooperatively define a cavity for receiving the light source 2. The first light-transmitting body 7 may be a filter. The filter 7 may filter the light to select the light having a wavelength suitable for removing the hair from the skin. In this way, while the hair removing device is operating, and when the light source 2 is irradiating on the skin, damages to the skin caused by the light may be reduced, and the safety of removing the hair may be improved.

In some embodiments, the hair removing device may include a second light-transmitting body 8. The second light-transmitting body 8 may be square or rectangular and may be embedded in the window 52. The second light-transmitting body 8 is disposed on a side of the filter facing away from the light source 2. The second light-transmitting body 8 has a light incidence surface 81 facing the light source 2 and a light exiting surface 82 facing away from the light source 2. In some embodiments, the second light-transmitting body 8 may be a crystal. The second light-transmitting body 8 may alternatively be a diamond. In the present embodiments, the second light-transmitting body 8 being the crystal may be taken as an example. While the hair removing device is operating, the light source 2 emits light, and the light is reflected by the reflector 1. Further, the light passes through the filter and is reflected to reach the crystal. The light enters the crystal from the light incidence surface 81. The light may be reflected by the crystal itself and exits the crystal from the light exiting surface 82. The light emitted from the light exiting surface 82 may irradiate a skin area that has the hair to be removed to remove the hair.

In some embodiments, the hair removing device includes a refrigerating member 9. A refrigerating side of the refrigerating member 9 may be thermally coupled to the other side of the heat dissipation base 3 to cool down the space inside the reflector 1. For example, the refrigerating element 9 may be, such as, a TEC refrigerating shell or a refrigerating block. The refrigerating member 9 may cool the heat dissipation base 3 to remove the heat from the heat dissipation base 3 timely and quickly, such that the reflector 1 may be cooled quickly. In the present embodiment, the refrigerating member 9 may be the TEC refrigerating sheet and will illustrated as an example in the following. The present disclosure does not limit detailed structure of the refrigerating member 9.

While the hair removing device is operating, the light source 2 in the reflector 1 emits a large amount of light, and heat generated by the light may be collected in the cavity. In addition, the temperature of the reflector 1 may be increased as the heat is collected in the cavity. A side of the heat dissipation base 3 is thermally coupled to the reflector 1, and the other side of the heat dissipation base 3 is thermally coupled to the refrigerating member 9. The thermal coupling may be achieved by any one or combination of heat transfer, thermal convection and thermal radiation. That is, the heat of the reflector 1 may be dissipated through the heat dissipation base 3, and the heat in the cavity may be dissipated, such that the reflector 1 and the cavity may be cooled down, and the efficiency of dissipating the heat from the light source 2 may be improved. By configuring the body of the light source 2 to be suspended in the cavity, the heat of the light source 2 may be dissipated more uniformly, and the service life of the light source 2 may be improved. In detail, the heat generated while the light source 2 is operating may be dissipated by radiating towards all directions. In addition, the air is evenly distributed around the light source 2, the air may fully contact the light source 2 and may evenly dissipate the heat generated by the light source 2. The heat may be generated by the light source 2, transferred through the cavity to the reflector 1 and the first light-transmitting body 7, and then dissipated out of the device. In addition, the refrigerating member 9 may further transfer the heat from the heat dissipation base 3 to achieve rapid heat dissipation, such that the heat dissipation effect of the hair removing device may be improved. In addition, the heat in the cavity that may be transferred to other components of the hair removing device may be reduced. While the hair removing device is operating, the burning sensation at the skin that has hair to be removed may be reduced, and the performance of the hair removing device may be improved.

In some embodiments, a carbon-containing layer may be arranged on a side of the refrigerating member 9 facing the heat dissipation base 3 or an exposed surface of the refrigerating member 9. The carbon-containing layer 91 has excellent thermal conductivity. Therefore, the refrigerating effect of the refrigerating member 9 may be improved, such that heat of the heat dissipation base 3 may be dissipated timely and rapidly, and the reflector 1 may be cooled quickly.

According to the above embodiments, a hair removing device is provided and includes the reflector 1 and the light source 2. The light source 2 is a strip-shaped gas excitation light source and is arranged on the reflector 1. The distance between the body of the light source 2 and the reflector 1 is less than or equal to 0.3 mm. Therefore, after power is supplied to the reflector 1, the reflector 1 produces a high voltage to ionize the gas in the light source 2 to produce arc light to discharge, such that the light source 2 may emit light. The reflector 1 is a conductor and defines a space where the high voltage may be generated. By defining the distance between the light source 2 and the reflector 1, the voltage in the reflector 1 may excite the light source 2 to emit light. By contrast to taking a triggering line to trigger the lamp to emit light, in the present embodiment, the reflector 1 triggers the lamp to emit light without the triggering line. In this way, the way of triggering the lamp to emit light may be improved, material for production may be reduced, and production costs may be reduced.

Figure 35:
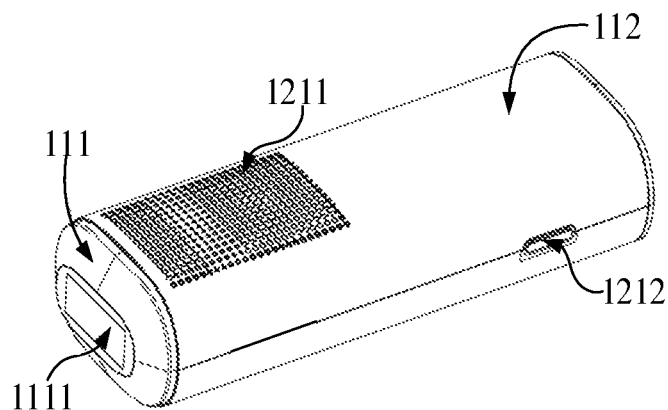
FIG. 35 is a structural schematic view of a hair removing device according to another embodiment of the present disclosure.

As shown in FIG. 35, FIG. 35 is a schematic structural view of the hair removing device according to an embodiment of the present disclosure. The hair removing device may include a head portion 111 and a hand-held portion 112 connected to the head portion 111. The head portion 111 is arranged with a cold-compressing portion 1111, configured to attach to the skin. The cold-compressing portion 1111 may emit light to irradiate a hair follicle of the skin. The light may penetrate the skin to irradiate the hair follicle to remove the hair. In addition, the cold-compressing portion 1111 may quickly cool down the skin to reduce burning to the skin caused by the light. In this way, while using the hair removing device, the user may be comfortable. In some embodiments, the cold-compressing portion 1111 may emit light for skin care, such that the hair removing device may remove hair and perform skin care at the same time.

Figure 40:
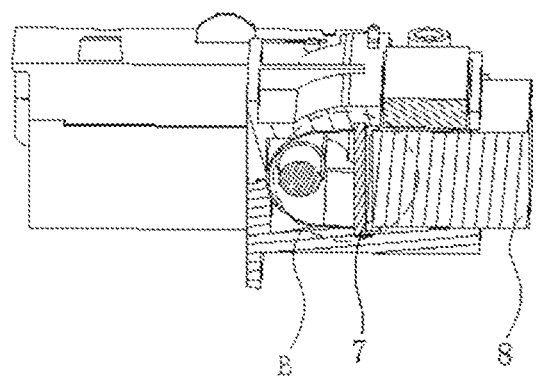
FIG. 40 is a cross sectional view showing the entire structure of the device according to another embodiment of the present disclosure.
Figure 41:
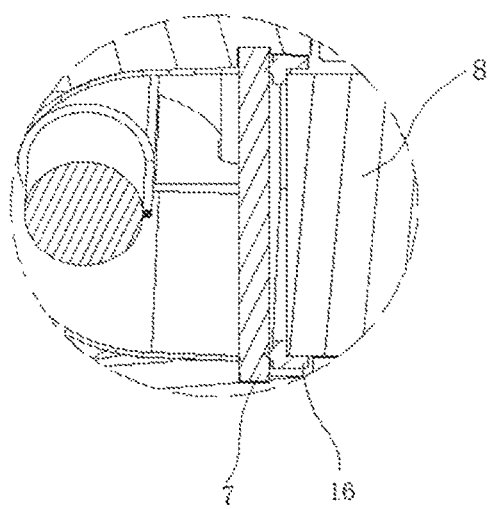
FIG. 41 is an enlarged view of a portion B shown in FIG. 40.

As shown in FIG. 40 and FIG. 41, for the hair removing device in another embodiment, an elastic seal ring 16 is disposed between the first light-transmitting body 7 and the second light-transmitting body 3. The elastic seal ring 16 may be ring-shaped. The first light-transmitting body 7 and the second light-transmitting body 3 may be sealed with the elastic seal ring 16. In this way, water condensation may not be generated between the second light-transmitting body 3 and the first light-transmitting body 7. Dirt may not penetrate into the connection between the second light-transmitting body 3 and the first light-transmitting body 7. The elastic seal ring 16 may be preferably ring-shaped.

Of course, when the hair removing device falls to the ground, the second light-transmitting body 3 may rigidly collide with the ground. A conventional light-transmitting body 3 may transfer a colliding impact to the first light-transmitting body 7, such that the first light-transmitting body 7, the reflector 1 and the light source 2 may be vibrated and damaged. For the hair removing device in the present embodiment, when the second light-transmitting body 3 is collided, the impact force may be eliminated by the elastic seal ring 16. Due to the elasticity of the elastic seal ring 16, the elastic seal ring 16 may be elastically deformed when being compressed by external forces, reducing or eliminating the impact between the first light-transmitting body 7 and the second light-transmitting body 3, and reducing a possibility that the first light-transmitting body 7, the reflector 1 and the light source 2 are broken by the impact force. Therefore, anti-collision performance of the hair removing device may be enhanced.

Figure 42:
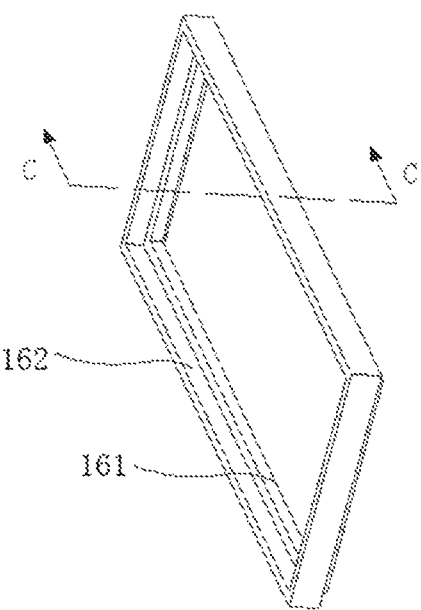
FIG. 42 is a structural schematic view of an elastic seal ring according to an embodiment of the present disclosure.
Figure 43:
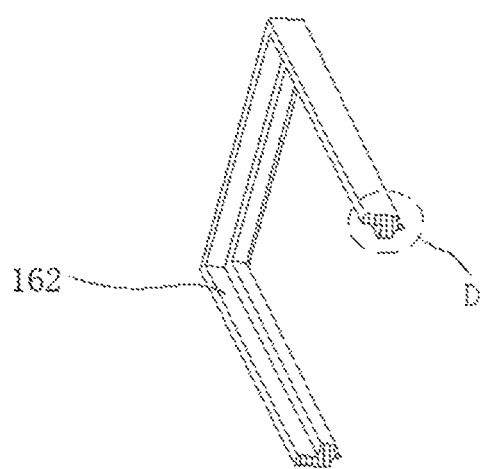
FIG. 43 is a cross sectional view of the embodiment shown in FIG. 42 by taking along the line C-C.
Figure 44:
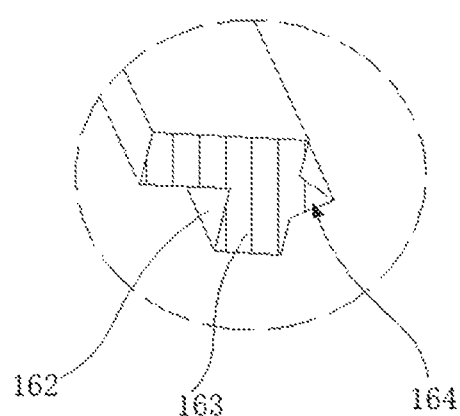
FIG. 44 is an enlarged view of a portion D shown in FIG. 43.

As shown in FIGS. 42 to 44, the elastic seal ring 16 has an inner ring 161 that allows the light to pass through. The light, after being filtered by the first light-transmitting body 7, may be guided to the second light-transmitting body 3 through the inner ring 161 and further irradiate the skin of the user.

In the present embodiment, the first light-transmitting body 7 and the second light-transmitting body 3 may be fixed directly to the bracket 6. The first light-transmitting body 7 and the second light-transmitting body 3 cannot be moved relative to the bracket 6. Therefore, while the hair removing device is being used, the second light-transmitting body 3 may be prevented from shifting back relative to bracket 6 caused by a human bone or a sharp object abutting against the second light-transmitting body 3. The first light-transmitting body 7 or the hair removing assembly 100 may be prevented from being irrecoverably deformed due to compression. The elastic seal ring 16 may be irrecoverably deformed when being compressed for a plurality of times. In this way, a light guiding effect of the hair removing device may not be affected, and the waste of the light energy may be avoided.

The elastic seal ring 16 further defines a mounting groove 162 communicated with an opening of the inner ring 161. The mounting groove 162 is defined in a side of the elastic seal ring 16 away from the hair removing assembly 100. The inner ring 161 extends from a bottom wall of the mounting groove 162 towards the first light-transmitting body 7. The second light-transmitting body 3 is partially received in the mounting groove 162 to improve a sealing effect between the second light-transmitting body 3 and the elastic seal ring 16, and further to fix the elastic seal ring 16 to the second light-transmitting body 3 to achieve fixed connection between the elastic seal ring 16 and the second light-transmitting body 3.

In some embodiments, the elastic seal ring 16 may include an outer ring 163 and a projection 164 arranged on a side of the outer ring 163. The projection 164 may abut against the first light-transmitting body 7. A side of the outer ring 163 away from the projection 164 defines the mounting groove 162. The inner ring 161 extends from the bottom wall of the mounting groove 162 towards the projection 164. Each of the outer ring 163 and the projection 164 may be a complete closed-loop structure. The light inside the inner ring 161 may only be emitted outwardly from the second light-transmitting body 3.

In some embodiments, a cross section of the projection 164 may be a triangle that is arranged transversely. A contact area between the projection 164 and the first light-transmitting body 7 may be less than a contact area between the projection 164 and the outer ring 163. Therefore, when the elastic seal ring 16 is arranged, an end of the projection 164 away from the outer ring 163 may be partially curled after being compressed. Since the elastic seal ring 16 is elastic, a curled part of the elastic seal ring 16 may tightly abut against the first light-transmitting body 7. That is, when a distance between the second light-transmitting body 3 and the first light-transmitting body 7 changes slightly, the elastic seal ring 16 may be adjusted by taking the curled part to be adaptive to the change in the distance. In this way, tight or even interference fit between the elastic seal ring 16 and the second light-transmitting body 3 and between the elastic seal ring 16 and the first light-transmitting body 7 may be maintained at all times, and a better sealing effect may be achieved. In other embodiments, the cross section of the projection 164 may be trapezoidal.

In the present embodiment, the elastic seal ring 16 may be a ring, made of laser resistant, high temperature resistant and low temperature resistant material, such that when the elastic seal ring 16 is being used, the elastic seal ring 16 may be prevented from being deformed due to high or low temperatures or laser exposure, increasing a service life of the elastic seal ring 16.

In some embodiments, the hand-held portion 112 may include a housing defining a space in a middle (not marked in the drawings). A surface of the housing may define an air vent 1211. The air vent 1211 may be communicated with an inside of the housing and an outside of the housing, such that the hair removing device may exchange air with the outside through the air vent 1211, and a temperature inside the device may be reduced. The housing may further include an interface 1212 configured to connect to an external power supply for charging the hair removing device. A position where the interface 1212 is arranged on the housing is not limited by the present disclosure.

Figure 36:
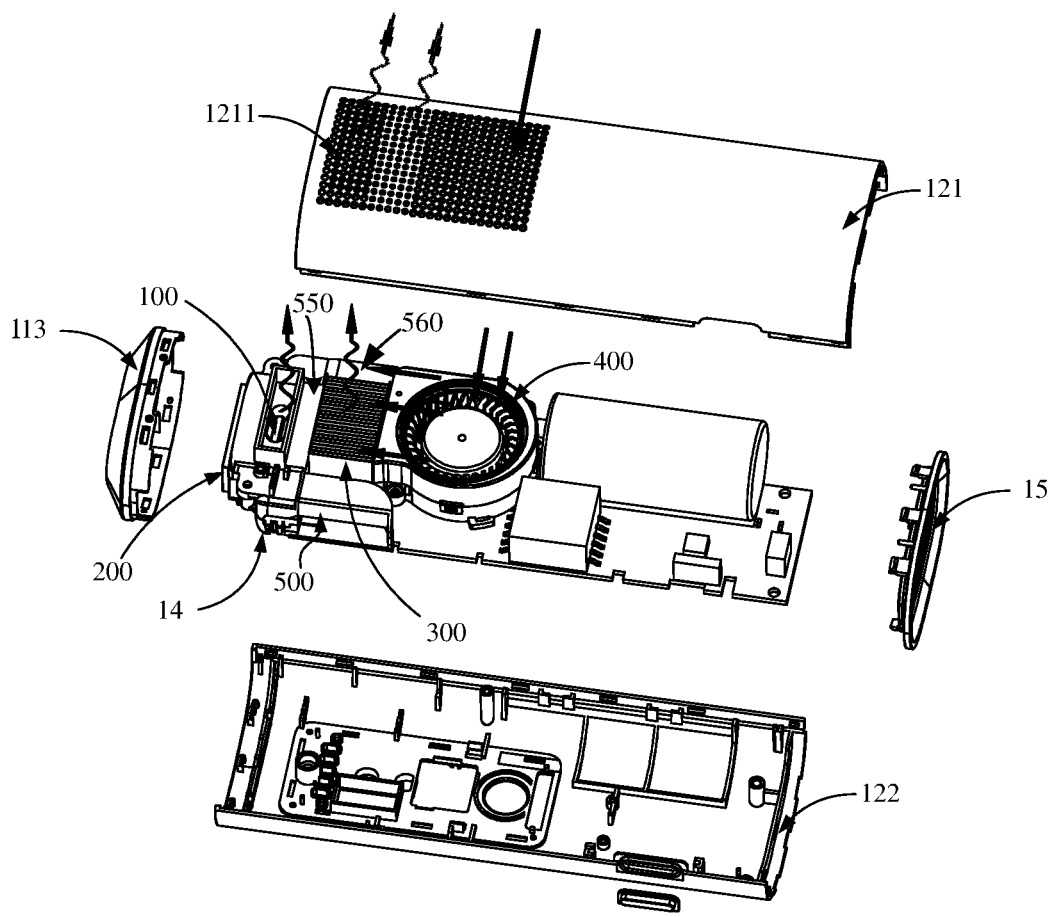
FIG. 36 is an exploded view of a hair removing device according to another embodiment of the present disclosure.

As shown in FIG. 35 and FIG. 36, FIG. 36 is an exploded view of the device according to an embodiment of the present disclosure. An arrow in FIG. 36 shows a direction of airflow inside the hair removing device driven by a cold drive assembly. A straight line represents a direction which cold air flows along, and a wavy line represents a direction which hot air flows along. In detail, the hair removing device may include the housing, a light cover 113 arranged over an opening of the housing, a hair removing mechanism 14 received inside the housing and a bottom cover 15.

In the present embodiment, the housing may include a first housing 121 and a second housing 122. The first housing 121 and the second housing 122 may be snapped with each other to define a cavity and two openings at two ends of the housing. The hair removing mechanism 14 is received in the cavity, the light cover 113 and the bottom cover 15 are arranged to cover the two openings respectively to encapsulate the openings defined by the first housing 121 and the second housing 122 after the first housing 121 and the second housing 122 are snapped with each other to define the cavity.

In some embodiments, the first housing 121, the second housing 122, the light cover 113 and the bottom cover 15 may be connected by snaps, screws, bonding, and so on.

The hair removing mechanism 14 may include the hair removing assembly 100, the cold compressing assembly 200, the heat dissipation assembly 300 and the cold drive assembly 400.

The cold compressing assembly 200 is arranged near the light cover 113. The light cover 113 may define a through hole (not marked in the drawings). A part of the cold compressing assembly 200 is exposed to the outside of the housing through the through hole in the light cover 113 to directly contact the skin. It shall be understood that the part of the cold compressing assembly 200 and the light cover 113 form the head portion 111 of the hair removing device.

The hair removing assembly 100 is arranged on a side of the cold compressing assembly 200 away from the light cover 113 and is configured to emit light to the cold compressing assembly 200. The light may be visible light, such as red light, green light or yellow light. After the light enters the cold compressing assembly 200, the light may pass through the cold compressing assembly 200 to further penetrate the skin to reach the hair follicle under the skin to remove hair.

The heat dissipation assembly 300 is arranged on a side of the cold compressing assembly 200 and is connected to the cold compressing assembly 200. The cold compressing assembly 200 is able to absorb heat from the skin when attaching to the skin to reduce the temperature of the skin and reduce the burning. A temperature of the cold compressing assembly 200 may be increased when being used for a long period of time, and a cooling effect may be reduced. The heat dissipation assembly 300 may absorb the heat of the cold compressing assembly 200, such that the cold compressing assembly 200 may keep operating at a low temperature, ensuring the cooling effect that the cold compressing assembly 200 cools the skin. Therefore, the hair removing device in the present embodiment is able to operate constantly at a low temperature when being used continuously, and the user may not hurt.

The cold drive assembly 400 is arranged on a side of at least a part of the heat dissipation assembly 300 facing away from the hair removing assembly 100 and is configured to dissipate heat from the hair removing assembly 100 and the heat dissipation assembly 300.

In the present embodiment, the cold drive assembly 400 may absorb an external cooling medium, which passes through the air vent 1211 to enter the inside of the hair removing device. The cooling medium may flow along the hair removing assembly 100 and the heat dissipation assembly 300 to remove the heat and further flow out of the device through the air vent 1211.

In some embodiments, the external cooling medium may be air. The cold drive assembly 400 may absorb the air and blows the air towards the hair removing assembly 100 and the heat dissipation assembly 300. Heat of the hair removing assembly 100 and the heat dissipation assembly 300 may be removed by the airflow.

In the present embodiment, the air vent 1211 may be defined in the first housing 121, and at least part of the cold drive assembly 400 faces the air vent 1211, such that the cold drive assembly 400 may better absorb the external cooling medium, which enters the housing through the air vent 1211, and a heat dissipation efficiency may be improved. In other embodiments, the air vent 1211 may be defined in the second housing 122.

Figure 37:
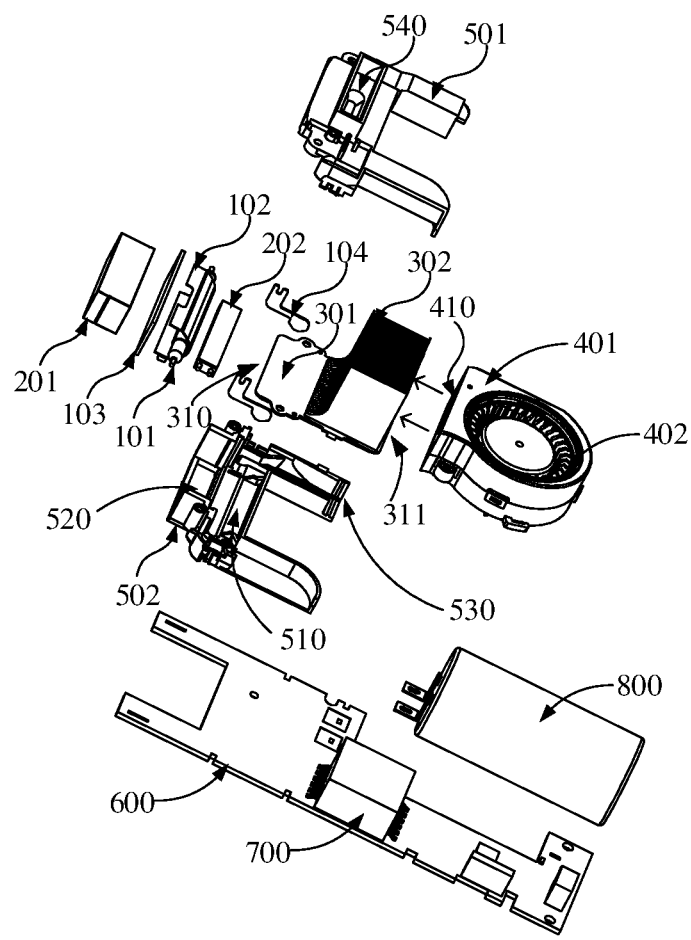
FIG. 37 is an exploded view of the embodiment shown in FIG. 36.

As shown in FIG. 36 and FIG. 37, FIG. 37 is an exploded view of the structure shown in FIG. 36, arrows in FIG. 37 may indicate a direction that air is blown out of a fan.

In the present embodiment, the hair removing device may further include a bracket 500, a circuit board 600, a processor 700 and a capacitor 800. The hair removing assembly 100 and the cold compressing assembly 200 may be arranged inside the bracket 500, and the cold drive assembly 400 may be arranged adjacent to the bracket 500. The hair removing assembly 100, the cold compressing assembly 200 and the cold drive assembly 400 may be mounted on and electrically connected to the circuit board 600.

The processor 700 and capacitor 800 may be electrically connected to and arranged on the circuit board 600. When an external power supply is connected, the external power supply may charge the capacitor 800, such that the capacitor 800 may provide power for the hair removing device. Further, the capacitor 800 may store power when being connected to the external power supply, such that the hair removing device may be used when being not connected to the external power supply. The processor 700 may send control commands to the hair removing assembly 100, the cold compressing assembly 200 and the cold drive assembly 400 to control operation of the hair removing device. For example, the hair removing device may be controlled to be switched on and off, thermal protection of the hair removing device may be controlled, a power of the hair removing device may be adjusted, and so on.

In the present embodiment, the circuit board 600 may be fixed in the second housing 122, and the circuit board 600 may be a PCBA circuit board.

In the art, heat inside the hair removing device may be continuously increased while being used. Circuits and components inside the hair removing device may be exploded, burned, short-circuited, and so on, when being operating at a high temperature. In the present embodiment, the cold drive assembly 400 may dissipate heat from the hair removing assembly 100 and the heat dissipation assembly 300, and the heat dissipation assembly 300 may dissipate heat from the cold compressing assembly 200, such that the cold compressing assembly 200 may compress the skin to cool the skin, allowing the skin to feel comfortable, and preventing the components from being exploded, burned, short-circuited, and so on.

In detail, the hair removing assembly 100 may include a light source 101, a reflector 102, a filter 103 and two electrodes 104.

The light source 101, the reflector 102 and the filter 103 are arranged inside the bracket 500, i.e., the bracket 500 is configured with mounting positions for the light source 101, the reflector 102 and the filter 103. The light source 101, the reflector 102 and the filter 103 may be snap into the mounting positions in the bracket 500, correspondingly.

The light source 101 may be opposite to the cold compressing assembly 200. The light emitted from the light source 101 may be directly injected into the cold compressing assembly 200. The reflector 102 may be disposed on a side of the light source 101 away from the cold compressing assembly 200 and may reflect the light of the light source 101 into the cold compressing assembly 200 to prevent a loss of light energy. The filter 103 is disposed between the light source 101 and the cold compressing assembly 200. That is, the light source 101, the filter 103 and the cold compressing assembly 200 may be disposed sequentially in a direction of light propagation. The filter 103 is configured to filter some harmful light out of the light emitted from the light source 101, such that damages to the skin by the light may be reduced, and safety of hair removing may be increased. The two electrodes 104 may be connected on two sides of the light source 101 and may be electrically connected to the circuit board 600 for transmitting electrical signals.

In some embodiments, the light source 101 may be a lamp, a colour of the light emitted by the lamp may not be limited. The lamp may emit coloured light, composite light, and so on. A wavelength and a frequency of the light may be determined based on demands. A type of the lamp is not limited. The lamp may be a xenon semiconductor lamp, a quartz lamp, a laser lamp, and so on. A type of the light may be intense pulse light (IPL), delicate pulse light (DPL), an optimal pulse technology (OPT), an advanced optimal pulse technology (AOPT), broadband light (BBL), and so on. The type of the light may be determined based on desired effects.

In some embodiments, the reflector 102 may be a U-shaped reflector that surrounds the light source 101. Further, an opening of the U-shaped reflector may face the cold compressing assembly 200, and reflect light that does not enter the cold compressing assembly 200 to the cold compressing assembly 200. In addition, the reflector 102 may prevent the heat generated by the light source 101 from transferring to other components of the hair removing device. In the present embodiment, the bracket 500 may include a fixing frame 550 and a tube 560. The fixing frame 550 may define a first receiving space 510 and a second receiving space 520. The first receiving space 510 is configured for receiving the hair removing assembly 100. The second receiving space 520 is configured for receiving the cold compressing assembly 200. The first receiving space 510 may be adjacent to the second receiving space 520 to reduce a distance between the hair removing assembly 100 and the cold compressing assembly 200, reducing a loss of the light emitted from the hair removing assembly 100. The second receiving space 520 may be closer to the head portion 111 of the hair removing device shown in FIG. 21, compared to the first receiving space 510.

When the hair removing device is operating, the light source 101 may generate a large amount of heat, the reflector 102 and the filter 103 may be irradiated by the light, such that a temperature of the reflector 102 and filter 103 may be increased. Therefore, heat of the light source 101, the reflector 102 and the filter 103 needs to be dissipated.

In the present embodiment, the bracket 500 may include the fixing frame 550 and the tube 560. An end of the tube 560 may be connected to a side of the fixing frame 550, and the other end of the tube 560 may extend towards the cold drive assembly 400. The fixing frame 550 defines an air outlet 540 communicated with the first receiving space 510, and the tube 560 defines an air inlet 530 communicated with the first receiving space 510. The air inlet 530, the first receiving space 510 and the air outlet 540 may be sequentially communicated with each other.

The air inlet 530 may be connected to the cold drive assembly 400. The air outlet 540 may be communicated with the air vent 1211. The cold drive assembly 400 may absorb the external air from the air vent 1211 and blow the air towards the air outlet 540. The air enters the first receiving space 510 through the air outlet 540 and carries the heat away from the light source 101, the reflector 102 and the filter 103 in the first receiving space 510. Further, the air may flow out the device through the air outlet 540 and the air vent 1211 to dissipate the heat.

In some embodiments, a part of the fixing frame 550 and a part of the tube 560 form a first bracket 501, and the remaining part of the fixing frame 550 and the remaining part of the tube 560 form a second bracket 502. In other embodiments, the fixing bracket 550 may be configured as an integral one-piece structure.

The first bracket 501 and the second bracket 502 may be connected to each other through a snap. The first bracket 501 may be disposed near the first housing 121, and the second bracket 502 may be disposed near the second housing 122. The air outlet 540 may be defined in the first bracket 501 and may be opposite to the air vent 1211 in the first housing 1211 to increase the heat dissipation efficiency at the air outlet 540. The first receiving space 510 may be defined in a part of the first bracket 501 and a part of the second bracket 502. The part of the first bracket 501 and the part of the second bracket 502 may correspond to the fixing frame 550 and may be snapped with each other. The air inlet 530 may be defined in another part of the first bracket 501 and another part of the second bracket 502. The another part of the first bracket 501 and the another part of the second bracket 502 may correspond to the tube 550 and may be snapped with each other. The air inlet 530 may be communicated with the first receiving space 510 and connected to the cold drive assembly 400. An inside of the bracket 6 may define a channel for guiding an airflow, facilitating the airflow of the cold drive assembly 400 to be guided into the first receiving space 510.

Therefore, in the present embodiment, the hair removing assembly 100 may dissipate heat through the cold drive assembly 400, ensuring the hair removing device to be used safely.

Further, in the present embodiment, the cold compressing assembly 200 may include a second light-transmitting body 201 and a refrigerating member 202.

The second light-transmitting body 201 may be configured to attach to the skin. The second light-transmitting body 201 may face the light source 101. The second light-transmitting body 201 may be an element allowing the light to pass through. The light emitted by the light source 101 enters the second light-transmitting body 201 and passes through the second light-transmitting body 201 to further reach the skin.

In some embodiments, the second light-transmitting body 201 may be a light conductive crystal, such as sapphire, K9 glass or crystal glass. When the second light-transmitting body 201 is the sapphire, the second light-transmitting body 201 may have excellent thermal conductivity.

In some embodiments, the second light-transmitting body 201 may be cylindrical or cuboid. A face of the second light-transmitting body 201 away from the light source 101 may be configured to attach the skin.

The refrigerating member 202 may be connected to the second light-transmitting body 201 to absorb heat from the second light-transmitting body 201. Since the temperature of the second light-transmitting body 201 is increased when the second light-transmitting body 201 contacts the skin, the refrigerating member 202 may absorb the heat of the second light-transmitting body 201 after the temperature of the second light-transmitting body 201 is increased, such that the second light-transmitting body 201 remains cold, and when the second light-transmitting body 201 is contacting the skin for a long period of time, the second light-transmitting body 201 may still cool the skin, and the burning sensation to the skin may be reduced.

Further, the refrigerating member 202 may be a semiconductor refrigerating member. An end of the refrigerating member 202 that absorbs heat may be connected to the second light-transmitting body 201, and the other end of the refrigerating member 202 may dissipate the heat.

In order to dissipate heat from the heat dissipating end of the refrigerating member 202, in the present embodiment, the heat dissipation assembly 300 is connected to the heat absorbing end of the refrigerating member 202 and absorbs the heat from the refrigerating member 202.

In detail, the heat dissipation assembly 300 may include a heat dissipation plate 301 and a heat dissipation wing 302. A surface of the heat dissipation plate 301 includes a first region 310 and a second region 311 side by side. The hair removing assembly 100 is arranged in the first region 310, and the heat dissipation wing 302 is arranged in the second region 311. The second region 311 is arranged on a side of the fixing frame 550 connected to the tube 560. The heat dissipation wing 302 and the tube 560 are disposed side by side on a side of the fixing frame. The fixing frame 550 is arranged in the first region 310. The heat dissipation plate 301 is arranged on the circuit board 600 and is connected to the cold compressing assembly 200. In detail, the refrigerating member 202 may be bonded to the heat dissipation plate 301 by a thermally-conductive silicone grease. The cold compressing assembly 200 may quickly transfer the heat to the heat dissipation plate 301 through the thermally-conductive silicone grease. The heat dissipation wing 302 may dissipate heat from the heat dissipation plate 301 and assist the heat dissipation plate 301 to dissipate the heat, such that the heat dissipation plate 301 may continuously absorb heat from the refrigerating member 202.

In some embodiments, the number of heat dissipation wings 302 may be more than one. The more than one heat dissipation wings 302 may be parallel to each other and may be mounted on the heat dissipation plate 301 by welding.

In some embodiments, a surface of the heat dissipation wing 302 may be sprayed with a heat-conductive paint. The heat-conductive paint may radiate to dissipate the heat away from the heat dissipation wing 302, and may prevent the heat dissipation wing 302 from being affected by water, being corroded and being worn.

In the present embodiment, the heat dissipation plate 301 may be a temperature homogeneous plate. When a liquid inside the temperature homogeneous plate encounters an environment at a high temperature, the liquid may absorb heat and may be vaporized into gas. When the gas encounters an environment at a low temperature, the gas may dissipate heat and may be liquified into the liquid. Therefore, a temperature of a surface of the temperature homogeneous plate may be kept homogeneous due to periodic evaporation and condensation. Therefore, a part of the surface of the heat dissipation plate 301 is connected to the refrigerating member 202, and the other part is connected to the heat dissipation wing 302, such that the heat generated by the refrigerating member 202 may be dissipated through the heat dissipation plate 301 and the heat dissipation wing 302.

Figure 38:
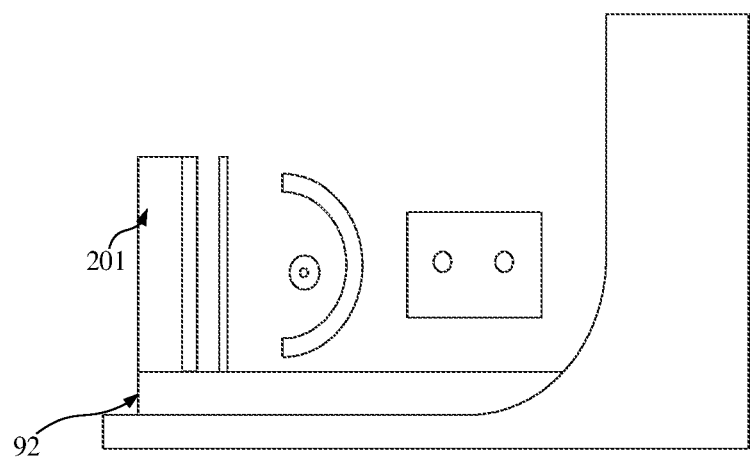
FIG. 38 is a structural schematic view of a carbon-containing layer according to another embodiment of the present disclosure.

In some embodiments, as shown in FIG. 38, the carbon-containing layer 92 may be disposed between the second light-transmitting body 201 and the heat dissipation assembly 300, such as on a surface of the heat dissipation plate 301 thermally coupling with the second light-transmitting body 201. The carbon-containing layer 92 has excellent thermal conductivity, and may accelerate a thermal conducting rate of the heat dissipation plate 301 and improve heat dissipation performance of the heat dissipation assembly 300.

In some embodiments, the carbon-containing layer may be a graphene material, graphite powder, a graphite sheet or a graphite film.

In some embodiments, the carbon-containing layer may be arranged by plating, spraying or attaching.

In order to improve the heat dissipation performance of the heat dissipation assembly 300, in the present embodiment, the heat dissipation assembly 300 may further be connected to the cold drive assembly 400.

In detail, the heat dissipation wing 302 of the heat dissipation assembly 300 may be connected to the cold drive assembly 400. The cold drive assembly 400 may absorb the external air through the air vent 1211 and drive the air to flow towards the heat dissipation wing 302. The air may flow along the heat dissipation wing 302 to dissipate heat from the heat dissipation wing 302.

In an example, the heat dissipation wing 302 may be arranged parallel to an airflow direction driven by the cold drive assembly 400 to increase a contact area between the heat dissipation wing 302 and the airflow, increasing the efficiency of dissipating heat from the heat dissipation wing 302.

The heat dissipation wing 302 may face the air vent 1211 in the first housing 121. The airflow, after flowing along the heat dissipation wing 302, may quickly flows out of the device through the air vent 1211.

Therefore, the cold drive assembly 400 of the present embodiment may drive the cooling medium to dissipate heat from the hair removing assembly 100, and may further dissipate heat from the heat dissipation base 300. With improved safety, the irradiated skin may be compressed to be cooled, and burning of the irradiated skin may be reduced. Further, the cold compressing assembly 200 may be controlled by the heat dissipation assembly 300 and the cold drive assembly 400 to reach a low temperature of about zero degrees. In this way, the skin near a light outlet port may infinitely approach a freezing point, burning sensation of the skin may be reduced, and a short contact between the skin the device may not cause damage to the skin.

Figure 39:
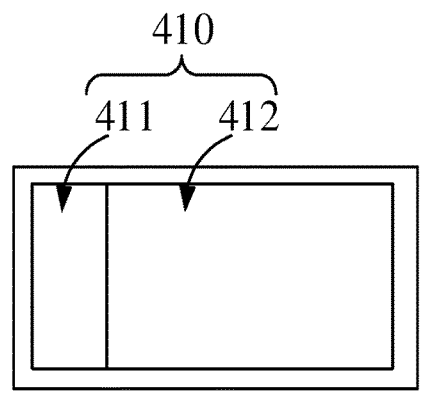
FIG. 39 is a structural schematic view of an air outlet of a fan housing of the embodiment shown in FIG. 37.

As shown in FIG. 36, FIG. 37 and FIG. 39, FIG. 39 is a structural schematic view of an air outlet of a fan housing of the embodiment shown in FIG. 37. In the present embodiment, the cold drive assembly 400 may include a fan housing 401 and a fan 402. The fan housing 401 is arranged on a side of the heat dissipation assembly 300 away from the cold compressing assembly 200, and the fan 402 is received inside the fan housing 401.

An air inlet end of the fan 402 faces the air vent 1211 in the first housing 121. The fan 402 drives the external air to flow into the fan 402 through the air vent 1211. The fan housing 401 defines an air outlet 410 for outputting air. An air outlet end of the fan 402 is connected to the air outlet 410. The fan 402 drives the external air to flow into the fan 402 through the air vent 1211 and further drives the air to flow out through the air outlet 410.

In some embodiments, the fan 402 may be a centrifugal fan, an axial flow fan, a mixed flow fan or a cross flow fan.

Further, the air outlet 410 may include a first air outlet 411 and a second air outlet 412. Air at the air outlet 410 of the fan 402 may be divided into two parts. One of the two parts of the air flows out of the device through the first air outlet 411, and the other one of the two parts of the air flows out of the device through the second air outlet 412.

In some embodiments, the air outlet 410 may further include a third air outlet or more air outlets. The present disclosure does not limit the number of the air outlets.

In the present embodiment, the first air outlet 411 is communicated with the air inlet 530 of the bracket 500. The fan 402 drives the external air to enter the fan 402 through the air vent 1211. The fan 402 drives the air to flow from the first air outlet 411 and the air inlet 530 into the first receiving space 510. The air in the first receiving space 510 may carry the heat away from the light source 2, the reflector 1 and the filter 103. Finally, the air flows out of the device from the air outlet 540 and the air vent 1211. In this way, heat is dissipated to the outside of the device, enabling the heat of the hair removing assembly 100 to be dissipated.

In the present embodiment, the second air outlet 412 is connected to the heat dissipation wing 302 of the heat dissipation assembly 300. The fan 402 drives the external air to enter the fan 402 from the air vent 1211. The fan 402 drives the air to flow between every two of the more than one heat dissipation wings 302 of the heat dissipation assembly 300 through the second air outlet 412. The air flows along the heat dissipation wings 302, carries the heat away from the heat dissipation wings 302, and further flows out of the device from the air vent 1211. After temperatures of the heat dissipation wings 302 are decreased, the heat of the heat dissipation plate 301 may be decreased accordingly. In this way, the heat dissipation plate 301 may absorb the heat of the cold compressing assembly 200, enabling the heat of the cold compressing assembly 200 to be dissipated.

In some embodiments, the amount of the air flowing in the first air outlet 411 and the second air outlet 412 will not be limited herein and may be determined based on demands. The amount of the air flowing in the first air outlet 411 and the second air outlet 412 may be controlled by configuring a size of the first air outlet 411 and a size pf the second air outlet 412. For example, in the present embodiment, an air outlet area of the second air outlet 412 is greater than an air outlet area of the first air outlet 411, such that a larger amount of air flows through the second air outlet 412 to enhance the efficiency of dissipating the heat from the heat dissipation plate 301.

According to the hair removing device in the present embodiment, heat of the hair removing assembly 100, the cold-compressing assembly 200 and the heat dissipation assembly 300 may be dissipated by the cold drive assembly 400, such that heat of the hair removing assembly 100 and the cold-compressing assembly 200 may be dissipated simultaneously. The heat dissipation performance of the hair removing device may be improved, and the safety of the hair removing device may be improved. Further, the skin that is continuously compressed to be cooled may infinitely approach the freezing point, the burning sensation of the skin may be reduced, and the skin may not be damaged when the hair is being removed.

The above description shows only embodiments of the present disclosure and does not limit the scope of the present disclosure. Any equivalent structure or equivalent process transformation performed based on the specification and accompanying drawings, applied directly or indirectly in other fields, shall be equally covered by the scope of the present disclosure.

What is claimed is:
1. A hair removing device, comprising:
a reflector, being capable of reflecting light;
a light source, arranged inside the reflector and capable of emitting light;

a light-transmitting body, having a light incidence surface and a light exiting surface, wherein the light incidence surface is configured to allow the light to enter the light-transmitting body, and the light exiting surface is configured to allow the light to propagate out of the light-transmitting body;

a bracket, wherein the light-transmitting body is fixed to the bracket;

a heat dissipation assembly and a cold drive assembly, and a housing, comprising a first side and a second side opposite to the first side;

wherein the reflector and the light source are disposed at the first side, and the heat dissipation assembly and the cold drive assembly are disposed at the second side;

the heat dissipation assembly is connected to the light-transmitting body and is configured to absorb heat from the light-transmitting body;

the housing further defines an air inlet, which is communicated with the second side and is connected to the cold drive assembly;

the cold drive assembly is configured to absorb external air, the cold drive assembly is further configured to:

blow a part of the air to flow through the air inlet to reach the reflector and the light source at the first side, and blow the rest part of the air to flow, without passing through the air inlet, to reach the heat dissipation assembly at the second side to further flow out of the hair removing device, enabling heat of the heat dissipation assembly, the reflector, and the light source to be dissipated by the air.

2. The hair removing device according to claim 1, further comprising:

a carbon-containing layer, arranged in the reflector.

3. The hair removing device according to claim 2, further comprising:

a heat dissipation base, arranged on a side of the reflector and configured to cool the reflector; wherein the carbon-containing layer is arranged on the heat dissipation base.

4. The hair removing device according to claim 3, wherein, the carbon-containing layer is disposed between the heat dissipation base and the reflector, and/or disposed on an exposed surface of the heat dissipation base.

5. The hair removing device according to claim 3, further comprising:

a filter, disposed between the light-transmitting body and the reflector; wherein a groove body is arranged on a side of the heat dissipation base, the reflector is embedded in the groove body, and the filter is fixed relative to the heat dissipation base.

6. The hair removing device according to claim 5, wherein the bracket defines a window, and the filter is fixed with the bracket and covers the window.

7. The hair removing device according to claim 6, wherein the light-transmitting body is received in the window, and the light-transmitting body is disposed on a side of the filter away from the light source.

8. The hair removing device according to claim 5, further comprising an elastic seal ring, wherein at least an inner part of the elastic seal ring is disposed between and elastically abuts against the filter and the light-transmitting body; and the filter and the light-transmitting body are sealed with the elastic seal ring.

9. The hair removing device according to claim 8, wherein, the elastic seal ring comprises an inner ring and an outer ring, a diameter of the inner ring is less than a diameter of the outer ring;

the outer ring is connected to a periphery of the inner ring and extends beyond the inner ring towards the light-transmitting body, the outer ring and the inner ring cooperatively define a mounting groove; and a circumference of an end of the light-transmitting body facing the filter is received in the mounting groove.

10. The hair removing device according to claim 8, wherein, a projection is arranged on a side of the elastic seal ring facing the filter; and the projection abuts against an end face of the filter.

11. The hair removing device according to claim 1, further comprising:

a carbon-containing layer, disposed between the light-transmitting body and the heat dissipation assembly.

12. The hair removing device according to claim 11, wherein, the heat dissipation assembly comprises a heat dissipation plate and a heat dissipation wing;

a surface of the heat dissipation plate comprises a first region and a second region side by side;

the light source and the reflector are arranged in the first region of the heat dissipation plate, the heat dissipation wing is arranged in the second region; and the cold drive assembly is disposed on a side of the heat dissipation wing away from the reflector, the cold drive assembly is configured to drive air to flow to the heat dissipation wing, the light source, and/or the reflector.

13. The hair removing device according to claim 2, wherein the carbon-containing layer is graphene, graphite powders, a graphite sheet or a graphite film, and the carbon-containing layer is arranged by plating, spraying or attaching.

14. The hair removing device according to claim 1, wherein, a center of the light source is located between a focal point of the reflector and a bottom of the reflector;

the light incidence surface of the light-transmitting body is disposed between the light exiting surface and the focal point of the reflector; and the light reflected by the reflector is focused at a position between the light exiting surface of the light-transmitting body and the focal point of the reflector.

15. The hair removing device according to claim 14, wherein, the reflector has a first reflective region and a second reflective region;

the first reflective region is a curved region comprising the bottom of the reflector, the second reflective region is two flat regions extending outwards from two ends of the curved region; and the flat region is tangential to the curved region.

16. The hair removing device according to claim 15, wherein an angle between one of the two flat regions and a reference line is in a range of 5 degrees to 20 degrees, and the reference line is a line between a center of the light source and a center of the second light-transmitting body.

17. The hair removing device according to claim 5, further comprising: another light-transmitting body, a heat dissipation base, and a refrigerating member, wherein the filter is a part of the another light-transmitting body;

the another light-transmitting body is arranged on a light exiting side of the reflector, and the another light-transmitting body and the reflector cooperatively define a cavity to receive the light source;

a side of the heat dissipation base side is thermally coupled to the reflector;

a refrigerating side of the refrigerating member is thermally coupled to the other side of the heat dissipation base and/or thermally coupled to a side of the reflector; and a body of the light source is suspended in the cavity, and the refrigerating member is configured to cool the cavity.

18. The hair removing device according to claim 17, wherein, the heat dissipation base comprises a heat dissipation plate and a heat dissipation wing;

a surface of the heat dissipation plate comprises a first region and a second region side by side;

the light source and the reflector are arranged in the first region of the heat dissipation plate, the heat dissipation wing is arranged in the second region; and the cold drive assembly is disposed on a side of the heat dissipation wing away from the reflector, the cold drive assembly is configured to drive air to flow to the heat dissipation wing, the light source, and/or the reflector.

19. The hair removing device according to claim 18, wherein the light source is a strip-shaped lamp, the reflector is a semi-curved reflector, the hair removing device comprises:

a side reflecting member, disposed at each of two ends of the reflector in a length direction of the reflector and being configured to reflect light that escapes from the two ends of the reflector to the light exiting side of the reflector.

20. The hair removing device according to claim 19, wherein, the side reflecting member and the reflector are configured as an integral one-piece structure; and the side reflecting member defines a through hole, each of the two ends of the light source passes through the through hole.

* * * * *